United States Patent
Dmochowski et al.

(10) Patent No.: US 8,470,587 B2
(45) Date of Patent: Jun. 25, 2013

(54) $^{129}$XE BIOSENSORS AND THEIR USE

(75) Inventors: Ivan Dmochowski, Philadelphia, PA (US); Qian Wei, Delran, NJ (US); Nicholas Kuzma, Rochester, NY (US); P. Aru Hill, Santa Clara, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 478 days.

(21) Appl. No.: 12/376,323

(22) PCT Filed: Aug. 6, 2007

(86) PCT No.: PCT/US2007/017480
§ 371 (c)(1),
(2), (4) Date: Dec. 28, 2010

(87) PCT Pub. No.: WO2008/027162
PCT Pub. Date: Mar. 6, 2008

(65) Prior Publication Data
US 2011/0104075 A1     May 5, 2011

Related U.S. Application Data

(60) Provisional application No. 60/840,436, filed on Aug. 28, 2006.

(51) Int. Cl.
*C12M 1/34*     (2006.01)

(52) U.S. Cl.
USPC ........................................ 435/287.1; 435/7.1

(58) Field of Classification Search
None
See application file for complete search history.

(56) References Cited

U.S. PATENT DOCUMENTS 7,385,395 B2 *   6/2008   Pines et al. .................... 324/301
8,222,022 B2 *   7/2012   Dmochowski et al. ..... 435/287.1

OTHER PUBLICATIONS

Wei Q. et al., Designing 129Xe NMR Biosensors for Matrix Metalloproteinase Detection, Journal of American Chemical Society (JACS), Published on Web Sep. 16, 2006, pp. A-J.*
Cheng G. et al., Near-Infrared Fluorescent RGD Peptides for Optical Imaging of Integrin avb3 Expression in Living Mice, Bioconjugate Chem., 2005, vol. 16, pp. 1433-1441.*
Spence MM. et al., Functionalized xenon as a biosensor, PNAS, Sep. 2001, vol. 98, No. 19, pp. 10654-10657.*
Huber J.G. et al., NMR Study of Optically Active Monosubstituted Cryptophanes and Their Interaction with Xenon, J. Phys. Chem. A, 2004, vol. 108, pp. 9608-9615.*

* cited by examiner

*Primary Examiner* — Jon P Weber
*Assistant Examiner* — Satyendra Singh
(74) *Attorney, Agent, or Firm* — Mark S. Cohen; Pearl Cohen Zedek Latzer, LLP

(57) ABSTRACT

This invention relates to enzyme-sensitive biosensors and methods and kits using the same. Specifically, the invention relates to methods, systems and kits for the detection of enzymes using the chemical shift observed in an isotope complexed to the biosensor resulting from a change in the biosensor as the result of the enzyme's activity.

19 Claims, 28 Drawing Sheets

(a)

(b)

A

B

| Linker | Distance | $K_d$ |
|---|---|---|
| | 5 bonds | -- |
| | 6 bonds | 1.64 µM |
| | 6 bonds | -- |
| | 7 bonds | -- |
| | 7 bonds | -- |
| | 8 bonds | 0.25 µM |

US 8,470,587 B2

$^{129}$XE BIOSENSORS AND THEIR USE

CROSS-REFERENCE TO RELATED APPLICATIONS

This application is a National Phase Application of PCT International Application No. PCT/US07/17480, International Filing Date 6 Aug. 2007, claiming priority of U.S. Provisional Patent Application, 60/840,436, filed 28 Aug. 2006, both which are incorporated herein by reference in their entirety.

FIELD OF INVENTION

This invention is directed to enzyme-sensitive biosensors. Specifically, the invention relates to methods, systems and kits for the detection of enzymes using the chemical shift observed in a noble element complexed to the biosensor resulting from a change in the biosensor as the result of the enzyme's activity.

BACKGROUND OF THE INVENTION

Nuclear magnetic resonance (NMR) spectroscopy offers tremendous opportunities for high-resolution, minimally-invasive, molecular imaging of deep tissue for the early diagnosis and treatment of disease. However, low sensitivity and complex background signals compromise biomarker detection. Recently, laser-polarized $^{129}$Xe has gained attention as an MR probe, due to its large signal (10-70% alignment of Xe nuclear spins, compared to thermal polarization of 0.00027% at 37° C. and 3 T) and wide NMR chemical-shift window (>200 ppm in water). Xenon gas is soluble in biological fluids (~3.5 mM/atm at 37° C.), non-toxic, and readily delivered by inhalation or perfusion. Furthermore, the environmental sensitivity of xenon chemical shift and relaxation parameters should allow the detection of multiple species in solution simultaneously. Xenon represents, therefore, a useful probe for studying biological samples.

Xenon has been shown to bind cryptophane-A reversibly and with high affinity ($K_A$=3900 M$^{-1}$ at 278 K in $C_2D_2Cl_4$, $K_A$ is higher in water). $^{129}$Xe that is free in aqueous solution or bound inside the cage is distinguished by a greater than 120 ppm difference in $^{129}$Xe NMR chemical shift. In order to couple $^{129}$Xe chemical shifts with specific biological processes, known methods were exploited for functionalizing the organic cage. Attaching biotin to cryptophane-A created a variety of biosensors for streptavidin, whose binding produced as much as a 4 ppm change in $^{129}$Xe chemical shift. $^{129}$Xe biosensors offer the possibility to functionalize various xenon-binding cages with different recognition units.

SUMMARY OF THE INVENTION

In one embodiment, provided herein is an enzyme-detection system comprising a biosensor wherein said biosensor comprises a hyperpolarized noble element complexed with a monopropargyl-cryptophane-A coupled peptide, wherein the peptide is a substrate, specific to said detected enzyme and whereby cleavage of the substrate by the enzyme induces change in the chemical environment of the noble element resulting in a chemical shift detectable by $^{129}$Xe NMR spectroscopy.

In another embodiment, provided herein is a method of synthesizing an enzyme-responsive biosensor, comprising the steps of: alkylating cyclotriguaiacylene with a [3-propargyloxy-4-(2-iodoethoxy)phenyl]methanol linker, in the presence of cesium carbonate, obtaining 12-[2-(4-hydroxymethyl-2-propargyloxyphenoxy)ethoxy]-3,8,13-trimethoxy-10,15-dihydro-5H-tribenzo[a,d,g]cyclononene-2,7-diol; alkylating the resulting 12-[2-(4-hydroxymethyl-2-propargyloxyphenoxy)ethoxy]-3,8,13-trimethoxy-10,15-dihydro-5H-tribenzo[a,d,g]cyclononene-2,7-diol with two [4-(2-iodoethoxy)-3-methoxyphenyl]methanol linkers in the presence of $Cs_2CO_3$, yielding {3-propargyloxy-4-[2-(3,8,13-trimethoxy-7,12-bis[2-(4-hydroxymethyl-2-methoxyphenoxy)ethoxy]-10,15-dihydro-5H-tribenzo-[a,d,g]cyclononen-2-yloxy)ethoxy]phenyl}methanol; cyclizing the obtained {3-propargyloxy-4-[2-(3,8,13-trimethoxy-7,12-bis[2-(4-hydroxymethyl-2-methoxyphenoxy)ethoxy]-10,15-dihydro-5H-tribenzo-[a,d,g]cyclononen-2-yloxy)ethoxy]phenyl}methanol, in the presence of methanol and perchloric acid, yielding monopropargyl-cryptophane-A; Cu(I)-mediated coupling of the obtained monopropargyl-cryptophane-A with a resin-associated azido-peptide, wherein the peptide is a substrate of the enzyme; cleaving the resin from the monopropargyl-cryptophane-A coupled resin-associated peptide; and complexing a hyperpolarized noble element with the monopropargyl-cryptophane-A coupled peptide, wherein said hyperpolarized noble element undergoes a chemical shift in response to enzymatic cleavage of the peptide.

In one embodiment, provided herein is method of analyzing the activity of a matrix metalloproteinase or caspase in a biological sample of a subject, comprising the step of contacting the biological sample with an enzyme-responsive biosensor comprising a hyperpolarized noble element complexed with a monopropargyl-cryptophane-A coupled peptide, wherein the peptide is a substrate, specific to said matrix metalloproteinase or caspase, whereby cleavage of the substrate by the matrix metalloproteinase or caspase induces change in the chemical environment of the noble element resulting in a chemical shift detectable by NMR; and analyzing the chemical shift in said element, whereby a $^{129}$Xe NMR chemical shift indicates activity of said metalloproteinase, caspase, or generic protease.

In another embodiment, provided herein is a kit for screening for a matrix metalloproteinase activity in a biological sample, comprising a biosensor responsive to said matrix metalloproteinase, said biosensor comprising a hyperpolarized noble element complexed with a monopropargyl-cryptophane-A coupled peptide, wherein the peptide is a substrate, specific to said detected enzyme and whereby cleavage of the substrate by the enzyme induces change in the chemical environment of the noble element resulting in a chemical shift detectable by NMR; and instructions for use.

In one embodiment, provided herein is a kit for screening for caspase activity in a biological sample, comprising a biosensor responsive to said caspase, said biosensor comprising a hyperpolarized noble element complexed with a monopropargyl-cryptophane-A coupled peptide, wherein the peptide is a substrate, specific to said caspase and whereby cleavage of the substrate by the caspase induces change in the chemical environment of the noble element resulting in a chemical shift detectable by NMR; and instructions for use.

In another embodiment, provided herein is a method for screening for a candidate agent capable of modulating the activity of an enzyme in a biological sample, comprising the step of contacting a first portion of the biological sample with a biosensor sensitive to the enzyme, said biosensor comprising a hyperpolarized noble element complexed with a monopropargyl-cryptophane-A coupled peptide, wherein the peptide is a substrate, specific to said detected enzyme and whereby cleavage of the substrate by the enzyme induces a change in the chemical environment of the noble element resulting in a detectable chemical shift; contacting a second portion with the candidate agent screened; contacting the second portion with the same biosensor; and comparing the detected chemical shift, whereby a change in the chemical shift between the first and second portions indicate an agent capable of modulating the activity of the enzyme.

In one embodiment, provided herein is an in-vivo cancer cell detection system comprising: a detectably labeled biosensor wherein said biosensor comprises: a hyperpolarized noble element; complexed with a monopropargyl-cryptophane-A coupled peptide, wherein the peptide is capable of binding an integrin and whereby cellular uptake of the biosensor bound to the integrin by the cancer cell is detectable.

In another embodiment, provided herein is a method of diagnosing a cancer in vivo in a subject, comprising the step of contacting a suspected cell with a composition comprising a detectably labeled biosensor wherein said biosensor comprises: a hyperpolarized noble element; complexed with a monopropargyl-cryptophane-A coupled peptide, wherein the peptide is capable of binding an integrin expressed on the surface of the suspected cell and analyzing the change in fluorescent intensity of the cell before and after administration of the composition, whereby increase in fluorescent intensity, indicates the cell is cancerous.

DETAILED DESCRIPTION OF THE INVENTION

Figure 1:
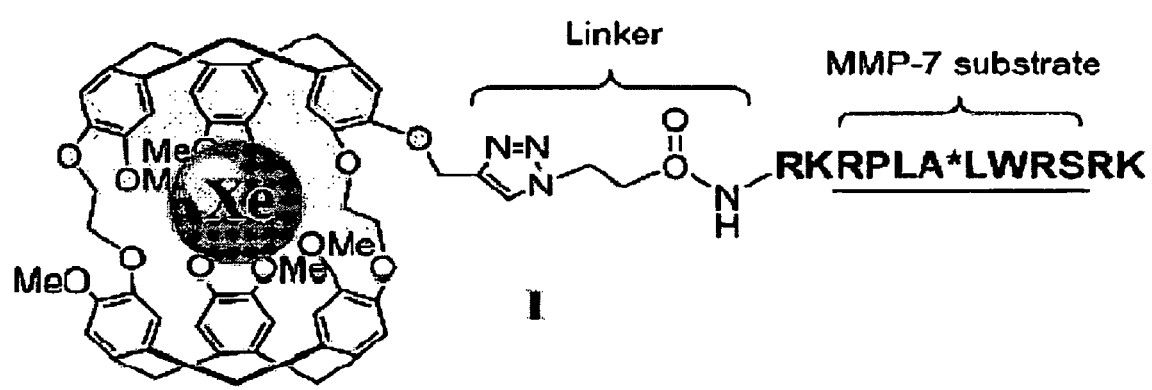
FIG. 1 shows the structure of an MMP-7-responsive $^{129}$Xe biosensor I, with xenon-binding cage, linker, and MMP-7-preferred peptide substrate (underlined in blue). Star indicates the enzyme cleavage site, while xenon (green sphere) is observed within the cage on the NMR time scale.

This invention relates in one embodiment to enzyme-sensitive biosensors. Specifically, provided herein are embodiments of methods, systems and kits for the detection of enzymes using the chemical shift observed in an noble element complexed to the biosensor resulting from a change in the biosensor as the result of the enzyme's activity.

In one embodiment, efforts to develop $^{129}$Xe biosensors as cancer diagnostic agents will benefit from previous applications of hyperpolarized $^{129}$Xe for in vivo imaging. Hyperpolarized $^{129}$Xe MRI has been performed on the bodies and brains of rats, the lungs of mice, dogs, and humans, and in animal tumors. In one embodiment, hyperpolarized $^{129}$Xe is delivered in vivo by inhalation or in another embodiment, through direct injection of xenon-saturated perdeuterated or perfluorocarbon solutions. Pines and coworkers recently demonstrated the application of xenon biosensors in heterogeneous mixtures by obtaining MR images of the biotin-labeled biosensor attached to avidin-coated agarose beads (Hilty, C.; Lowery, T. J.; Wemmer, D. E.; Pines, A. *Angew. Chem., Int. Ed. Engl.* 2006, 45, 70-73.) In one embodiment, using the biosensors described herein with the methods and kits described herein, will enable the distinguishing of healthy cells from cancer cells by $^{129}$Xe NMR spectroscopy.

In one embodiment, the terms "hyperpolarize", "polarize", and the like are used interchangeably and mean to artificially enhance the polarization of certain noble gas nuclei over the natural levels at thermal equilibrium. Such an increase is desirable in other embodiments because it allows stronger signals corresponding to better NMR images and spectroscopy signals of the gas in the body. As is known by those of skill in the art, hyperpolarization can be induced in one embodiment by spin-exchange with an optically pumped alkali-metal vapor or by metastability exchange in another embodiment.

Current limitations in developing $^{129}$Xe MRI contrast agents for in vivo studies include the difficulties of synthesizing large quantities of functionalized cryptophanes and delivering laser-polarized $^{129}$Xe to living tissue. Improved methods for synthesizing xenon biosensors are crucial to developing this technology for in vivo applications. Because the lifetime of hyperpolarized $^{129}$Xe is relatively short in biological fluids, in one embodiment hyperpolarized $^{129}$Xe is continuously delivered to the site of the cryptophane, thereby maintaining signal intensity. Thus, in one embodiment, xenon biosensors described in the systems, methods and kits described herein utilize $^{129}$Xe MR spectroscopic identification of biomarkers in the lungs, where hyperpolarized xenon could be delivered through semi-continuous inhalation. In another embodiment, for application in less accessible target areas, such as the breast, hyperpolarized xenon and said biosensors are delivered through direct injection.

Therefore, provided herein is an enzyme-detection system comprising biosensor wherein said biosensor comprises a hyperpolarized noble element complexed with a monopropargyl-cryptophane-A coupled peptide, wherein the peptide is a substrate, specific to said detected enzyme and whereby cleavage of the substrate by the enzyme induces change in the chemical environment of the noble element resulting in a chemical shift detectable by NMR. In another embodiment, the biosensor used in the systems, methods and kits described herein, is an isotope of a noble element, or in one embodiment, of other elements capable of complexing stably with the monopropargyl-cryptophane-A coupled peptide disclosed herein.

In one embodiment, the term "substrate", refers to a substance acted upon by an enzyme in a biochemical reaction. After the biochemical reaction, at least one product is generated due to the action of the enzyme on the substrate. A "soluble substrate" refers in another embodiment, to a substrate which is not membrane bound. The term "enzyme" refers to any protein that catalyzes a biochemical reaction. Proteins having non-amino-acid modifications such as glycosylation or containing other non-proteinaceous components such as metal ion prosthetic groups are included within this definition.

The term "chemical shift" refers in one embodiment to circumstances whereby, for a Xe-129 atom having a particular NMR resonance frequency within a cryptophane or related organic cage which shields the xenon nucleus from the external magnetic field to a certain extent, a change in the environment of the cryptophane cage will result in a change of the ability of the cryptophane to shield the xenon from the magnetic field. The resulting shift of the NMR resonant frequency is referred to as a "chemical shift" and the degree of shielding depends on the degree to which the very polarizable xenon nucleus is perturbed within a given cryptophane. In one embodiment, the cleavage of the peptides described in Table III, which are coupled to the monopropargyl-cryptophane-A, used in the systems, methods and kits described herein by the corresponding enzyme described in Table III, induces change in the ability of the monopropargyl-cryptophane-A to shield the complexed hyperpolarized noble element from the applied magnetic field, resulting in a chemical shift that is detectable by NMR; and is specific to the enzyme sought to be detected.

TABLE III

Enzymes and their specific substrates

| MMP | Specific substrate Peptide |
|---|---|
| MMP-1 | Pro-Gln-Gly-Ile-Ala-Gly-Gln-D-Arg (SEQ ID NO. 1); Pro-Leu-Ala-Leu-Trp-Ala-Arg-OH (SEQ ID NO. 2); |
| MMP-2 | Pro-Leu-Gly-Leu-Trp-Ala-D-Arg-NH$_2$ (SEQ ID NO. 3); Pro-Leu-Ala-Nva-Dpa-Ala-Arg-NH$_2$ (SEQ ID NO. 4) |
| MMP-3 | Arg-Pro-Lys-Pro-Val-Glu-Trp-Arg-Lys-NH$_2$ (SEQ ID NO. 5); Pro-Tyr-Ala-Tyr-Trp-Met-Arg-OH (SEQ ID NO. 6) |
| MMP-7 | Arg-Lys-Arg-Pro-Leu-Ala-Leu-Trp-Arg-Ser-Arg-Lys-NH$_2$ (SEQ ID NO. 7) |
| MMP-8 | Pro-Leu-Ala-Tyr-Trp-Ala-Arg-OH (SEQ ID NO. 8) |
| MMP-9 | Pro-Leu-Gly-Leu-Trp-Ala-D-Arg-NH$_2$ (SEQ ID NO. 9); Pro-Leu-Ala-Leu-Trp-Ala-Arg-OH (SEQ ID NO. 10) |
| MMP-11 | Ala-Gly/Ala-Ala-Met-Phe/Ala-Leu-NH$_2$ (SEQ ID NO. 11) |
| MMP-13 | Pro-Cha-Gly-His-Ala-NH$_2$ (SEQ ID NO. 12) |
| MMP-14 | Pro-Leu-Ala-Cys(p-OMeBz)-Trp-Ala-Arg(Dpa)-NH$_2$ (SEQ ID NO. 13) |
| MMP-17 | Pro-Leu-Ala-Gln-Ala-Val-Dpa-Arg-Ser-Ser-Ser-Arg-NH$_2$ (SEQ ID NO. 14) |
| MMP-26 | Pro-Leu-Ala-Nva-Dpa-Ala-Arg-NH$_2$ (SEQ ID NO. 15) |
| Gelatinase A/ Gelatinase B | H$_2$N-(Gly-Pro-Hyp)$_5$-Gly-Pro-Lys-Gly-Pro-Pro-Gly-Val-Val-Gly-Glu-Lys-Gly-Glu-Gln-(Gly-Pro-Hyp)$_5$-NH$_2$ (SEQ ID NO. 16) |
| Caspase-1 | Asn-Glu-Ala-Tyr-Val-His-Asp-Ala-Pro-Val-Arg-Ser-Leu-Asn-OH (SEQ ID NO. 17); Tyr-Val-Ala-Asp-Ala-Pro-Val (SEQ ID NO. 18) |
| Caspase-2 | Val-Asp-Val-Ala-Asp-Ala-Phe-Cys (SEQ ID NO. 19); Val-Asp-Val-Ala-Asp-Gly-Trp-Lys-NH$_2$ (SEQ ID NO. 20) |
| Caspase-3 | Ac-Asp-Glu-Val-Asp-Ala-Met-Cys (SEQ ID NO. 21); Asp-Glu-Val-Asp-Ala-Pro-Lys-OH (SEQ ID NO. 22) |
| Caspase-4 | Leu-Glu-Val-Asp-Gly-Trp-Lys-OH (SEQ ID NO. 23); Ac-Leu-Glu-Val-Asp (SEQ ID NO. 24) |
| Caspase-5 | Ac-Trp-His-Glu-Asp (SEQ ID NO. 25) |
| Caspase-6 | Ac-Val-Glu-Ile-Asp (SEQ ID NO. 26) |
| Caspase-7 | Val-Asp-Gln-Val-Asp-Gly-Trp-Lys-NH$_2$ (SEQ ID NO. 27) |
| Caspase-8 | Ile-Glu-Thr-Asp (SEQ ID NO. 28) |
| Caspase-9 | Ac-Leu-Glu-His-Asp (SEQ ID NO. 29) |
| Protease | | where Ac = Acetyl

In another embodiment, the term "protein" or "polypeptide", or "peptide" is used in its broadest sense to refer to a compound of two or more subunit amino acids, amino acid analogs, or other peptidomimetics. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If in another embodiment, the peptide chain is long, the peptide is typically called a polypeptide or a protein. Full-length proteins, analogs, and fragments thereof are encompassed by the definition. The terms also include postexpression modifications of the polypeptide, for example, glycosylation, acetylation, phosphorylation and the like. In another embodiment, as ionizable amino and carboxyl groups are present in the molecule, a particular polypeptide may be obtained as an acidic or basic salt, or in neutral form. In one embodiment, a polypeptide may be obtained directly from any source organism, or may be recombinantly or synthetically produced.

In one embodiment, the term "specific", in reference to the binding of two molecules or a molecule and a complex of molecules, refers to the specific recognition of one for the other and the formation of a stable complex, as compared to substantially less recognition of other molecules and the lack of formation of stable complexes with such other molecules. In another embodiment, "specific", in reference to binding, means that to the extent that a molecule forms complexes with other molecules or complexes, it forms at least fifty percent of the complexes with the molecule or complex for which it has specificity. In one embodiment, the molecules or complexes have areas on their surfaces or in cavities giving rise to specific recognition between the two binding moieties. Exemplary of specific binding are antibody-antigen interactions, enzyme-substrate interactions, polynucleotide hybridizations and/or formation of duplexes, cellular receptor-ligand interactions, and so forth in other embodiments.

In one embodiment, the hyperpolarized noble element used in the biosensors utilized in the systems, methods and kits provided herein, is xenon, or in another embodiment, an isotope of xenon. An isotope of xenon, xenon-129, has non-zero nuclear spin (i.e., $I=\frac{1}{2}$) and therefore is a nucleus which, in one embodiment, is suited to study by nuclear magnetic resonance techniques. The nuclear magnetic resonance signals obtainable from $^{129}$Xe are extraordinarily sensitive to local environment and therefore very specific to environment.

In another embodiment, xenon interacts with proteins and lipids in plasma, which reduces the contribution of entropy ($T\Delta S|_{P,c}$=0.12, Table 1) relative to Xe binding of triacid-functionalized cryptophane in buffer.

In another embodiment, the $^{129}$Xe isotope is, in principle, suited to NMR uses, but is 26% naturally abundant and has a sensitivity relative to $^1$H (in conventional NMR) of $2.12\times10^{-2}$. In another embodiment, the resonance frequency of $^{129}$Xe spans an enormous range (0-300 ppm) over the gas and condensed phase, and is exceptionally sensitive to chemical environment. Its longitudinal relaxation time, $T_1$, is huge (practically at least 3000 s in the pure gas phase, and theoretically perhaps as long as 56 hrs at 1 atm, and is particularly sensitive to chemical environment, $O_2$ concentration, and the effects of other relaxation promoters. Its transverse relaxation time is also susceptible to relaxation promoters. In one embodiment, cleavage of the substrates disclosed in Table III, by their corresponding enzymes disclosed in Table III, creates a change in the chemical environment, thereby inducing a change in the $T_1$ relaxation time, as well as, in another embodiment, Trp acting as a relaxation promoter will increase the sensitivity to the change in the chemical environment, increasing the sensitivity of the biosensors used in the systems, methods and compositions described herein.

In one embodiment, the longitudinal and transverse relaxation times, $T_1$ and $T_2$, respectively, are also indicative of the environment surrounding the $^{129}$Xe atom, e.g., whether the atom is bound to a protein, dissolved in a lipid, or constrained in some other way, such as being complexed to monopropargyl-cryptophane-A coupled peptide in one embodiment. Thus, a combination of chemical shift, $T_1$, and $T_2$ data provide in another embodiment, a basis for distinguishing the presence or absence of the nucleus in a particular environment as well as for identifying the nature of the environment in question, such as the enzymatic activity of the enzymes described in Table III, whose cleavage of their corresponding substrates induces the chemical shift and changes in the $T_1$ and $T_2$ data.

Noble gases may be hyperpolarized for use in one embodiment, through any of various means known in the art, such as spin-exchange interactions with optically pumped alkali metal vapor. The optical pumping and spin-exchange can be performed in the absence of an applied magnetic field, or in another embodiment, using modest fields of about 1 G or larger. Pumping in the NMR magnet bore at fields of several Tesla is also possible. The maximum steady-state $^{129}$Xe nuclear polarization achievable depends in certain embodiments, on the time constant characterizing the spin exchange with the alkali metal and the time constant characterizing the relaxation ($T_1$) due, in an embodiment, to contact with the surfaces of the pumping cell. In another embodiment, with $T_1$ of 20 min, polarizations of 20-40% are practicable, and polarizations of 70% or more are attainable in other embodiments. The long $T_1$ of the gas allows in one embodiment for samples to be manipulated, even stored as Xe ice, and transported on time scales of hours or even days, without serious loss of magnetization.

In one embodiment, the biosensors provided hereinabove, are synthesized according to the methods provided herein. Accordingly, provided herein is a method of synthesizing an enzyme-responsive biosensor, comprising the steps of: alkylating cyclotriguaiacylene with a [3-propargyloxy-4-(2-iodoethoxy)phenyl]methanol linker, in the presence of cesium carbonate, obtaining 12-[2-(4-hydroxymethyl-2-propargyloxyphenoxy)ethoxy]-3,8,13-trimethoxy-10,15-dihydro-5H-tribenzo[a,d,g]cyclononene-2,7-diol; alkylating the resulting 12-[2-(4-hydroxymethyl-2-propargyloxyphenoxy)ethoxy]-3,8,13-trimethoxy-10,15-dihydro-5H-tribenzo[a,d,g]cyclononene-2,7-diol with two [4-(2-iodoethoxy)-3-methoxyphenyl]methanol linkers in the presence of $Cs_2CO_3$, yielding {3-propargyloxy-4-[2-(3,8,13-trimethoxy-7,12-bis[2-(4-hydroxymethyl-2-methoxyphenoxy)ethoxy]-10,15-dihydro-5H-tribenzo-[a,d,g]cyclononen-2-yloxy)ethoxy]phenyl}methanol; cyclizing the obtained {3-propargyloxy-4-[2-(3,8,13-trimethoxy-7,12-bis[2-(4-hydroxymethyl-2-methoxyphenoxy)ethoxy]-10,15-dihydro-5H-tribenzo-[a,d,g]cyclononen-2-yloxy)ethoxy]phenyl}methanol, in the presence methanol and perchloric acid, yielding monopropargyl-cryptophane-A; coupling the obtained monopropargyl-cryptophane-A, using Cu(I) as a catalyst, with a resin-associated azido-peptide, wherein the peptide is a substrate of the enzyme; cleaving the resin from the monopropargyl-cryptophane-A coupled resin-associated peptide; and complexing a hyperpolarized noble element with the monopropargyl-cryptophane-A coupled peptide, whereby said hyperpolarized noble element undergoes a chemical shift in response to enzymatic cleavage of the peptide.

In one embodiment, the enzyme of which the resin-associated peptide is a specific substrate of any one of the enzymes in Table III, such as MMP-1 in one embodiment, or MMP-2, MMP-3, MMP-7, MMP-8, MMP-9, MMP-11, MMP-13, MMP-14, MMP-17, MMP-26, Gelatinase A/Gelatinase B, Caspase-1, Caspase-2, Caspase-3, Caspase-4, Caspase-5, Caspase-6, Caspase-7, Caspase-8 and Caspase-9 and the like in other embodiments. In another embodiment, the enzyme of which the resin-associated peptide is any protease.

In one embodiment, the biosensors described hereinabove, synthesized by the methods described herein, are used in the screening and assay methods described herein. In one embodiment, provided herein is a method of analyzing the activity of a matrix metalloproteinase (MMP), caspases or their combination in a biological sample, comprising the step of contacting the metalloproteinase, caspase or their combination with biosensor responsive to the MMP's or caspases or their combination, comprising: a hyperpolarized noble element complexed with a monopropargyl-cryptophane-A coupled peptide, wherein the peptide is a substrate, specific to said MMP, or caspase and whereby cleavage of the substrate by the MMP, caspase or other similar enzymes induces change in the molecular environment of the noble element resulting in a chemical shift detectable by NMR; and analyzing the chemical shift in said element, whereby a chemical shift indicates activity of the MMP, caspase or similar enzyme. In another embodiment, other enzymes may be used. These are in one embodiment kinases, esterases, proteases, and the like. In one embodiment, the biosensors provided herein are synthesized specifically for a given enzyme, regardless of whether it is disclosed in Table III. A person skilled in the art would recognize that so long as a peptide sequence can successfully be operably coupled to the monopropargyl-cryptophane-A, using the synthesis methods provided herein, the resulting biosensor is within the scope of the embodiments provided herein.

In one embodiment, the biological sample taken from the subject is blood, or sputum, sera, urine, mucosa, feces, epidermal sample, skin sample, cheek swab, sperm, semen, amniotic fluid, cultured cells, bone marrow sample, chorionic villi, primary tumor biopsies, metastases biopsies, diffuse tumor biopsies, or a combination thereof in other embodiments.

In one embodiment, provided herein is a method of analyzing the activity of a matrix metalloproteinase in a biological sample comprising the step of contacting the biological sample with a matrix metalloproteinase-responsive biosensor comprising a hyperpolarized noble element complexed with a monopropargyl-cryptophane-A coupled peptide, wherein the peptide is a substrate, specific to said matrix metalloproteinase and whereby cleavage of the substrate by the matrix metalloproteinase induces change in the chemical environment of the noble element resulting in a chemical shift detectable by NMR; and analyzing the chemical shift in said element, whereby a chemical shift indicates activity of said metalloproteinase.

In another embodiment, provided herein is a method of analyzing the activity of a caspase in a biological sample comprising the step of contacting the biological sample with a caspase-responsive biosensor comprising a hyperpolarized noble element complexed with a monopropargyl-cryptophane-A coupled peptide, wherein the peptide is a substrate, specific to said caspase and whereby cleavage of the substrate by the caspase induces change in the chemical environment of the noble element resulting in a chemical shift detectable by NMR; and analyzing the chemical shift in said element, whereby a chemical shift indicates activity of said caspase.

In one embodiment, the matrix metalloproteinases and caspases whose activity is sought to be detected using the systems, methods and kits provided herein, and their corresponding specific substrates, are shown in Table III.

In one embodiment, the biosensors provided hereinabove, are used in the kits provided herein, which are utilized in another embodiment, to carry out the methods provided herein. In one embodiment, provided herein is a kit for screening for a matrix metalloproteinase activity in a biological sample, comprising a biosensor responsive to said matrix metalloproteinase, said biosensor comprising a hyperpolarized noble element complexed with a monopropargyl-cryptophane-A coupled peptide, wherein the peptide is a substrate, specific to said detected enzyme and whereby cleavage of the substrate by the enzyme induces change in the chemical environment of the noble element resulting in a chemical shift detectable by NMR; and instructions for use. In another embodiment, provided herein is a kit for screening for caspase activity in a biological sample, comprising a biosensor responsive to said caspase, said biosensor comprising a hyperpolarized noble element complexed with a monopropargyl-cryptophane-A coupled peptide, wherein the peptide is a substrate, specific to said caspase and whereby cleavage of the substrate by the caspase induces change in the chemical environment of the noble element resulting in a chemical shift detectable by NMR; and instructions for use.

Early detection represents one of the most promising approaches to reducing the growing cancer burden. In one embodiment, the early detection of neoplastic tissue, has a key role in the prognosis of cervical and breast cancer, and is more important in the control of colorectal, prostate and lung cancer. In one embodiment, the biosensors used in the kits and methods provided herein, may be injected to the organs or tumors associated with the cervix, breast, prostate, lung and colon and following imaging modality, will enable detection at an early stage, due to the specific design available through the synthesis methods provided herein, for enzymes specifically involved in early stage cancer. In another embodiment, biosensors may also be made orally available, where the hyperpolarized xenon is delivered separately, by inhalation or injection.

For example, MMP-2 overexpression serves as a predictor of shortened cancer-related survival in NSCLC without lymph node involvement (P=0.005, relative risk, 2.6). In another embodiment, MMP-2 overexpression predicts a poor prognosis in early-stage NSCLC. Using the biosensors and the methods described herein, a biosensor that is response-specific to MMP-2 is prepared, using Pro-Leu-Gly-Leu-Trp-Ala-D-Arg-$NH_2$ (SEQ ID NO. 3), as the substrate for the enzyme and detecting therewith early activity of MMP-2. In one embodiment, the presence of tryptophan in the substrate, will increase the sensitivity of the biosensor, allowing early detection of MMP-2 activity. In one embodiment, contacting the lungs with the biosensors described in the embodiments herein, in combination with semi-continuous xenon-inhalation allows for the early detection of MMP-2 in the lungs without the need of biopsy.

In another embodiment, MMP-14 is the factor most significantly associated with the outcome of breast cancer and is an independent factor of poor overall survival when adjusted for clinical prognostic factors, excluding ancillary markers. Using the biosensors and the methods described herein, a biosensor that is response-specific to MMP-14 is prepared, using Pro-Leu-Ala-Cys(p-OMeBz)-Trp-Ala-Arg(Dpa)-$NH_2$ (SEQ ID NO. 13), as the substrate for the enzyme and detecting therewith early activity of MMP-14. In one embodiment, the presence of tryptophan in the substrate, will increase the sensitivity of the biosensor, allowing early detection of MMP-14 activity and improved prognosis thereby. In another embodiment, injection of the biosensors as described in the embodiments herein, allows the early detection of MMP-14 activity, using MRI imaging, without the need to biopsy the tissue.

A person skilled in the art, would recognize that the kits provided herein may be used to specifically classify cancer stages in various tissues, depending on the enzyme expression in each stage, and likewise be used for the screening of candidate drugs for inhibiting or modulating the activity of the involved enzymes.

In one embodiment, provided herein is a library of chemical shifts, $T_1$, $T_2$ data or their combination, whereby the data is specific for each enzyme, its specific substrate and their values as affected by the biological sample used and a pathology related to the enzymatic activity in that particular biological sample. According to this aspect of the invention, and in one embodiment, instructions enclosed in the kits provided herein may provide the chemical shift observed in a lung of a to subject when the enzyme is MMP-7 and the substrate is Arg-Lys-Arg-Pro-Leu-Ala-Leu-Trp-Arg-Ser-Arg-Lys-$NH_2$ (SEQ ID NO. 7) and whereby the subject exhibits symptoms associated with lung cancer.

In one embodiment, the kits provided herein, may include a combination of biosensors that is specific for a pathology sought to be screened or diagnosed. These kits will include in another embodiment the optimal combination of biosensors and their corresponding specific substrates and the expected chemical shifts and changes in the $T_1$ and $T_2$ relaxation times. These kits may include in one embodiment, any combination of the enzymes shown in Table III and their corresponding substrates.

In one embodiment, the biosensors provided herein are used in the screening methods provided. In one embodiment, provided herein is a method for screening for a candidate agent capable of modulating the activity of an enzyme in a biological sample, comprising the step of contacting a first portion of the biological sample with a biosensor sensitive to the enzyme, said biosensor comprising a hyperpolarized noble element complexed with a monopropargyl-cryptophane-A coupled peptide, wherein the peptide is a substrate, specific to said detected enzyme and whereby cleavage of the substrate by the enzyme induces a change in the chemical environment of the noble element resulting in a detectable chemical shift; contacting a second portion with the candidate agent screened; contacting the second portion with the same biosensor; and comparing the detected chemical shift, whereby a change in the chemical shift between the first and second portions indicates an agent capable of modulating the activity of the enzyme.

In another embodiment, the candidate agent sought to be screened using the screening methods provided herein and utilizing the biosensors provided herein, is selected using rational drug design (RDD).

In one embodiment, RDD includes not only knowing or predicting the conformation of a desired protein, but also being able to control and predict the conformation of a drug peptide that is to interact with the target protein. Therefore the biosensors described herein may use the peptide coupled to the monopropargyl-cryptophane-A as the candidate peptide and evaluate its efficacy as an agonist, antagonist or ligand to any enzyme sought to be modulated.

In one embodiment, the term "antagonist" or "antagonist ligand", refers to a compound that selectively inhibits or decreases function of an enzyme sought to be modulated or normal regulatory expression or function of other proteins affected by the enzyme sought to be modulated. An antagonist can act in other embodiments by any antagonistic mechanism, such as by binding to an enzyme sought to be modulated or to products regulated by the enzyme sought to be modulated, thereby inhibiting binding between an enzyme sought to be modulated and its regulated products. An antagonist to an enzyme sought to be modulated can also act indirectly, for example, by modifying or altering the native conformation of the enzyme sought to be modulated or its regulated products. The methods described herein can advantageously be used to identify an antagonist to the enzyme sought to be modulated that acts through any antagonistic mechanism.

Initially a potential drug, or candidate antagonist ligand could be obtained by screening a random peptide library produced by recombinant bacteriophage in one embodiment, [Scott and Smith, Science, 249:386-390 (1990); Cwirla et al., Proc. Natl. Acad. Sci., 87:6378-6382 (1990); Devlin et al., Science, 249:404-406 (1990)] or a chemical library. An agent thus selected in another embodiment, could then be systematically modified by computer modeling programs until one or more promising potential drugs are identified.

In one embodiment, computer modeling allows the selection of a finite number of rational chemical modifications, as opposed to the countless number of essentially random chemical modifications that could be made, any one of which might lead to a useful drug. Each chemical modification requires additional chemical steps, which while being reasonable for the synthesis of a finite number of compounds, may become overwhelming if all possible modifications are needed to be synthesized. Thus through the use of a three-dimensional structural analysis and computer modeling, a large number of these compounds can be rapidly screened on the computer monitor screen, and a few likely candidates can be determined without the laborious synthesis of numerous compounds.

Once a potential drug or antagonist is identified, in one embodiment it either can be selected from a library of chemicals that are commercially available from most large chemical companies including Merck, Glaxo Welcome, Bristol Meyers Squib, Monsanto/Searle, Eli Lilly, Novartis and Pharmacia UpJohn, or in another embodiment the potential drug may be synthesized de novo. As mentioned herein, the de novo synthesis of one or even a relatively small group of specific compounds is reasonable experimentation for rational drug design.

RDD has been revolutionized by the introduction of high throughput synthesis and combinatorial chemistry which afford collections and mixtures of large numbers of synthetic compounds for the purpose of screening for biological activity. Such large mixtures and pools of compounds pose significant challenges for the bioassay and analytical scientist. The analytical challenge is two-fold: separation of the active component of a mixture, and the identification of its structure. A variety of separation methods are available, including LC, HPLC, and CE. However, from the standpoint of separating biologically active components from a mixture of one or more targets with a combinatorial library, it necessitates the use and development of methods that select for and separate the complex (usually noncovalent) between the ligands and the target. In one embodiment, the potential sensitivity of the biosensors provided herein, makes them an ideal system for use in RDD.

In one embodiment, the methods of producing the biosensors provided herein, are used in the compositions and methods described herein for detection and diagnosis of cancer in a subject as described herein. Accordingly and in one embodiment, provided herein is an in-vivo cancer cell detection system comprising: a detectably labeled biosensor wherein said biosensor comprises: a hyperpolarized noble element; complexed with a monopropargyl-cryptophane-A coupled peptide, wherein the peptide is capable of binding an integrin and whereby cellular uptake of the biosensor bound to the integrin by the cancer cell is detectable.

In another embodiment, the term "Integrins", refers to a family of transmembrane adhesion receptors that are principal mediators of cell attachment, migration, differentiation, and survival. Structurally, integrins are heterodimeric receptors that are composed of large extracellular domains, one transmembrane helix, and small intracellular domains for each subunit. These receptors consist of an $\alpha$- and a $\beta$-subunit, which associate non-covalently in defined combinations. To date, 18 $\alpha$-subunits and 8 $\beta$-subunits have been identified, which associate selectively to form at least 24 integrins. In certain embodiments, integrins transduce messages via various signaling pathways and influence proliferation and apoptosis of tumor cells, as well as of activated endothelial cells. Unique combination of integrins on the cell surface allows in other embodiments, for cells to recognize and then respond to a variety of extracellular ligands. Integrin $\alpha_v\beta 3$ is a prominent member of integrin family. It has been implicated in the pathophysiology of malignant tumors where it is required for tumor angiogenesis and is highly expressed on both endothelial cells in neovasculature and highly aggressive human carcinomas. In another embodiment, integrin $\alpha_v\beta 3$ mediates adhesion of tumor cells on a variety of extracellular matrix proteins, allowing these cells to migrate during invasion and extravasation. In breast cancer, $\alpha_v\beta 3$ characterizes the metastatic phenotype, as this integrin is upregulated in invasive tumors and distant metastases. The $\alpha_v\beta 3$ receptor binds to a variety of extracellular matrix proteins, including fibrinogen, fibronectin, osteopontin, thrombospondin, and vitronectin largely through interaction with the Arg-Gly-Asp (RGD) tripeptide sequence. In one embodiment, the peptide employed in the biosensors used in the methods and compositions described herein, is a di-, tri-, tetra-RGD peptide or a combination thereof.

Accordingly and in one embodiment, provided herein is an in-vivo cancer cell detection system comprising: a detectably labeled biosensor wherein said biosensor comprises: a hyperpolarized noble element; complexed with a monopropargyl-cryptophane-A coupled peptide, wherein the peptide is capable of binding an integrin and whereby cellular uptake of the biosensor bound to the integrin by the cancer cell is detectable, wherein the peptide is tetra-RGD (SEQ ID. No. 30). In another embodiment, the peptide is tri-RGD (SEQ ID. No. 32). In another embodiment, the peptide is di-RGD (SEQ ID. No. 31).

In another embodiment, integrin $\alpha_v\beta3$ is implicated in multiple aspects of tumor progression, metastasis, and osteoclast bone resorption. Many tumors have high expression of $\alpha_v\beta3$, and this expression correlates with tumor progression in melanoma, glioma, ovarian, prostate, breast cancer, as well as other cancers. In another embodiment, the $\alpha_v\beta3$ receptor is used as a therapeutic target for novel anticancer agents. Accordingly, the methods provided herein can be readily used to evaluate the efficacy of drugs targeting the $\alpha_v\beta3$ receptor.

Likewise and in another embodiment, provided herein is a method of imaging a cancer in vivo in a subject, comprising the step of contacting a suspected cancer cell with a composition comprising a detectably labeled biosensor wherein said biosensor comprises: a hyperpolarized noble element; complexed with a monopropargyl-cryptophane-A coupled peptide, wherein the peptide is capable of binding an integrin expressed on the surface of the pancreatic or lung cell and analyzing the change in fluorescent intensity of the suspected cell before and after administration of the composition, whereby increase in fluorescent intensity, indicates the cell is cancerous. In one embodiment, the increase in expression of $\alpha_v\beta3$ correlates with progression of the cancer, or in another embodiment with onset of metastases. In certain embodiments, the methods of imaging cancer in-vivo described herein are used for staging cancer.

In one embodiment, the di-, tri- or tetra-RGD peptides used in the compositions and methods described herein, are capable of binding integrins other than the $\alpha_v\beta3$ integrin and the methods of imaging cancer in-vivo in a subject described herein, or in another embodiment, the methods of evaluating the efficacy of cancer drug therapy described herein, or in another embodiment, the methods of detecting a cancer cell in-vivo, are effected through interactions with non-$\alpha_v\beta3$ integrins. In one embodiment, the integrins are $\alpha1\beta1$, $\alpha5\beta1$, $\alpha v\beta3$, and $\alpha6\beta4$ (coupled to the Ras-extracellular signal-regulated kinase (ERK) signaling pathway by the adaptor protein Shc), $\beta_{1C}$ integrin (an unspliced form of the integrin $\beta_1$ subfamily), and others that are now known or later discovered, whose expression or function in cells enables the modulation of the function of those integrins.

In another embodiment, the term "labeled" refers to the attachment of a moiety, capable of detection by spectroscopic, radiologic or other methods, to the biosensors provided herein. In one embodiment, the label used in the methods and compositions provided herein, is Cy3 dye. In another embodiment, the label is dinitrophenyl, fluorescein and derivatives thereof, rhodamine, derivatives of rhodamine, phycoerythrin, phycocyanin, allophycocyanin, o-phthaldehyde and fluorescamine, Texas red, Rhodamine green, Oregon green, Cascade blue, phycoerythrin, Cy3, Cy5, Cy2, Cy7, coumarin, infrared 40, MR 200, IRD 40, green fluorescent protein and combinations thereof.

In one embodiment, the label used in the methods described herein is an NIR label such as Alexa dyes in certain embodiments, or any fluorophore now known or later developed, having an emission spectra between about 700 to about 900 nm.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

Reagents

Organic reagents and solvents were used as purchased from the following commercial sources: Sigma-Aldrich, 3,4-dihydroxybenzaldehyde, sodium hydride, dimethyl sulfoxide (DMSO), dimethylformamide (DMF), methanol, triisopropylsilane (TIS), 2,6-lutidine, piperidine; Acros, propargyl bromide, dibromoethane; Fisher, tris(hydroxymethyl)aminomethane (Tris), calcium chloride, sodium chloride, copper (II) sulfate, sodium borohyride, sodium iodide, potassium carbonate, trifluoroacetic acid (TFA), diethyl ether ($Et_2O$), acetone, perchloric acid (60%); Alfa Aesar, cesium carbonate; Novabiochem, Fmoc-Lys(Boc)-Wang resin (0.67 mmol/g, 100-200 mesh), 2-(1H-benzotriazole-1-yl)-1,1,3,3-tetramethyluronium hexafluorophosphate (HBTU), N-methylmorpholine (0.4 M), and Fmoc-protected amino acids Fmoc-L-Lys(Boc)-OH, Fmoc-L-Arg(Pbf)-OH, Fmoc-L-Ser(tBu)-OH, Fmoc-L-Ala-OH, Fmoc-L-Leu-OH, Fmoc-L-Pro-OH, Fmoc-L-Trp-OH); BIOMOL International LP, MMP-7 (recombinant, catalytic domain). For biological assays, all solutions were prepared using deionized water purified by Ultrapure Water Systems. The standard buffer is defined herein as 50 mM Tris, 5 mM $CaCl_2$, 300 mM NaCl, pH 7.5.

General Methods

All air- and moisture-sensitive reactions were performed under dinitrogen with glassware oven-dried and then flamed under partial vacuum. Peptides were generated using a Protein Technologies PS3 Peptide Synthesizer. HPLC analysis was performed on an Agilent 1100 system equipped with a quaternary pump and diode array detector using a Zorbax C-8 semi-preparative (9.4×250 mm, 5 microns) or analytical column (4.6×150 mm, 5 microns). The gradient eluent was composed of two solvents: 0.1% aqueous TFA (solvent A) and a 0.1% solution of TFA in $CH_3CN$ (solvent B). Mass identification of all peptide-containing compounds was performed by the Wistar Institute Proteomics Facility using an Applied Biosystems Voyager 6030 MALDI-TOF mass spectrometer. $^1H$ (499.90 MHz) and $^{13}C$ (124.98 MHz) NMR spectra were obtained on a Brüker 500 MHz Fourier transform spectrometer at the University of Pennsylvania NMR facility, and recorded in $CDCl_3$ unless otherwise noted. The $^1H$ spectra were referenced to residual CHCl$_3$ (7.27 ppm). The $^{13}$C spectra were referenced to the central line of CDCl$_3$ (77.23 ppm). $^{13}$C and $^1$H chemical shifts (δ) are given in parts per million (ppm) and reported to a precision of ±0.01 ppm. Proton coupling constants (J) are given in Hz and reported to a precision of ±0.1 Hz. Column chromatography was performed using 60 Å pore size, 40-75 μm particle size silica gel from Sorbent technologies. Thin layer chromatography (TLC) was performed using silica gel plates with UV light as the detection method.

Peptide Synthesis and Purification

Peptides N$_3$—CH$_2$CH$_2$—CONH$_2$-RKRPLALWRSRK (SEQ ID NO. 33) (hereinafter denoted as 1), N$_3$—CH$_2$CH$_2$—CONH$_2$-RKRPLA (SEQ ID NO. 34) (hereinafter denoted as 2), and LWRSRK (SEQ ID NO. 35) 3 were synthesized using standard Fmoc amino acid protection chemistry on Fmoc-Lys (Boc)-Wang resin (0.1 mmol scale). Complete synthetic details are included in the Supporting Information. For purification of peptides 1, 2, and 3, the following gradient was run: time 0, A/B=90/10; 0-30 min, linear increase to A/B=60/40; 30-32 min, linear change to A/B=20/80; 32-42 min, A/B=20/80. MALDI calculated for peptide 1 C$_{73}$H$_{127}$N$_{30}$O$_{15}$ (M+H$^+$), 1664.01. found, 1663.72. MALDI calculated for peptide 2 C$_{35}$H$_{65}$N$_{16}$O$_8$ (M+H$^+$), 836.95. found, 836.43. MALDI calculated for peptide 3 C$_{38}$H$_{64}$N$_{14}$O$_8$ (M+H$^+$), 845.02. found, 845.28.

Organic Synthesis

Figure 2:
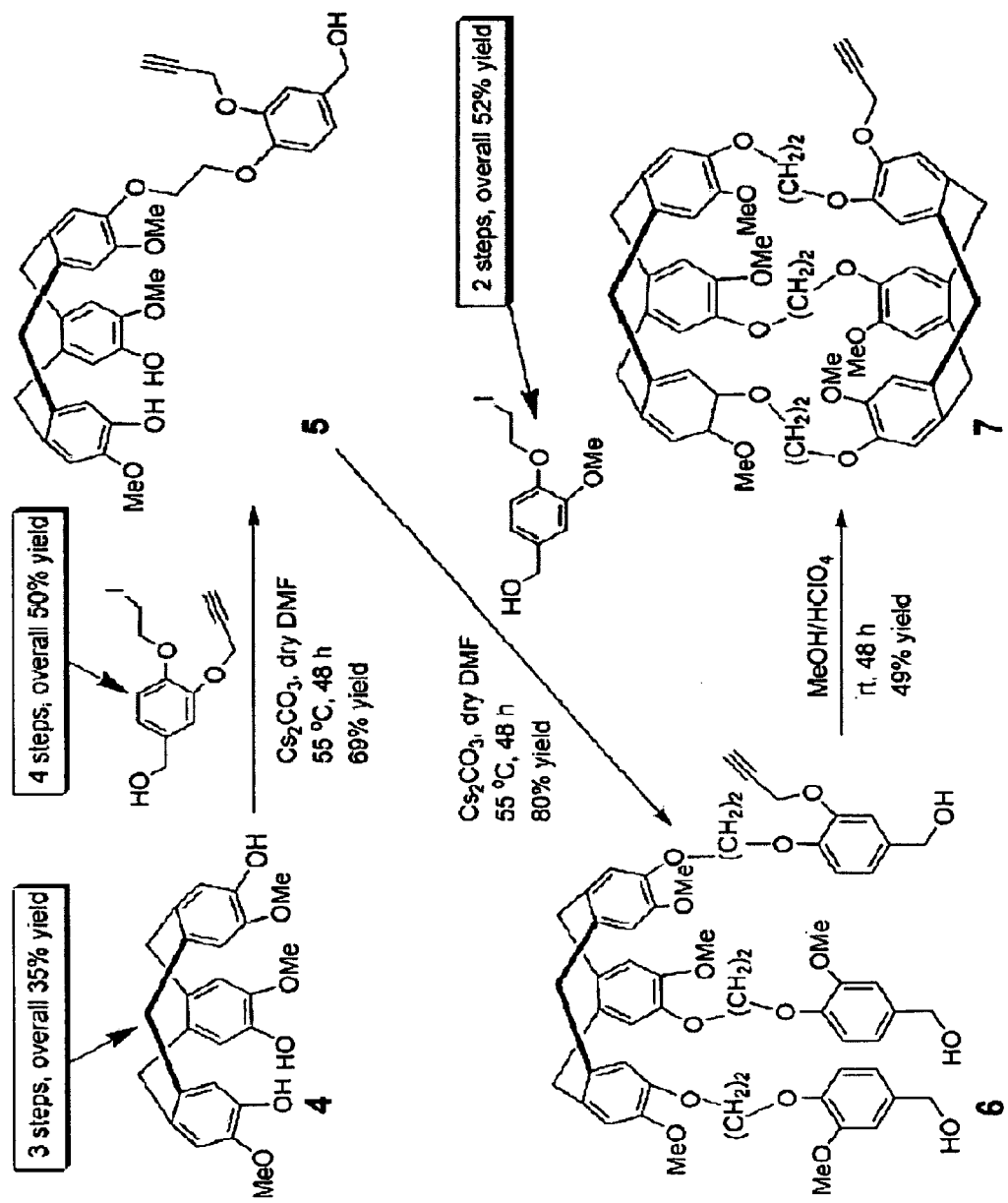
FIG. 2 shows the initial steps of a 12-step non-linear synthesis of monopropargyl-cryptophane-A.

Scheme 1 (FIG. 2) shows the synthetic route to monopropargyl-functionalized cryptophane-A 7.[42-45] The synthetic details for this compound are described in this section. The cyclotriguaiacylene, [3-propargyloxy-4-(2-iodoethoxy)phenyl]methanol linker, and [4-(2-iodoethoxy)-3-methoxyphenyl]methanol linker were prepared based on reported syntheses of similar compounds.[42-48] Detailed synthetic procedures for these compounds are provided in the Supporting Information.

12-[2-(4-hydroxymethyl-2-propargyloxyphenoxy)ethoxy]-3,8,13-trimethoxy-10,15-dihydro-5H-tribenzo[a,d,g]cyclononene-2,7-diol (5)

To a two-neck flask with nitrogen inlet, cyclotriguaiacylene 4 (408 mg, 1 mmol, 1 equiv) and Cs$_2$CO$_3$ (975 mg, 3 mmol, 3 equiv) were added into anhydrous DMF (30 mL). The mixture was stirred at room temperature for 30 min. [3-propargyloxy-4-(2-iodoethoxy)phenyl]methanol (331 mg, 1 mmol, 1 equiv) was then added in one portion and the resulting mixture was heated at 55° C. for 48 h under N$_2$ atmosphere. The mixture was poured into water (200 mL) and the product was extracted with ethyl acetate. The combined organic extracts were concentrated to 200 mL and washed subsequently with NaOH (3×200 mL), water (200 mL) and brine (5×200 mL). The organic layer was dried over MgSO$_4$, filtered and the solvent was removed under vacuum. The crude product as a brownish solid was chromatographed on a silica gel column (eluent: 1% to 3% methanol in CH$_2$Cl$_2$) to give pure product as a white solid (420 mg, yield: 69%). $^1$H NMR δ=6.98 (s, 1H), 6.90 (s, 1H), 6.84 (t, J=5.8, 3H), 6.77 (s, 1H), 6.72 (d, J=2.3, 2H), 4.64 (two doublets, J=13.7, J=14.3, 3H), 4.58 (d, J=2.3, 2H, —OCH$_2$C≡CH), 4.54 (s, 2H, —CH$_2$OH), 4.30 (m, 4H, —OCH$_2$CH$_2$O—), 3.76 (s, 3H, —OCH$_3$), 3.75 (s, 3H, —OCH$_3$), 3.66 (s, 3H, —OCH$_3$), 3.44 (two doublets, J=13.7, J=13.5, 3H), 2.41 (t, J=2.3, 1H, —C≡CH). $^{13}$C NMR δ=148.59, 148.42, 147.41, 146.62, 145.40, 144.19, 144.17, 134.39, 133.28, 132.63, 132.30, 132.10, 131.41, 131.32, 121.14, 116.80, 115.79, 115.67, 114.61, 114.29, 113.84, 112.32, 78.91, 75.92, 68.18, 67.84, 65.08, 56.99, 56.25, 56.16, 56.10, 3644, 36.34, 36.30. HRMS calculated for C$_{36}$H$_{36}$O$_9$ (M+Na$^+$), 635.2257; found, 635.2232.

{3-propargyloxy-4-[2-(3,8,13-trimethoxy-7,12-bis[2-(4-hydroxymethyl-2-methoxyphenoxy)ethoxy]-10,15-dihydro-5H-tribenzo-[a,d,g]cyclononen-2-yloxy)ethoxy]phenyl}methanol (6)

According to the procedure for the synthesis of 5, compound 6 (700 mg, yield: 80%) was obtained from the reaction of 5 (560 mg, 0.91 mmol, 1 equiv), [4-(2-iodoethoxy)-3-methoxyphenyl]methanol (800 mg, 2.7 mmol, 3 equiv) and Cs$_2$CO$_3$ (1.2 g, 3.7 mmol, 4 equiv) in anhydrous DMF (20 mL). $^1$H NMR δ=7.01-6.80 (m, 15H), 4.73 (d, J=13.7, 3H), 4.61 (m, 8H), 4.38 (m, 4H, —OCH$_2$CH$_2$O—), 3.75 (s, 3H, —OCH$_3$), 3.74 (s, 3H, —OCH$_3$), 3.69 (s, 9H, —OCH$_3$), 3.53 (d, J=13.7, 3H, —OCH$_3$), 2.45 (d, J=2.3, 1H, —C≡CH). $^{13}$C NMR δ=149.73, 148.61, 148.55, 148.50, 148.31, 147.52, 147.51, 147.50, 146.89, 146.88, 146.82, 134.74, 133.21, 133.14, 131.99, 121.13, 119.54, 116.73, 116.60, 116.59, 114.59, 114.55, 113.86, 111.05, 78.90, 75.97, 68.17, 67.98, 67.80, 65.28, 65.08, 56.96, 56.27, 56.23, 55.90, 36.56. HRMS calculated for C$_{56}$H$_{60}$O$_{15}$ (M+Na$^+$), 995.3829; found, 995.3808.

Monopropargyl-Cryptophane-A (7)

Methanol (150 mL) was added to a stirred solution of 6 (90 mg, 0.09 mmol) in CH$_2$Cl$_2$ (10 mL). Perchloric acid (150 mL) was then added dropwise into the cloudy solution at 0° C. The reaction was allowed to warm to rt and stirred slowly for 48 h under N$_2$. The reaction mixture was diluted by CH$_2$Cl$_2$ (300 mL) and neutralized by 1 M NaOH solution at 0° C. The CH$_2$Cl$_2$ and aqueous phases were separated and the aqueous layer was extracted with CH$_2$Cl$_2$ (3×250 mL). The combined organic extracts were concentrated to 300 mL and washed with NaHCO$_3$ solution and brine several times. The solution was filtered and dried over MgSO$_4$. After removal of the solvent under vacuum, the brownish residue was chromatographed on a silica gel column (eluent: 1% to 3% methanol in CH$_2$Cl$_2$) to give pure product as a light yellowish solid (42 mg, yield: 49%). $^1$H NMR δ=6.90 (s, 2H), 6.78 (s, 2H), 6.76 (s, 4H), 6.69 (t, J=5.0, 4H), 4.72 (dd, J$_1$=3.2, J$_2$=21.6, 3H), 4.61 (d, J=18.2, 5H), 4.18 (m, 12H, —OCH$_2$CH$_2$O—), 3.81 (s, 5H, —OCH$_3$), 3.80 (s, 5H, —OCH$_3$), 3.78 (s, 5H, —OCH$_3$), 3.42 (d, J=19.2, 6H), 2.70 (t, J=3.2, 1H, —C≡CH). $^{13}$C NMR δ=150.46, 150.43, 150.28, 148.57, 148.00, 147.39, 147.27, 135.06, 134.88, 134.83, 134.76, 134.48, 133.89, 132.44, 132.29, 132.24, 132.16, 122.30, 122.19, 121.96, 121.30, 121.19, 121.14, 118.08, 114.69, 114.48, 114.40, 114.33, 79.65, 76.82, 70.27 (—OCH$_2$CH$_2$O—), 70.17 (—OCH$_2$CH$_2$O—), 69.92 (—OCH$_2$CH$_2$O—), 69.89 (—OCH$_2$CH$_2$O—), 58.01 (—OCH$_2$C≡CH), 56.83 (—OCH$_3$), 56.46 (—OCH$_3$), 56.38 (—OCH$_3$), 56.26 (—OCH$_3$), 36.88 (—CH$_2$—). HRMS calculated for C$_{56}$H$_{54}$O$_{12}$ (M+Na$^+$), 941.3513; found, 941.3541.

[3+2] Cycloaddition

Figure 5:
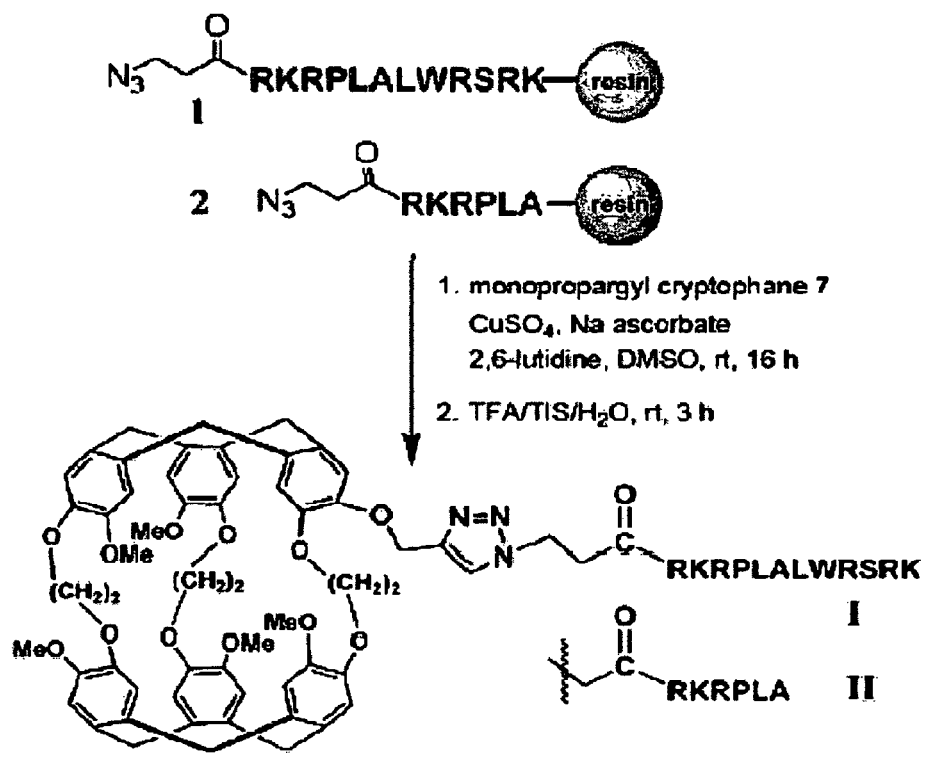
FIG. 5 shows the synthesis of biosensors I and II with the final step involving Cu(I)-catalyzed cycloaddition of monopropargyl-cryptophane-A to azidopeptide on solid support. Reaction of 1 or 2 with 7, followed by TFA cleavage and HPLC purification, yielded I and II in 80-92% yield.

As shown in Scheme 2 (FIG. 5), a solution of copper(II) sulfate (0.006 mmol, 0.5 equiv) was added to the azidopeptide-modified resin (20 mg, maximum 0.0124 mmol azidopeptide 1 or 2, 1 equiv) followed by 2,6-lutidine (2.78 μL, 0.024 mmol, 2 equiv), sodium ascorbate (0.018 mmol, 1.5 equiv), and monopropargyl-cryptophane-A 7 (21 mg, 0.024 mmol, 2 equiv). The suspension was degassed with gentle N$_2$ flow and stirred at rt for 16 h. The resin was transferred to a fritted reaction vessel and washed sequentially with CH$_2$Cl$_2$, MeOH, water, and 1:1 MeOH:CH$_2$Cl$_2$. The resin was then dried under vacuum.

Cleavage of the conjugate product from the resin was accomplished by treating the dried resin at rt for 3 h with a mixture of TFA, water, thioanisole, phenol, ethanedithiol and triisopropylsilane (81.5/5/5/5/2.5/1) for peptide containing unprotected Trp and with TFA, water, and triisopropylsilane (95/2.5/2.5) for peptide without the Trp residue. The resin was removed by filtration and rinsed with minimal TFA. Addition of anhydrous $Et_2O$ to the filtrate gave a white solid precipitate, which was washed with anhydrous $Et_2O$, collected by centrifugation and dried under vacuum to yield crude product. The products I and II were purified by HPLC with the following gradient: time 0, A/B=75/25; 0-30 min, linear increase to A/B=45/55; 30-32 min, linear change to A/B=20/80; 32-42 min, A/B=20/80. MALDI calculated for intact biosensor I $C_{129}H_{181}N_{30}O_{27}$ (M+H$^+$), 2582.37; found, 2582.42. MALDI calculated for cleaved biosensor II $C_{91}H_{119}N_{16}O_{20}$ (M+H$^+$), 1756.31; found, 1756.64.

Enzymatic Assay, Monitored by HPLC

At rt, an aliquot (2 μL) of active MMP-7 (0.454 μg/μL) was added into 0.998 mL of a freshly prepared solution of biosensor I at a known concentration in standard buffer. The extinction coefficient of I, $\epsilon$=15,000 M$^{-1}$ cm$^{-1}$ at 280 nm in water, was determined from a solution containing the weighed sample. At approximately 3 min intervals, 70 μL aliquots were removed from the reaction mixture and immediately quenched with 30 μL of a 40 mM EDTA solution. Each aliquot was analyzed by HPLC with the gradient: time 0, A/B=75/25; 0-30 min, linear increase to A/B=45/55; 30-32 min, linear change to A/B=20/80; 32-42 min, A/B=20/80. The retention times for I and II were 15.6 min and 17.9 min, respectively. The enzyme activity was determined from the initial rate of increase in the concentration of cleaved sensor II, during the consumption of the first 10-15% of substrate I. The absorbance at 280 nm of the growing peak at 17.9 min was integrated and compared for each time point. Initial velocities were measured at substrate I concentrations of 6, 16, 28, 38, 48, 74 and 100 μM.

The $k_{cat}/K_M$ value for all peptide substrates was calculated based on the Michaelis-Menten equation (Equation 1) after fitting the activity data at varying substrate concentrations with a non-linear regression curve:

$$v = \frac{[E]_0[S]k_{cat}}{K_M + [S]} \quad (1)$$

where [E]$_0$ and [S] were the total enzyme and substrate concentrations in solution, $k_{cat}$ was the rate of product formation by the enzyme-substrate complex, and $K_M$ was the Michaelis constant, which gave the concentration of substrate at which the reaction occurred at half of the maximum rate, $V_{max}$.

For the azidopeptide substrate 1, enzyme activity was determined similarly by HPLC with the gradient: time 0, A/B=90/10; 0-30 min, linear increase to A/B=60/40; 30-32 min, linear change to A/B=20/80; 32-42 min, A/B=20/80. Peak areas were monitored for the intact substrate 1 and cleaved hexapeptide product 3 at retention times of 17.0 and 10.3 min, respectively. Initial velocities were measured at substrate 1 concentrations of 6, 50, 100, and 870 μM.

Fluorescence Spectroscopy and Fluorometric Enzymatic Assay

Fluorescence spectra of I and II dissolved in standard buffer ($\lambda_{ex}$=295 nm) were measured in small volume, 1-cm pathlength quartz cuvettes at 298 K using a Varian Cary Eclipse fluorescence spectrophotometer operated with the Cary Eclipse Bio software package (1 nm steps, 5 nm excitation and emission slits). Kinetics data were collected at 30 s intervals using the same software on samples with controlled temperature and stirring.

For the fluorometric enzymatic assay, an aliquot (2 μL) of active MMP-7 (0.454 μg/μL) was added into 0.998 mL solution of $^{129}$Xe biosensor I with known concentration at 298 K. Fluorescence spectra were collected from 310-450 nm. All reported fluorescence data are uncorrected and are roughly 5 nm red-shifted from the values obtained when the instrumental correction feature is employed. Trp fluorescence at 400 nm was analyzed as a function of time, since there was little contribution at this wavelength from monopropargyl-cryptophane-A fluorescence. The enzyme activity was calculated from the initial rate of decrease in Trp emission at 400 nm, over the time interval that corresponded to the first 10-15% completion of the reaction. The $k_{cat}/K_M$ value for biosensor I was calculated by non-linear regression of the activity data by varying the biosensor concentration from 6-100 μM; double-reciprocal 1/v versus 1/[S] Lineweaver-Burk plots[49] gave a similar $k_{cat}/K_M$ value.

$^{129}$Xe NMR Spectroscopy $^{129}$Xe chemical shift data for I and II were collected in D$_2$O solution on a home-made spectrometer[50] connected to a home-built $^{129}$Xe probe mounted in the bore of an Oxford 9.4 T magnet ($^1$H=400 MHz). Isotopically enriched xenon (86% $^{129}$Xe and 0.13% $^{131}$Xe, Spectra Gases) was polarized and cryogenically separated from the buffer-gas mixture in a Nycomed-Amersham (now GE) IGI.Xe.2000 polarizer (output polarization 10-20%), then quickly transferred to a special aluminum container inside the $^{129}$Xe probe. At 9.4 T, the spin relaxation time $T_1$ of $^{129}$Xe gas in the container ranged from 70 to 120 min. A 5-mm sample test tube and an NMR tank circuit, along with the output gas capillary, were mounted on a removable probe insert, a configuration which allowed the sample to be changed without removing the hyperpolarized xenon container from the magnet bore. Sample temperature (unregulated) in the probe was stable at 18±1° C., whereas the solutions were prepared at rt, 23±1° C. This difference in temperature led to an initial cooling of the sample upon introduction into the probe, and the sample was allowed to sit to achieve thermal equilibrium with the probe. By opening a needle valve mounted on the container and monitoring the output gas flow rate, pure hyperpolarized xenon gas was gently bubbled through the test tube containing the sample solution, then the bubbling was stopped and NMR scans (n=1 to 32, $^{129}$Xe frequency 110.45 MHz, 10-30° tipping pulse) were performed and averaged. Raw Free Induction Decay (FID) signals were recorded in quadrature, then processed using standard baseline and phase corrections, fast Fourier transform, and Gaussian broadening of 20 Hz. Peaks attributed to gaseous xenon at 1 atm inside the input capillary (coaxial with the vertical sample tube) were taken as +0.55 ppm frequency reference, making the observed peaks consistent with the published data for $^{129}$Xe dissolved in pure D$_2$O and in cryptophanes, after taking into account the temperature dependence of the frequency shifts. All curve fitting was performed with IGOR Pro 5 (WaveMetrics, Inc., Oreg.) prior to applying Gaussian broadening. The uncertainties in $^{129}$Xe chemical shifts from peak fits were small (~2 Hz, 0.02 ppm), with additional sources of error (such as assignment of the gas reference peak) being much less than the linewidths of approximately 20 Hz. These contributions resulted in peak uncertainties of approximately ±0.05 ppm. $^{129}$Xe chemical shifts are reported to a precision of ±0.1 ppm.

Synthesis of Cyclotriguaiacylene (4)

3-Methoxy-4-(2-propenyloxy)benzenemethanol: Acetone (107.5 mL), vanillyl alcohol (25 g, 0.163 mol), and allyl bromide (15.8 mL, 0.183 mol) were added to a 250 mL, round-bottomed flask and stirred until homogeneous. Potassium carbonate (22.5 g, 0.163 mol) was then added slowly, which briefly gave a light pink color that indicated deprotonation of the phenol. The mixture was heated at 60° C. overnight. The reaction was monitored by TLC using 10% acetone in $CH_2Cl_2$ as eluent. Upon completion, the reaction mixture was allowed to cool to rt with stirring. The acetone was removed under vacuum, yielding a white residue. $CH_2Cl_2$ (200 mL) and $H_2O$ (200 mL) were added to redissolve the residue and transferred to a separatory funnel. The aqueous layer was removed and the organic layer was washed with 1 M NaOH (3×100 mL) and saturated NaCl (1×100 mL). The organic layer was then collected, dried over $MgSO_4$. After filtration, the solvent was removed under vacuum to afford a yellow powder. The yellow powder was redissolved in EtOAc (250 mL), which was subsequently removed under vacuum (in order to remove excess allyl bromide) to afford the product as a fine, white powder (30.0 g, 93% yield). $^1H$ NMR δ=6.94 (s, 1H), 6.86 (s, 2H), 6.09 (multi, 1H), 5.42 (dd, J1=20, J2=1.5, 1H), 5.30 (dd, J1=20, J2=1.5, 1H), 4.63 (d, J=3.6, 2H), 4.62 (d, J=5, 2H), 3.89 (s, 3H), 1.57 (t, J=6, 1H).

2,7,12-Trimethoxy-3,8,13-tris(2-propenyloxy)-10,15-dihydro-5H-tribenzo[a,d,g] cyclononene: 3-Methoxy-4-(2-propenyloxy)benzenemethanol (30.0 g) was dissolved in methanol (220 mL) and the solution was cooled to 0° C. Perchloric acid (70%, 89.9 mL) was then added dropwise to the solution under nitrogen atmosphere. A pink color developed and deepened to magenta during the course of the reaction, which was allowed to run overnight. Upon completion, the reaction mixture was diluted with $CH_2Cl_2$ (200 mL) and cooled on ice. 5 M NaOH (200 mL) was then added dropwise over a 10-min period, followed by the addition of saturated bicarbonate solution (200 mL). The mixture was stirred for 1-2 h as its color turned from pink to yellow. The organic layer was collected and dried on $Na_2SO_4$. After filtration, the solvent was removed under vacuum to afford a yellowish residue. The residue was transferred into a 125-mL Erlenmeyer flask, diluted with 60 mL of diethyl ether and sonicated for 1 h. The ether level was noted before sonication, and refilled to approximately the same level to replace any evaporated solvent. The crude product was digested in ether overnight. The mixture thickened and turned oatmeal color. The product was collected by filtration, washed with ether (2×30 mL) and dried under vacuum to afford final product as a white powder (13.5 g, 45.9% yield). $^1H$ NMR δ=6.83 (s, 3H), 6.78 (s, 3H), 6.05 (multi, 3H), 5.38 (dd, J1=10, J2=1.4, 3H), 5.25 (dd, J1=10, J2=1.4, 3H), 4.75 (d, J=15, 3H), 4.58 (multi, 6H), 3.83 (s, 9H), 3.52 (d, J=10, 3H).

2,7,12-Trihydroxy-3,8,13-trimethoxy-10,15-5H-tribenzo [a,d,g]cyclononene (4, also known as cyclotriguaiacylene): 2,7,12-Trimethoxy-3,8,13-tris(2-propenyloxy)-10,15-dihydro-5H-tribenzo[a,d,g]cyclononene (13.5 g) was dissolved in THF (405 mL) and EtOH (270 mL). The solution was heated to 60° C., to which was added sequentially $H_2O$ (13.46 mL), Pd/C (2.69 g), and TsOH (0.4832 g, 2.54 mmol). The mixture was heated at 60° C. under nitrogen overnight. The reaction was monitored by TLC using 50:50 ethyl acetate:hexane as eluent. Upon completion, the reaction mixture was cooled to it and filtered over Celite. The Celite was washed with THF (3×100 mL). The filtrate was collected and solvent was removed under vacuum to yield an off-white residue. The residue was redissolved in THF (700 mL) and EtOAc (200 mL). Half of the 900 mL solution was transferred to a 1000-mL separatory funnel. To this was added EtOAc (200 mL for phase separation), and the resulting mixture was washed with brine (2×100 mL). This same process was repeated for the second portion of solution. The organic layers were then combined and dried over MgSO4. After filtration, the filtrate was collected and dried under vacuum to give a brown, shiny residue. The residue was digested in chloroform (162 mL) for 1 h and the desired product was isolated by filtration to yield a fine, off-white powder (8.42 g, 81% yield). $^1H$ NMR δ=6.89 (s, 3H), 6.78 (s, 3H), 5.37 (s, 3H), 4.72 (d, J=15, 3H), 3.83 (s, 9H), 3.51 (d, J=10, 3H). $^{13}C$ NMR δ=145.6, 144.4, 132.6, 130.4, 117.1, 114.0, 56.0, 35.0.

Figure 3:
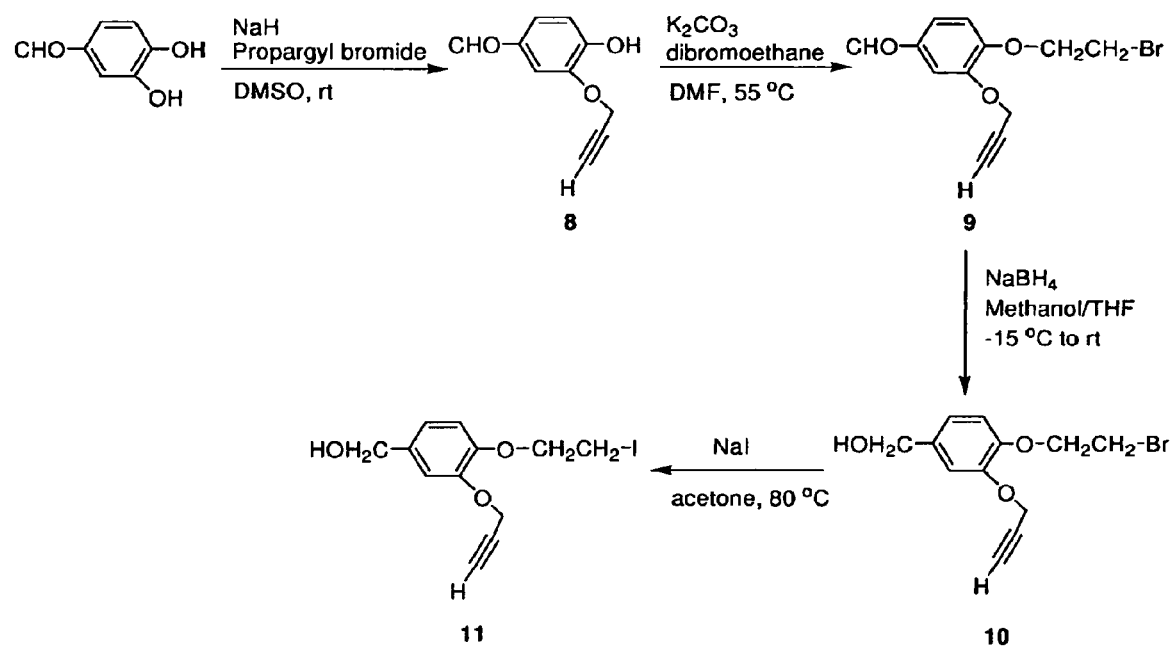
FIG. 3 shows a schematic of the synthesis of [3-propargyloxy-4-(2-iodoethoxy) phenyl]methanol

Synthesis of [3-propargyloxy-4-(2-iodoethoxy)phenyl] methanol (FIG. 3)

3-propargyloxy-4-hydroxybenzaldehyde (8): In a dry two-neck flask with a nitrogen inlet, NaH (4.8 g, 200 mmol, 2 equiv) was added into anhydrous DMSO (50 mL) in small portions. While stirring and cooling this solution to 0° C., anhydrous DMSO (60 mL) containing 3,4-dihydroxybenzaldehyde (13.8 g, 100 mmol, 1 equiv) was added dropwise into the flask. This reaction mixture was stirred at rt for 30 min. Propargyl bromide (11.1 mL 100 mmol, 1 equiv) was then added dropwise via syringe and the mixture was stirred at rt overnight. The mixture was poured onto ice, neutralized by a 1 M HCl solution and the product was extracted with ethyl acetate (3×250 mL). The combined organic extracts were concentrated to about 250 mL, washed with brine (5×250 mL) and dried over $MgSO_4$. After filtration the solvent was removed under vacuum to afford crude product as a brownish powder. This was chromatographed on a silica gel column with an eluent of ethyl acetate/hexane/acetic acid (20/80/1) to give 8 as a white powder (12.2 g, yield: 69%). $^1H$ NMR δ=9.84 (s, 1H, —CHO), 7.53 (d, J=1.7, 1H), 7.49 (dd, J1=1.7, J2=8, 1H), 7.09 (d, J=8, 1H), 6.22 (s, 1H, —OH), 4.84 (d, J=2.5, 2H, —OCH2), 2.60 (t, J=2.5, 1H, —C≡CH). $^{13}C$ NMR δ=190.92 (—CHO), 152.20, 145.37, 129.96, 128.14, 115.35, 111.36, 77.41 (—C≡CH), 77.10 (—C≡CH), 57.23 (—OCH2). HRMS calculated for $C_{10}H_8O_3$ ($M^+$), 176.0473; found, 176.0465.

3-propargyloxy-4-(2-bromoethoxy)benzaldehyde (9): To a dry two-neck flask, compound 8 (4.3 g, 24 mmol, 1 equiv) and $K_2CO_3$ (16 g, 120 mmol, 5 equiv) were added into anhydrous DMF (50 mL) under nitrogen. The mixture was stirred at rt for 30 min. Dibromoethane (21 mL, 240 mmol, 10 equiv) was then added in one portion and the resulting mixture was heated overnight at 55° C. under a nitrogen atmosphere. The mixture was poured into water (400 mL) and the product was extracted with ethyl acetate (3×200 mL). The combined organic extracts were concentrated to about 250 mL and were washed subsequently with 1 M NaOH (2×200 mL), water (250 mL) and brine (5×250 mL). The organic layer was dried over $MgSO_4$, filtered and the solvent was removed under vacuum. The crude product as yellow oil was chromatographed on a silica gel column with the eluent of ethyl acetate/ hexane (20/80) to give pure product as a white solid (5.2 g, yield: 77%). $^1H$ NMR δ=9.88 (s, 1H, —CHO), 7.58 (d, J=1.8, 1H), 7.54 (dd, J1=1.8, J2=8, 1H), 7.02 (d, J=8, 1H), 4.83 (d, J=2.3, 2H, —$OCH_2$), 4.43 (t, J=6.6, 2H, —$OCH_2CH_2Br$), 3.72 (t, J=6.6, 2H, —$OCH_2CH_2Br$), 2.54 (t, J=2.3, 1H, —C≡CH). $^{13}C$ NMR δ=190.68 (—CHO), 153.70, 147.77, 130.79, 127.01, 113.95, 113.19, 78.01 (—C≡CH), 76.63 (—C≡CH), 68.98 (—$OCH_2$CH2Br), 57.16 (—$OCH_2$C≡CH), 28.45 (—$OCH_2CH_2$Br). HRMS calculated for $C_{12}H_{11}BrO_3$ ($M^+$), 281.9892; found, 281.9903.

[3-propargyloxy-4-(2-bromoethoxy)phenyl]methanol (10): To a two-neck flask with a nitrogen inlet, compound 9 (5.2 g, 18 mmol, 1 equiv) was dissolved in 200 mL methanol/ THF (10/1). The solution was cooled to −10° C. in a salted ice bath, followed by the addition of sodium borohydride (0.8 g, 21 mmol, 1.2 equiv). The mixture was stirred at 0° C. for 20 min, then allowed to warm to rt and stirred for an additional 20 min. The mixture was concentrated under vacuum, cooled to 0° C. and acidified with diluted HCl solution. The aqueous solution was extracted with ethyl acetate. The combined organic extracts were washed with brine (200 mL) and dried over MgSO$_4$. After filtration the solvent was removed under vacuum to afford crude product as a yellowish solid. This was chromatographed on a silica gel column (eluent: 0% to 5% of methanol in CH$_2$Cl$_2$) to give 10 as a white solid (4.95 g, yield: 95%). $^1$H NMR δ=7.10 (d, J=1.8, 1H), 6.97 (dd, J1=1.8, J2=8, 1H), 6.93 (d, J=8, 1H), 4.78 (d, J=2.3, 2H, —OCH2C≡CH), 4.64 (d, J=5.8, 2H, —CH$_2$OH), 4.34 (t, J=6.6, 2H, —OCH$_2$CH$_2$Br), 3.66 (t, J=6.6, 2H, —OCH$_2$CH$_2$Br), 2.51 (t, J=2.3, 1H, —C≡CH), 1.68 (t, J=5.8, 1H, —CH$_2$OH). $^{13}$C NMR δ=147.90, 145.60, 135.34, 121.32, 115.46, 114.92, 78.78 (—C≡CH), 76.12 (—C≡CH), 70.54 (—CH$_2$OH), 66.28 (—OCH$_2$CH$_2$Br), 57.38 (—OCH2C≡CH), 29.32 (—OCH$_2$CH$_2$Br). HRMS calculated for C$_{12}$H$_{11}$BrO$_3$ (M+Na$^+$), 354.9807; found, 354.9810.

[3-propargyloxy-4-(2-iodoethoxy)phenyl]methanol (11): Sodium iodide (10 g, 70 mmol, 4 equiv) was added in one portion to the stirred solution of 10 (5 g, 18 mmol, 1 equiv) in acetone (40 mL). The mixture was heated to 50° C. under nitrogen overnight. Upon reaction completion, the solvent was removed under vacuum. The resulting solid was dissolved in CH$_2$Cl$_2$ (200 mL) and washed subsequently with sodium thiosulfate solution (2×200 mL), water (200 mL) and brine (200 mL). The organic layer was dried over MgSO$_4$, filtered and solvent was removed under vacuum to afford product as a white solid (5.71 g, yield: 98%). $^1$H NMR δ=7.09 (d, J=1.8, 1H), 6.96 (dd, J1=1.8, J2=8, 1H), 6.91 (d, J=8, 1H), 4.78 (d, J=2.3, 2H, —OCH2C≡CH), 4.63 (d, J=5.8, 2H, —CH2OH), 4.30 (t, J=6.6, 2H, —OCH2CH2I), 3.45 (t, J=6.6, 2H, —OCH2CH2I), 2.51 (t, J=2.3, 1H, —C≡CH), 1.68 (t, J=5.8, 1H, —CH2OH). $^{13}$C NMR δ=147.80, 145.50, 135.14, 121.22, 115.33, 114.86, 78.74 (—C≡CH), 76.09 (—C≡CH), 70.44 (—CH2OH), 65.21 (—OCH$_2$CH$_2$I), 57.38 (—OCH$_2$C≡CH), 1.32 (—OCH$_2$CH$_2$I). HRMS calculated for C$_{12}$H$_{11}$BrO$_3$ (M–OH$^+$), 267.0021; found, 267.0008.

Figure 4:
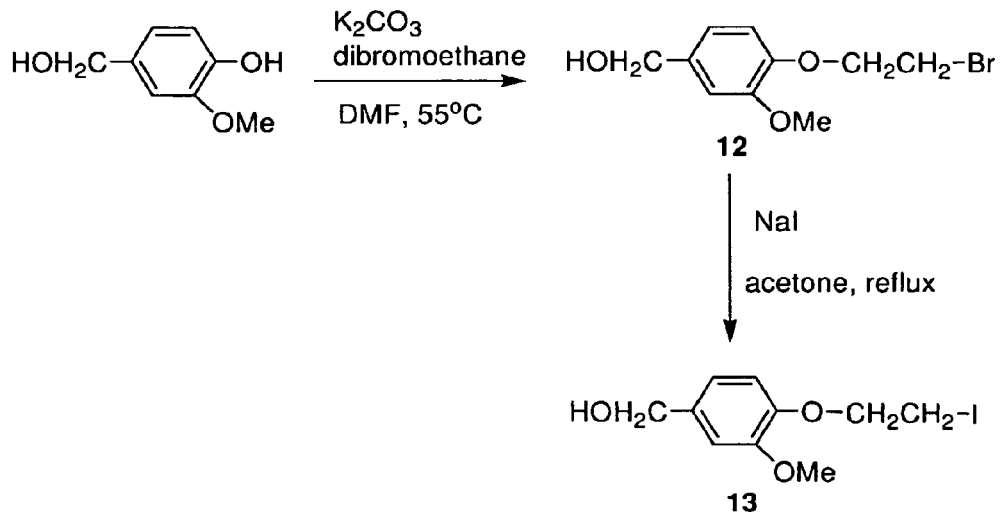
FIG. 4 shows a schematic of the synthesis of [4-(2-iodoethoxy)-3-methoxyphenyl]methanol

Synthesis of [4-(2-iodoethoxy)-3-methoxyphenyl]methanol (FIG. 4)

[4-(2-bromoethoxy)-3-methoxyphenyl]methanol (12): According to the procedure for the synthesis of 9, compound 12 (5.1 g, yield: 60%) was obtained from 3-methoxy-4-hydroxybenzylalcohol (5 g, 33 mmol, 1 equiv), dibromoethane (25 mL, 330 mmol, 10 equiv) and K$_2$CO$_3$ (22 g, 162 mmol, 5 equiv) in anhydrous DMF (60 mL). $^1$H NMR δ=6.96 (d, J=1.6, 1H), 6.90 (d, J=8, 1H), 6.88 (dd, J1=1.6, J2=8, 1H), 4.63 (d, J=5.8, 2H, —CH$_2$OH), 4.33 (t, J=6.6, 2H, —OCH$_2$CH$_2$Br), 3.88 (s, 3H, —OCH3), 3.66 (t, J=6.6, 2H, —OCH$_2$CH$_2$Br), 1.65 (t, J=5.8, 1H, —CH$_2$OH).

[4-(2-iodoethoxy)-3-methoxyphenyl]methanol (13): According to the procedure for the synthesis of 11, compound 13 (3.45 g, yield: 86%) was obtained from 12 (3.4 g, 13 mmol, 1 equiv) and sodium iodide (7.8 g, 52 mmol, 4 equiv) in acetone (40 mL). NMR δ=6.95 (S, 1H), 6.87 (s, 2H), 4.63 (d, J=5.8, 2H, —CH$_2$OH), 4.30 (t, J=6.6, 2H, —OCH$_2$CH$_2$I), 3.88 (s, 3H, —OCH3), 3.45 (t, J=6.6, 2H, —OCH$_2$CH$_2$I), 1.65 (t, J=5.8, 1H, —CH$_2$OH).

Solid-Phase Synthesis

Peptide synthesis: Peptides were synthesized using standard Fmoc amino acid protection chemistry[4] on Fmoc-Lys (Boc)-Wang resin (0.1 mmol scale). Couplings of Fmoc-protected amino-acids to the resin were carried out with HBTU and N-methylmorpholine to generate the activated ester. Synthesis started with the C-terminal amino acid. The resin was swelled in DMF (10 min) prior to synthesis. Amino acids were then added sequentially until 3-azidoproponic acid was attached at the N-terminus as the final step. All residues were coupled onto resin by the following procedure: removal of Fmoc group (20% piperidine solution in DMF, 2×5 min), wash (DMF, 6×30 sec), activation (amino acid/HBTU/N-methylmorpholine, 1×30 sec) coupling (amino acid/HBTU/N-methylmorpholine, 1×20 min), rinse (DMF, 3×30 sec).

After completion of synthesis, the resin was collected, washed with 1:1 CH$_2$Cl$_2$/methanol (3×30 mL) and dried under vacuum. Cleavage of the peptide from resin was accomplished by treating the dried resin with a mixture of TFA, water, thioanisole, phenol, ethanedithiol and triisopropylsilane (81.5/5/5/5/2.5/1) at rt for 3 h for peptide containing unprotected Trp and with TFA, water and triisopropylsilane (95/2.5/2.5) for peptide without the Trp residue. The resin was removed by filtration and peptide was precipitated from the filtrate upon the addition of anhydrous Et$_2$O. The peptide was washed with anhydrous Et$_2$O, collected by centrifugation and dried under vacuum to provide crude peptide.

Temperature Dependence of Trp Fluorescence for I and 3

Figure 12:
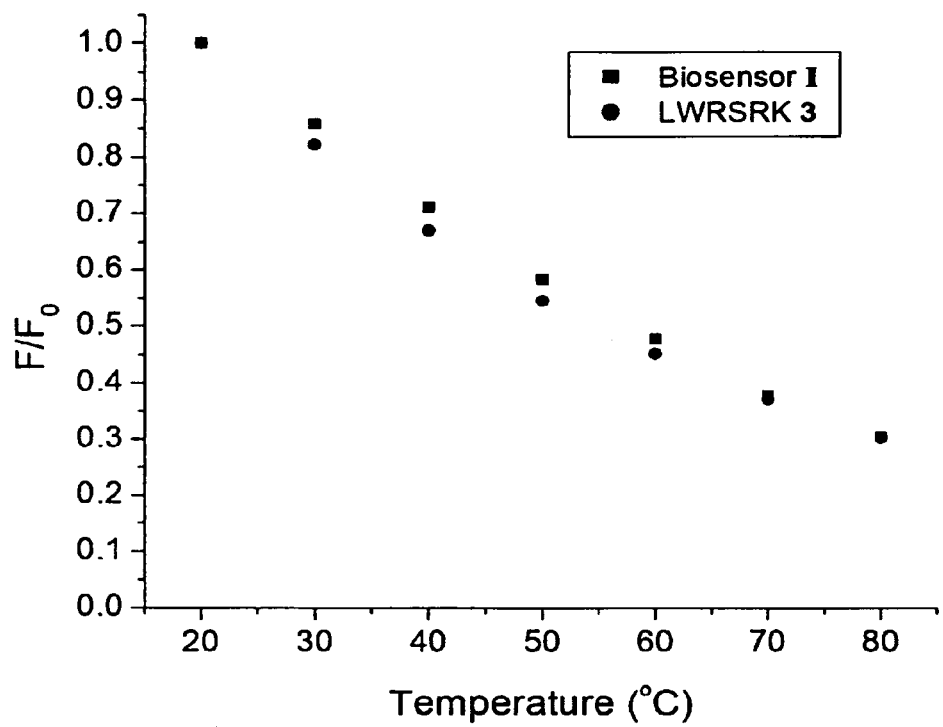
FIG. 12 shows fraction of biosensor I (38 µM) and hexapeptide 3 (38 µM) Trp fluorescence remaining (observed fluorescence divided by original fluorescence, $F/F_0$) as a function of temperature ($\lambda_{ex}$=295 nm, $\lambda_{em}$=358 nm). Data for the two separate compounds are overlaid to show their similar temperature profiles.
Figure 13:
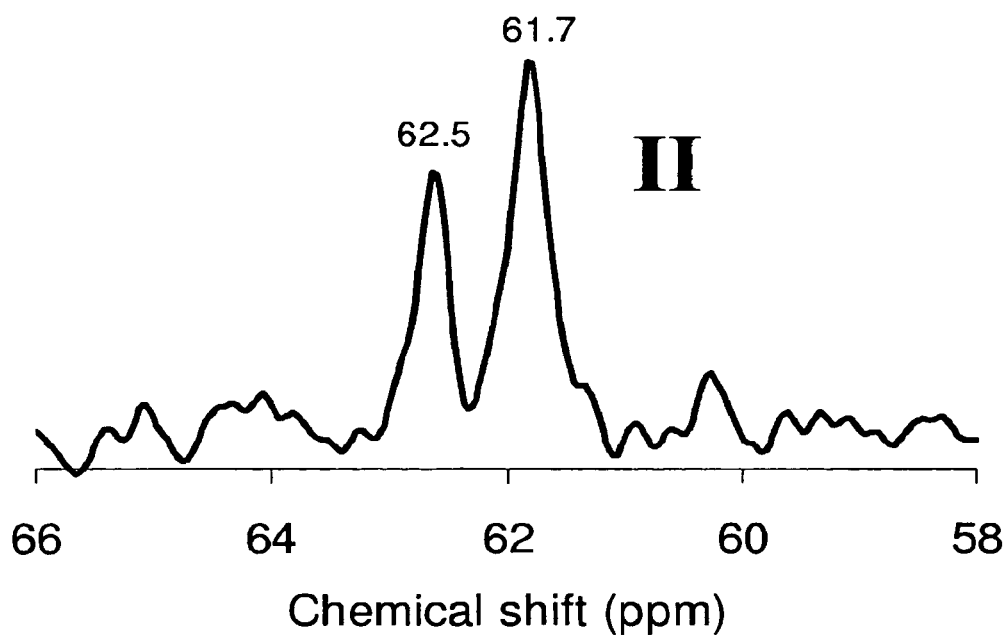
FIG. 13 shows hyperpolarized $^{129}$Xe NMR spectrum of biosensor II (190 µM) in $D_2O$. Peaks were observed at 61.7 and 62.5 ppm with linewidths of 24 Hz and 18 Hz, respectively.

Fluorescence spectra of biosensor I and hexapeptide LWRSRK 3 (λex=295 nm), each dissolved at 38 μM in standard buffer, were measured at various temperatures between 293-353 K in a small volume quartz cuvette using a Varian Cary Eclipse fluorescence spectrophotometer (1 nm steps, 5 nm excitation and emission slits) operated with the Cary Eclipse Bio software package. The fraction of remaining Trp fluorescence (F/F$_0$) was calculated for each compound and plotted as a function of temperature (FIG. 12). Virtually no difference was observed between these two compounds, which provided evidence for a lack of intra- or intermolecular quenching at rt in the intact biosensor I.

Example 1

Designing $^{129}$Xe NMR Biosensors for Matrix Metalloproteinase Detection

Synthesis of Peptide-Cryptophane-A Conjugates

In designing biosensor I, the sequence RPLALWRS (SEQ ID NO. 36) was chosen because of the high specificity of MMP-7 for this substrate and its successful function in a fluorogenic beacon for in vivo detection and imaging of MMP-7. Schemes 1 and 2 outline the synthesis of I. Cryptophane-A was synthesized with a single propargyl group, which not only overcame the hurdles of allyl ether deprotection and subsequent low-yielding alkylation that confronted previous studies with cryptophanol, but also provided an efficient route to couple a variety of peptides to cryptophane-A via azide-alkyne [3+2]cycloaddition. II was generated through two different methods: a) MMP-7-mediated enzymatic hydrolysis of I, and b) direct synthesis on solid support, as described (Scheme 2—FIG. 5). Both routes gave the desired product, as confirmed by HPLC and MALDI-TOF mass spectrometry.

Monopropargylated cryptophane-A 7 was synthesized in 12 nonlinear steps by following a modified template method which involved stepwise incorporation of two types of linkers and the formation of two cyclotriveratrylene units in two different stages of synthesis. Starting from vanillyl alcohol, cyclotriguaiacylene 4 was prepared in three steps and 35% overall yield, based on a known procedure. Two linkers were synthesized for attachment to 4: [3-propargyloxy-4-(2-iodoethoxy)phenyl]methanol (4 steps, 49% yield) and [4-(2-iodoethoxy)-3-methoxyphenyl]methanol (2 steps, 52% yield). In the presence of cesium carbonate as base, 4 was alkylated with one [3-propargyloxy-4-(2-iodoethoxy)phenyl]methanol linker, followed by two [4-(2-iodoethoxy)-3-methoxyphenyl]methanol linkers, to give precursor 6 in 50-55% yield for the two alkylation steps. As compared with literature reports of 15-25%, substantially improved yields of alkylation were achieved with lower reaction temperatures and longer reaction times. The most challenging step was the cyclization of precursor 6 to afford 7. This had been reported to be low-yielding in the synthesis of other monofunctionalized cryptophane-A compounds. Several trials on the final cyclization using pure formic acid or a chloroform/formic acid mixture (50/50) at 55° C. led to multiple non-isolable compounds, with very little product appearing on TLC. However, the desired cyclized product 7 was obtained in 49% yield by using perchloric acid/MeOH (50/50) at rt. Further attempts using perchloric acid/MeOH mixtures at elevated temperatures led to decomposition of starting material.

Figure 6:
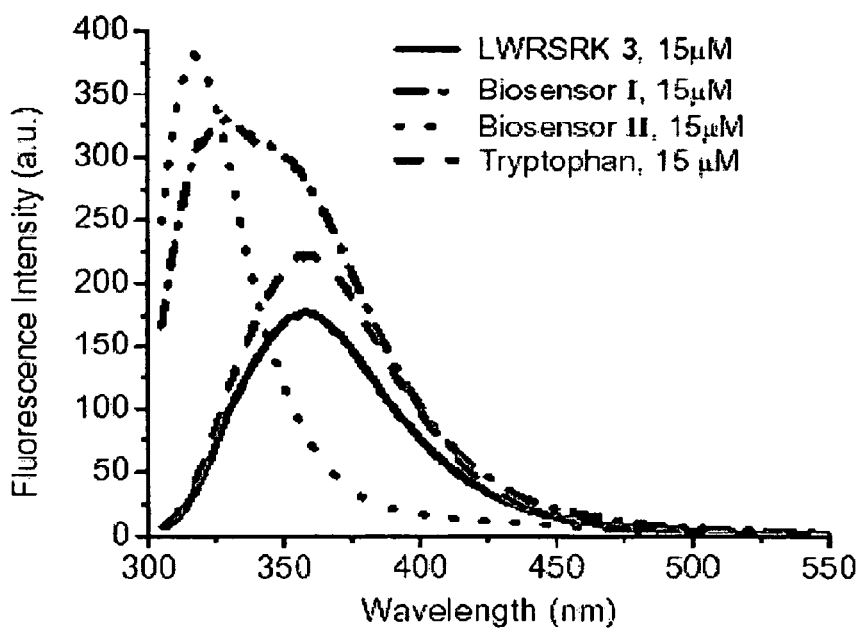
FIG. 6 shows fluorescence spectra of biosensor I, cleaved biosensor II, hexapeptide LWRSRK (SEQ ID NO. 35) (hereinafter denoted as 3) and tryptophan. All spectra were obtained by excitation at 295 nm at room temperature in standard buffer.

The azidopeptides $N_3$—$CH_2CH_2$—$CONH_2$—RKRPLA-LWRSRK (SEQ ID NO. 33) 1 and $N_3$—$CH_2CH_2$—$CONH_2$—RKRPLA (SEQ ID NO. 34) 2 were synthesized by standard solid-phase synthesis using Fmoc-substituted reagents. 3-azido propionic acid was prepared according to literature procedures, and incorporated as the N-terminal residue. Yields of purified peptides were about 80% for all peptide coupling and cleavage steps, based on the maximum possible yield from the amount of starting resin. While still attached to the Wang resin, the azidopeptide was coupled to the monopropargyl-cryptophane-A by a copper (I)-catalyzed [3+2]cycloaddition to give biosensor in 80-92% yield. After cleavage from solid support, reversed phase HPLC analysis showed complete disappearance of azidopeptide and appearance of new peaks at longer retention times, as expected for peptides conjugated to the hydrophobic cryptophane. Pooled fractions for each product were collected and lyophilized, and all compounds were characterized by MALDI-TOF mass spectrometry. FIG. 6 shows the emission spectra for the intact cryptophane sensor I, cleaved cryptophane sensor II, LWRSRK (SEQ ID NO. 35) 3, and free tryptophan.

Enzymatic Assay

The ability of MMP-7 to hydrolyze $^{129}$Xe biosensor I was initially confirmed by HPLC analysis (FIG. 3a). A standard assay was performed by incubating a 1 mL reaction mixture of 32 nmol I and 42 pmol MMP-7 at 310 K. Reaction progress was monitored by analyzing aliquots of the reaction mixture at regular intervals. HPLC data showed a progressive decrease of the intact biosensor I at retention time of 15.6 min and a concomitant increase of two new peaks at retention times of 3.0 min and 17.9 min. MALDI-TOF mass spectrometry identified these new peaks as the cleaved hexapeptide LWRSRK 3 and cryptophane-peptide product II, respectively. The peptide cleavage pattern agreed with previous assays using this substrate. The 2.3-min increase in retention time was consistent with the lower charge of the cleaved product II (+2) relative to the intact biosensor I (+5).

Biosensor I contained a single tryptophan near the C-terminus that was two residues removed from the cleavage site for MMP-7. Considering the sensitivity of Trp fluorescence to its environment, we explored whether the Trp emission changed upon peptide cleavage. The broad fluorescence spectrum of I (FIG. 6) was assigned to contributions from both cryptophane-A ($\lambda_{max}$=318 nm) and Trp ($\lambda_{max}$=358 nm). The Trp fluorescence spectra of I and 3 were red-shifted, as is typical for the fully solvated amino acid in pH 7.5 water. The fluorescence spectrum of 3 was slightly diminished from free tryptophan in solution (FIG. 6), indicating modest Trp quenching in the environment of the hexapeptide. There are no other aromatic residues within the hexapeptide that would contribute to quenching by energy transfer, but quenching of tryptophan by excited-state proton and electron transfer is well known within peptides and proteins.

In enzyme kinetics studies, the fluorescence spectrum of I was taken at 30 s intervals after addition of MMP-7 (FIG. 7b). A continuous decrease of Trp emission was observed. The change in fluorescence intensity at 400 nm was used to calculate the initial velocity (v) of the enzyme reaction. The v values determined by HPLC and fluorometric methods were in excellent agreement (Table 1), which validated using the fluorometric assay to monitor this enzyme reaction. The Trp fluorescence assays were easier to run, allowed continuous monitoring of the reaction, provided greater sensitivity, and required less material than HPLC-based UV-vis absorbance measurements.

TABLE 1

Comparison of MMP-7 activity towards I, monitored by UV-vis (HPLC) and fluorometry

| | Biosensor I (µM) | | |
|---|---|---|---|
| | 6 | 50 | 100 |
| Initial velocity (pmol/s) HPLC assay | 1 | 10 | 7 |
| fluorometric assay | 0.9 | 9 | 8 |

Fluorescence Studies

Figure 8:
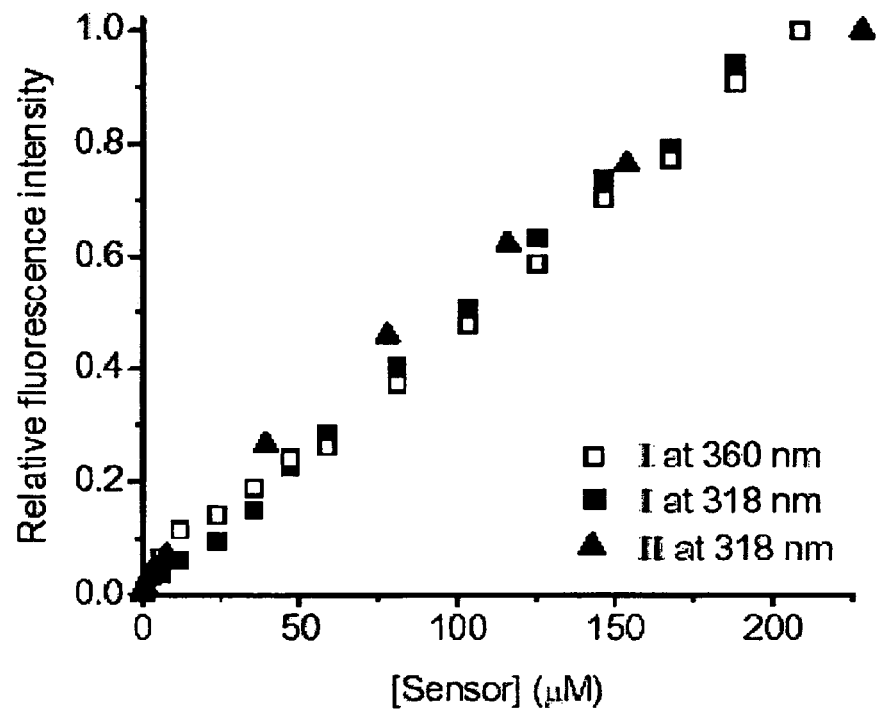
FIG. 8 shows concentration dependence of biosensor fluorescence intensity (I and II, $\lambda_{ex}$=295 nm, $\lambda_{em}$ monitored at 318 or 358 nm, corresponding to emission from cryptophane and Trp, respectively). Solutions were at room temperature in standard buffer. The fluorescence intensity for each compound at a given wavelength and concentration was normalized to its value at the maximum biosensor concentration, in order to facilitate comparison and show linearity over a large concentration range.

Experiments were performed to identify the important contributions to the observed Trp fluorescence quenching. In the fully extended biosensor I (FIG. 1) cryptophane and Trp were separated by approximately 40 Å. Temperature dependence studies identified little contribution to Trp quenching from the cryptophane within the intact biosensor I. The observed decrease in Trp fluorescence at elevated temperatures ($\lambda_{em}$=358 nm, $F/F_0$=0.3 at 353 K) was virtually identical to that seen with the Trp-containing hexapeptide 3, and was thus attributed to temperature-dependent solvent quenching by non-radiative decay processes. The similar fluorescence temperature dependence for I and 3 also suggested a lack of intermolecular interactions between biosensors, since higher temperatures should dissociate any aggregates in solution. This was confirmed with I and II by comparing the concentration dependence of fluorescence intensity ($\lambda_{ex}$=295 nm, $\lambda_{em}$=318 nm for cryptophane and $\lambda_{em}$=358 nm for Trp), after correcting for inner filter effects and dilution. Neither compound's fluorescence intensity deviated from linearity over the concentration range, 1-250 µM (FIG. 8). The absorption and fluorescence maxima were unchanged over this range. The biosensors were very soluble in water, and the fluorescence studies indicated that I, II, and related amphiphilic cryptophanes were unlikely to aggregate at concentrations relevant to the present $^{129}$Xe NMR studies.

Figure 9:
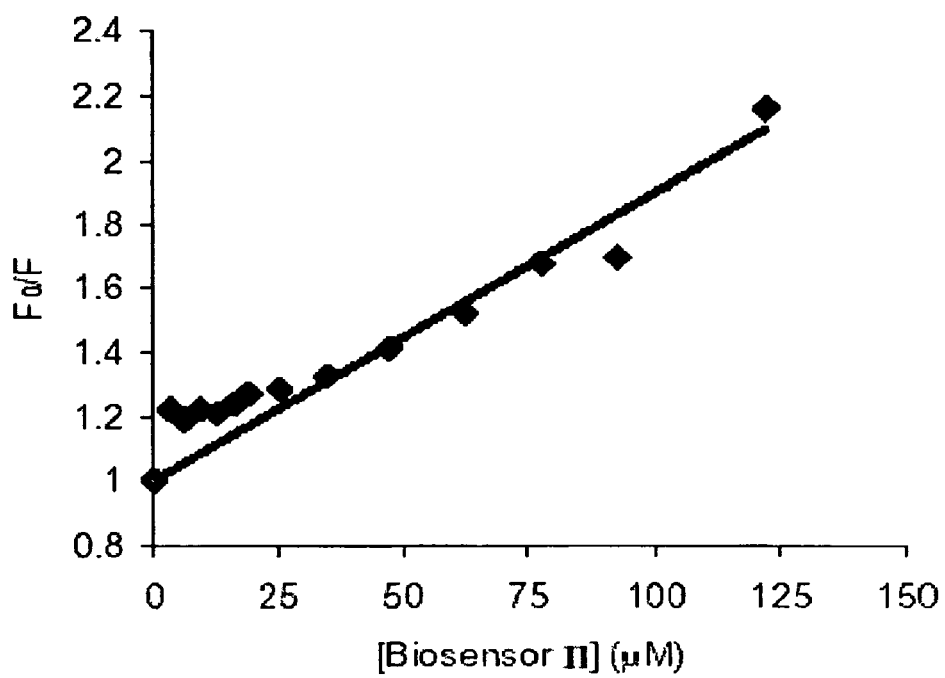
FIG. 9 shows Stern-Volmer plots of fluorescence quenching of Trp-containing hexapeptide 3 (16 µM, 298K in standard buffer) by cleaved biosensor II. Solution of 3 was titrated with 3.18 mM II, to achieve concentrations of II between 0 and 120 µM. Steady-state fluorescence measurements found the ratio of initial fluorescence, $F_0$, to observed fluorescence, F, at each quencher concentration. The linear fit gave an $R^2$ value of 0.88, which indicated a dominant static quenching mechanism. The slope of this line gave the association constant, $K_S$=9000 $M^{-1}$, for the II-3 complex.

Having ruled out a prevalent role for intra- and intermolecular interactions within or between biosensors, we sought further to explain the decrease in Trp fluorescence upon enzymatic cleavage. The quenching process observed in the MMP-7 cleavage assay was very efficient, which discounted the possibility of diffusion-controlled bimolecular collisional quenching ($k_q \sim 10^9$ $M^{-1}$ $s^{-1}$), based on the low micromolar concentrations of (equimolar) Trp and cryptophane, and short lifetime of the Trp excited state ($\sim 10^{-8}$ s).[55] Thus, it was investigated whether static quenching caused by association between the Trp-containing hexapeptide, LWRSRK 3, and cryptophane, could yield the observed result. To examine this quenching mechanism, the steady-state fluorescence intensity of the hexapeptide LWRSRK 3 was measured as a function of the cleaved sensor II (putative quencher) concentration in standard buffer. This Stern-Volmer experiment could only be performed within a limited range of II concentrations, due to limitations in the quantity of material and the contribution of this compound to total fluorescence. Nonetheless, 8-fold excess quencher was sufficient to elucidate the strength of the cryptophane-hexapeptide interaction. All fluorescence spectra were corrected to remove contributions from cryptophane. The resulting fluorescence maximum at 358 nm, which corresponded to Trp emission of I, decreased with successive additions of II. The slope of $F_0/F$ vs. [II] gave the association constant, $K_S=9000\pm1000$ $M^{-1}$, for the formation of a non-fluorescent ground-state complex between Trp and cryptophane (FIG. 9). The Stern-Volmer experiment revealed strong Trp-cryptophane complex formation leading to a loss of Trp fluorescence. Within this concentration range, there was no significant deviation from linearity that indicated additional contributions from collisional quenching processes.

Cryptophanes are known to encapsulate some cationic molecules with high affinity ($K_A \sim 2700\text{-}6400$ $M^{-1}$) due to both cation-π and hydrophobic interactions, thus comparable association between electron-rich cryptophane and the positively charged peptide could be responsible for stable complex formation. Trp is known to function as an efficient quencher for some organic dyes via photo-induced electron transfer and Trp emission can be quenched by Tyr and Phe via long-range energy transfer. The limited spectral overlap between cryptophane emission and Trp absorption reduced possibilities for long-range fluorescence energy transfer, as evidenced by the lack of Trp quenching that was observed within the intact biosensor I. Alternatively, the observed Trp quenching could involve a shorter-range, photo-induced electron-transfer reaction between Trp and cryptophane-A. However, cryptophane-A (reversible oxidation at 0.69 V for related cryptophane-E in acetonitrile with $Ag/AgNO_3$ reference electrode) and tryptophan (midpoint potential=1.02 V vs. NHE at pH 7) are both good reducing agents, and formation of the Trp radical cation by electron transfer was disfavored thermodynamically. More simply, pi-stacking between tryptophan and the cryptophane could mediate this interaction and lead to quenched Trp fluorescence.

It should be noted that this is a very unusual application of Trp fluorescence quenching to monitor a biochemical process. The inventors are not aware of any other donor-conjugated-acceptor biosensor in which the electronic interaction is absent in the intact biosensor and only occurs when the donor and acceptor are together bimolecularly in solution. The considerable distance (~40 Å) separating the cryptophane and Trp in this system, and apparent lack of intramolecular Trp quenching produced by chain dynamics, contributed to this unusual observation. For monitoring the enzymatic cleavage process at longer times (t>20 min; FIGS. 3a and 3b), the HPLC data were a more transparent indicator of reaction progress, based on defined substrate and product peaks. In the fluorometric assay, the Trp fluorescence decreased linearly for the first 20 min, but showed little apparent decrease after 30 min, which was likely due to the diminishing concentrations of Trp (3) and free cryptophane (II) in solution. By monitoring initial velocities, it was possible to circumvent this problem, and obtain data in good agreement with the less sensitive HPLC assay.

Figure 10:
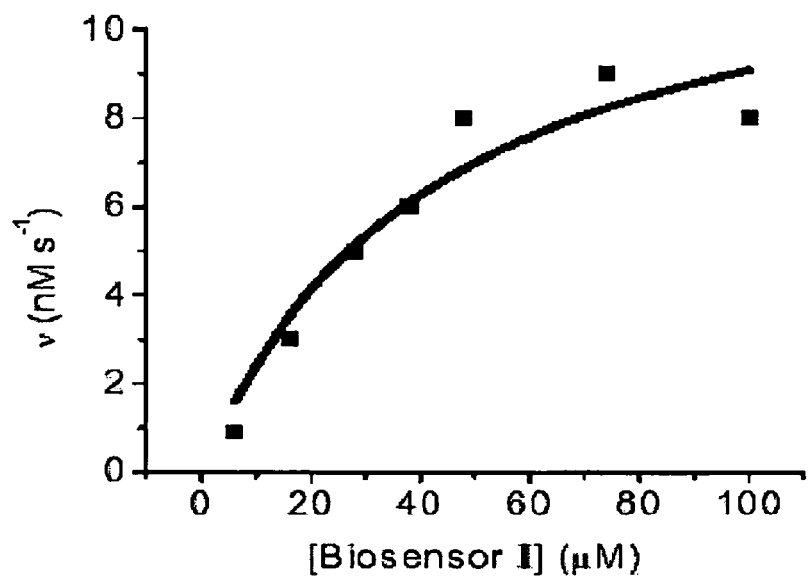
FIG. 10 shows kinetics of proteolysis of biosensor I by MMP-7 (42 nM). Fluorometric assays measuring initial velocity, v, were performed at 298 K in standard buffer. Line represents best fit to Michaelis-Menten model (Equation 1).

Future hyperpolarized $^{129}$Xe MRI studies are likely to be conducted with in vivo concentrations of 10-100 μM biosensor.hyperpolarized $^{129}$Xe complex, based on considerations of biosensor delivery, as well as hyperpolarized $^{129}$Xe lifetime in solution and sensitivity. Thus, the efficiency of the MMP-7 cleavage reaction for biosensor I was compared to the cognate peptide 1 over this biosensor concentration range. The cleavage of I was monitored both fluorometrically and by HPLC UV-vis measurements, whereas 1 (azidopeptide $N_3$—$CH_2CH_2$—$CONH_2$—RKRPLALWRSRK, SEQ ID NO. 33), which lacked a cryptophane quencher, was monitored only by HPLC. Enzyme reaction parameters were determined from measuring the initial consumption of 10-15% of each substrate. The $k_{cat}/K_M$ value was calculated by non-linear regression of the enzyme activity data at different concentrations of I, as shown graphically in FIG. 10 and tabulated in Table 2. The data showed that 1 and I were similarly specific substrates for MMP-7 with virtually identical values for $k_{cat}/K_M$. MMP-7 showed higher affinity for biosensor I ($K_M=43$ μM) than the more natural substrate 1 ($K_M=150$ μM). One explanation for the 3.6-fold lower $V_{max}$ for biosensor I could be stabilization of the enzyme-product complex by the cryptophane, but this remains to be tested in the lab.

TABLE 2

MMP-7 enzyme kinetic parameters for different peptide substrates

| Substrate | $K_M$ (μM) | $V_{max}$ (M s$^{-1}$) | $k_{cat}/K_M$ (M$^{-1}$ s$^{-1}$) |
|---|---|---|---|
| Biosensor I | 43 | $1.3 \times 10^{-8}$ | $7.2 \times 10^3$ |
| $N_3$—$CH_2CH_2$—$CONH_2$-RKRPLALWRSRK 1 | 150 | $4.7 \times 10^{-8}$ | $7.3 \times 10^3$ |
| Dinitrophenyl-RPLALWRS$^a$ | 26 | — | $1.9 \times 10^5$ |

$^a$MMP-7 activity toward this fluorogenic substrate was reported previously at 303 K Both substrates were comparable in affinity to the previously studied, fluorescently labeled MMP-7 consensus sequence, dinitrophenyl-Arg-Pro-Leu-Ala-Leu-Trp-Arg-Ser (SEQ ID NO. 3) ($K_M=26$ μM), but showed roughly 25-fold lower specificity. Substrates 1 and I differed from this fluorogenic peptide with charged arginine and lysine residues at both the C- and N-termini. It appears likely that these residues were responsible for decreasing enzyme specificity and thereby lowering $K_{cat}/K_M$. The two RK units were incorporated into biosensor I in order to improve water solubility and to modulate the electrostatic environment near the cage, but it should be possible to remove these residues and improve substrate specificity. Through these studies, the promising observation was made that the cryptophane had a modest effect on enzyme activity when placed ~35 Å from the MMP-7 cleavage site. Thus, future biosensors can incorporate the enzyme-reactive site much closer to the cage, which will provide additional avenues for modulating the $^{129}$Xe chemical shift. We reiterate that the incorporation of a single Trp within the biosensor provided valuable insight into the molecular structure in solution, and greatly facilitated the enzymatic assays. Future biosensor designs are likely to benefit from also placing tryptophan within the peptide sequence, in some cases much closer to the cryptophane, in order to promote intramolecular quenching.

$^{129}$Xe NMR

Figure 7:
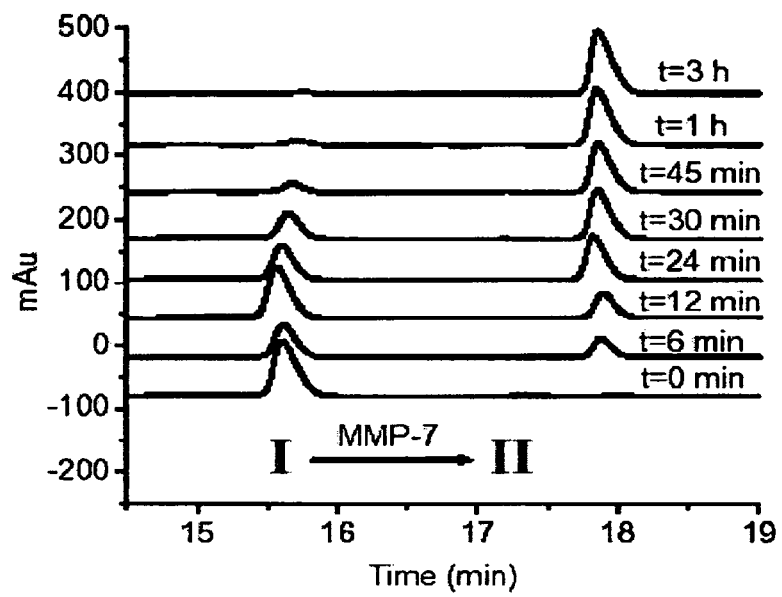
FIG. 7 shows a) HPLC traces for aliquots of biosensor I (32 µM) digested by MMP-7 (42 nM) at room temperature in standard buffer to give II. Proteolysis was stopped at the indicated time points by EDTA addition, then analyzed by reversed phase HPLC. (b) Fluorometry monitored digestion of biosensor I (32 µM) by MMP-7 (42 nM) at rt in standard buffer. Trp fluorescence ($\lambda_{ex}$=295 nm, $\lambda_{em}$=358 nm) decreased during the reaction.
Figure 7:
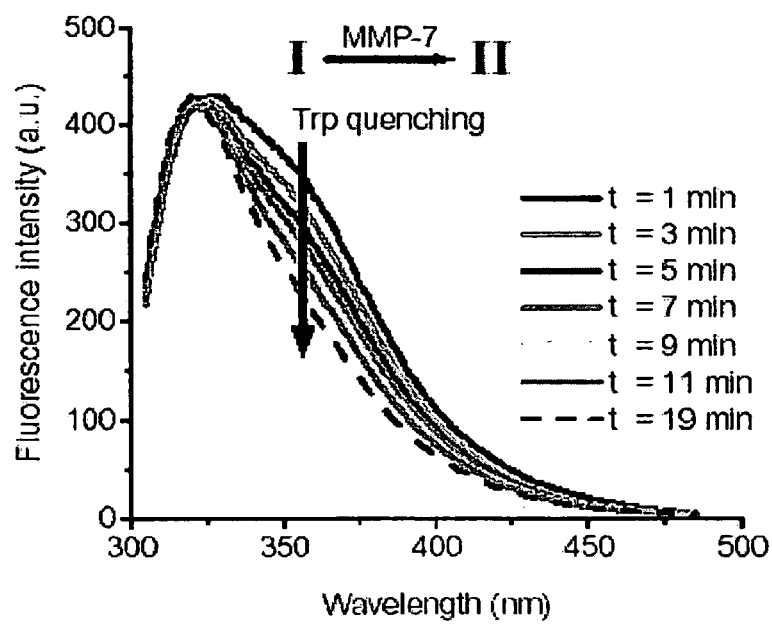
Figure 11:
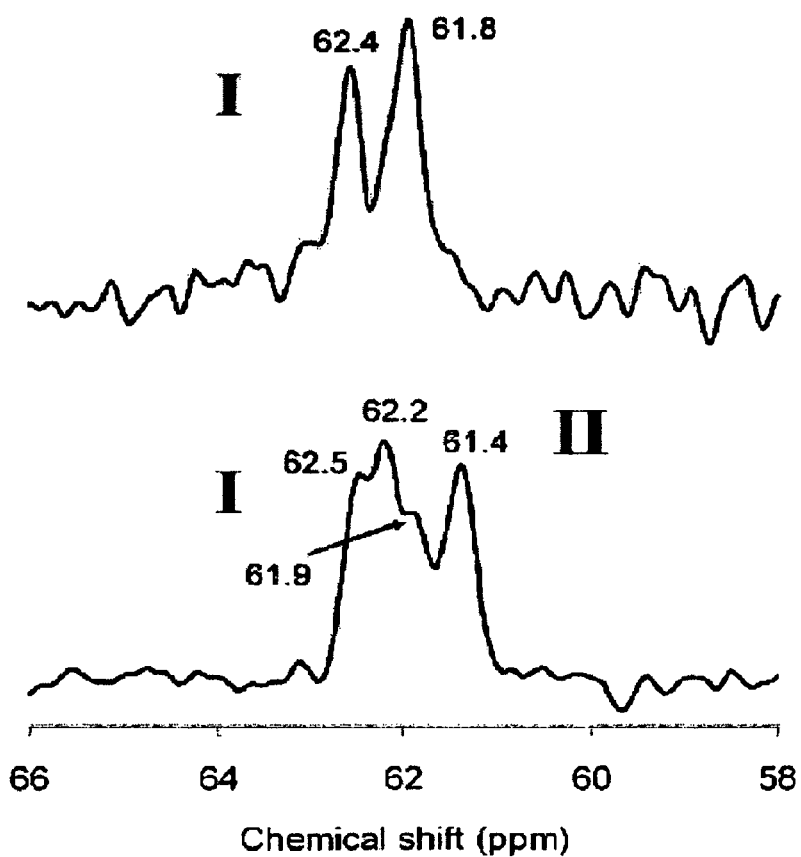
FIG. 11 shows hyperpolarized $^{129}$Xe NMR spectra in $D_2O$ of biosensor I alone (above, blue trace, 154 µM) and a mixture of intact (I, 77 µM, blue labels) and cleaved sensors (II, 95 µM, red labels).
Figure 14:
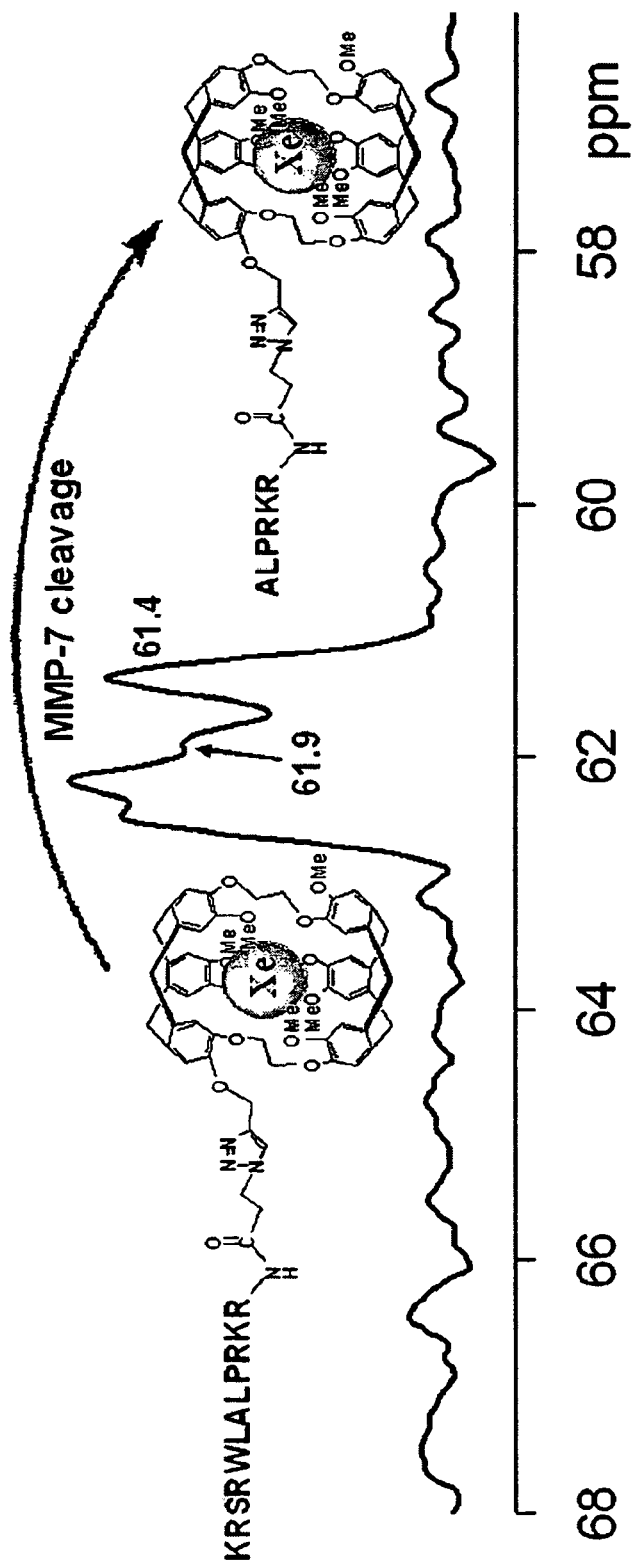
FIG. 14 shows the shift in fluorescence upon proteolysis of $^{129}$Xe biosensor I by MMP-7.

Hyperpolarized $^{129}$Xe NMR experiments clearly revealed differences in the xenon environment between the intact biosensor I and MMP-7 cleaved product II (FIG. 11). The concentration of each compound was determined by UV-vis absorbance measurements at 280 nm in water: $\epsilon_{280}=15,000$ $M^{-1}$ cm$^{-1}$ for the intact biosensor and $\epsilon_{280}=9300$ $M^{-1}$ cm$^{-1}$ for the cleaved biosensor. Chemical shift assignments were based on using free $^{129}$Xe in $D_2O$ at 186.2 ppm as the reference. Raw Fourier transforms were fitted to the double and quadruple Lorentzian line forms prior to applying 20-Hz Gaussian broadening. As shown in FIG. 7, each spectrum of intact and cleaved Xe biosensors consisted of two peaks separated by 0.6 ppm and 0.8 ppm, respectively, which were attributed to diastereomers of the peptide-cage conjugates (RL and LL) that originated from the chirality of the two components, peptide and cryptophane-A. The two diastereomer peaks for I (FIG. 11, top trace) were at 61.8 ppm and 62.4 ppm with linewidths of 28 Hz and 22 Hz, respectively. In a separate measurement (see Supporting Information), II gave two peaks with very similar chemical shifts, −0.1 ppm and +0.1 ppm for the two diastereomer peaks. According to calculations by Sears et al, (Sears, D. N.; Jameson, C. J.; Harris, R. A. *J. Chem. Phys.* 2004, 120, 3277-3283), the difference in the diastereomer separation might be due to the difference in the electrostatic potential between intact and cleaved Xe biosensor. The diastereomers also showed distinct Xe-binding properties evidenced from the different linewidths they exhibited individually. Because the $^{129}$Xe chemical shift is known to be temperature dependent (~0.28 ppm per ° C.), and it was not possible to control the sample temperature precisely in the home-built NMR spectrometer during the data acquisition, a mixed solution of I and II was prepared to indicate the difference in $^{129}$Xe chemical shift. As shown in FIG. 14, two sets of peaks, major (frequency=61.4, 62.2 ppm; linewidth=25, 21 Hz) and minor (frequency=61.9, 62.5 ppm; linewidth=26, 21 Hz), were observed in the mixed solution. Based on the concentrations of I and II (77 μM and 95 μM, respectively), the major peaks were assigned to Xe encapsulated in the cleaved biosensor II and the minor peaks were due to Xe in the intact biosensor I. The area under each set of peaks was consistent with this assignment. Furthermore, the chemical shift differences between the two major and two minor peaks were 0.8 ppm and 0.6 ppm respectively, which is in agreement with the difference between diastereomer peaks for the cleaved and intact Xe biosensors.

Example 2

Designing $^{129}$Xe NMR Biosensors with Improved Xe Incorporation

A facile synthesis for water-soluble cryptophane was developed and described above, based on the copper (I)-mediated [3+2] azide-alkyne Huisgen cycloaddition. The ten-step synthesis, shown above, yielded triacid-functionalized cryptophane (See FIG. 2) in 4% overall yield. Triacid-functionalized cryptophane (2 mM) was readily dissolved in aqueous base and remained soluble in 100 mM NaCl to pH ~5.5. A solution of triacid-functionalized cryptophane (60 μM) in 1 mM, pH 7.2 phosphate buffer at 300 K had a hyperpolarized $^{129}$Xe NMR chemical shift of 64.6 ppm relative to xenon gas. $^1$H NMR measurements of triacid-functionalized cryptophane in D$_2$O showed only the crown-crown structural isomer at temperatures as high as 333 K.

Triacid-functionalized cryptophane exhibited similar fluorescence in water ($\lambda_{em}$=313 nm) to the six 1,2-dialkoxybenzenes that form its cage. This led us to study the xenon binding equilibrium by heavy-atom quenching:

$$Xe_{(aq)} + 1_{(aq)} \rightleftharpoons Xe@1_{(aq)} \quad (2)$$

Xenon was previously shown to quench 2-phenanthrene sulfonate and pyrene bound to apomyoglobin, but this required a large overpressure of xenon due to its low affinity for the protein. In the current study, fluorescence quenching by xenon provided a sensitive method of measuring Xe binding, even at sub-stoichiometric Xe concentrations.

Figure 15:
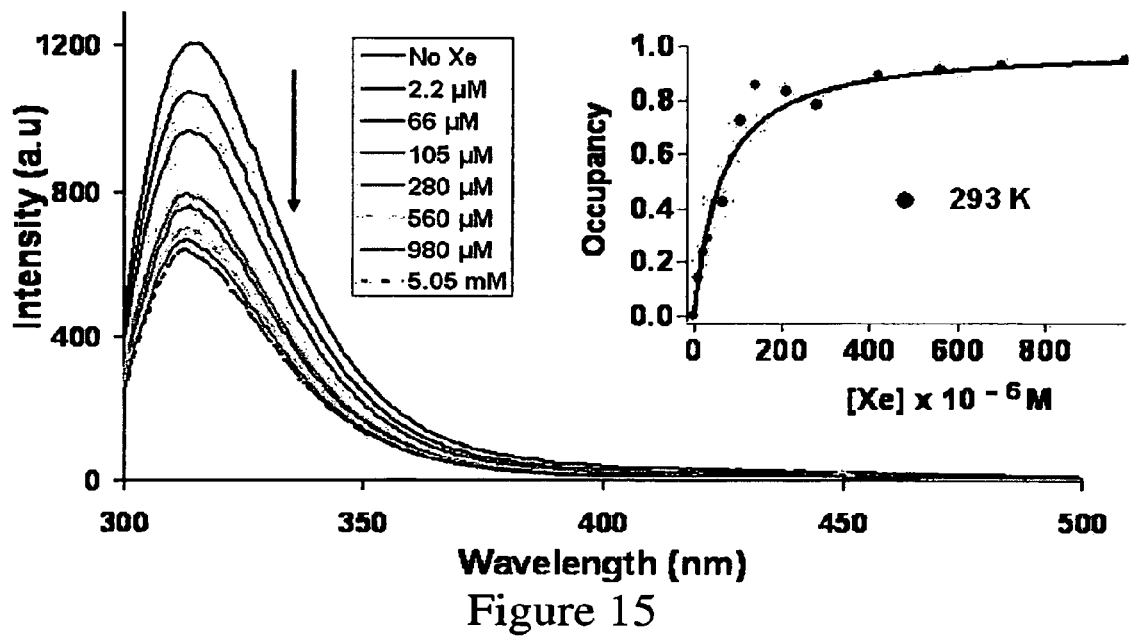
FIG. 15 shows fluorescence quenching of triacid-functionalized cryptophane (15 µM) by Xe in 1 mM, pH 7.2 phosphate buffer, 293 K. Inset: Curve fits for a single-site binding model.

Fluorescence quenching experiments were conducted at 293 K with 1.5×10$^{-5}$ M solutions of 1 in 1 mM, pH 7.2 phosphate buffer. A saturated xenon solution at 310 K ([Xe]= 3.3 mM) was titrated into the septum-sealed cuvette by gastight syringe. To obtain a saturated xenon measurement, xenon gas was bubbled directly into the cuvette. In all cases, fluorescence spectra were collected after thermal equilibration at 293 K (FIG. 15).

The fluorescence maxima were fitted to a single-site binding model using the following relationship:

$$\frac{[Xe@1]}{[Xe@1]+[1]} = \frac{[Xe]}{[Xe]+K_D} \quad (3)$$

Where $K_D$ is the Xe dissociation constant for triacid-functionalized cryptophane. At xenon saturation, [Xe]=5.05 mM at 293 K and 1 atm, the cryptophane fluorescence was half quenched ($F_0/F$=2). This may be explained by preferential Xe interaction, on the sub-nanosecond timescale of fluorescence, with one of the two cyclotriveratrylene units that make up the cryptophane. No cryptophane impurities or concentration dependent phenomena were observed that might also contribute to partial fluorescence quenching. An association constant of 1.7±0.2×10$^4$ M$^{-1}$ (1 std. dev.) was obtained at 293 K. This value is roughly twice the best reported $K_A$ values for cryptophane-A derivatives in water at room temperature.

Figure 16:
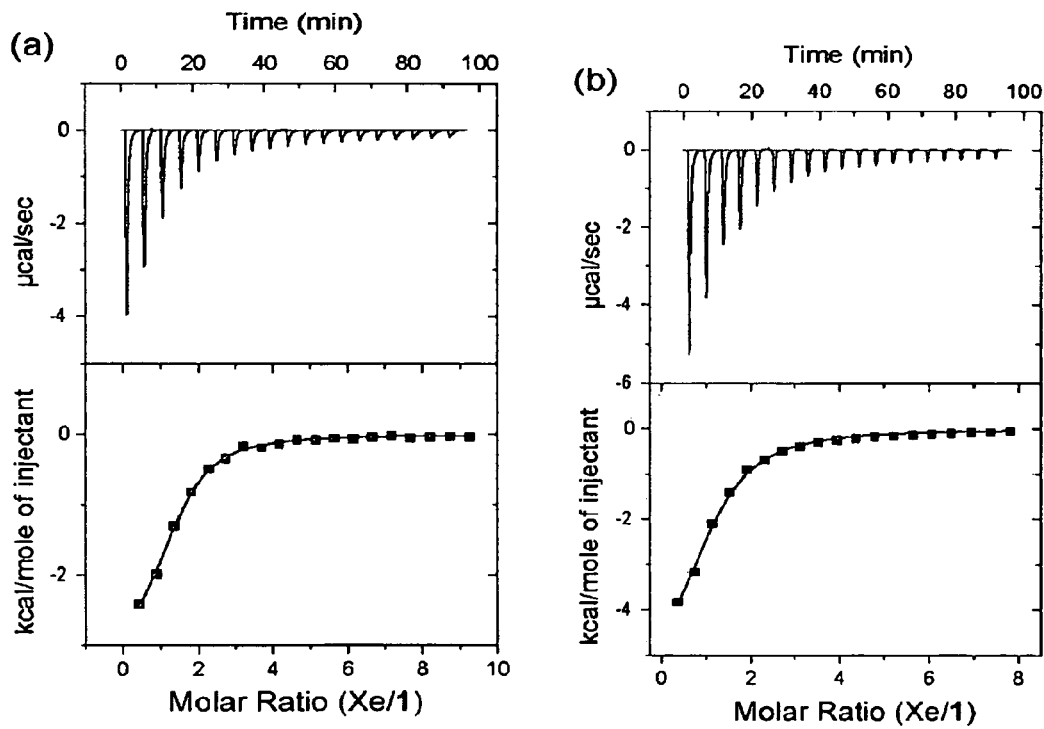
FIG. 16 shows enthalpograms of (a) triacid-functionalized cryptophane (88 µM) in phosphate buffer at 310 K titrated with saturated aqueous xenon (3.3 mM); and (b) triacid-functionalized cryptophane (112 µM) in human plasma at 310 K titrated with xenon-saturated plasma (4.0 mM).
Figure 17:
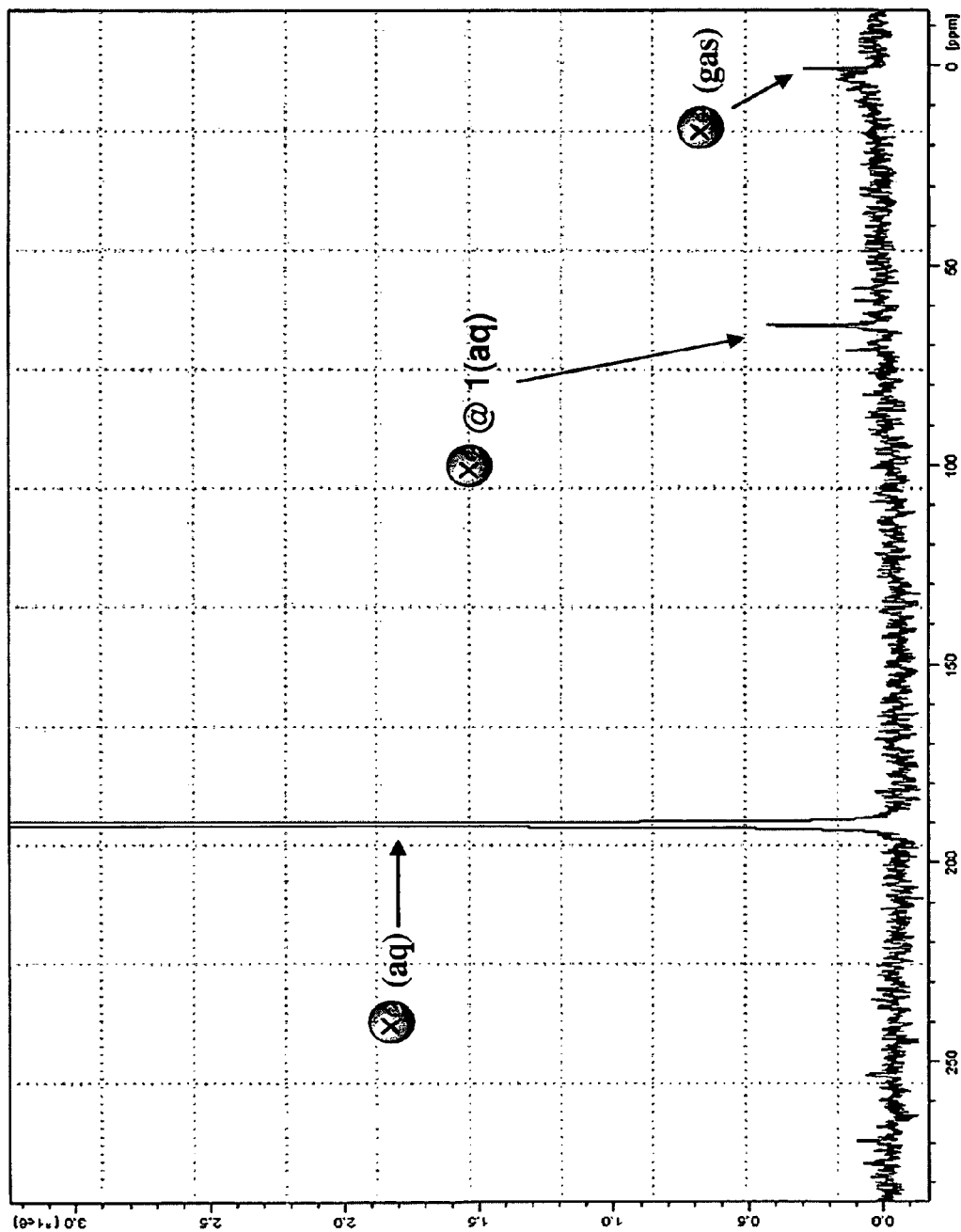
FIG. 17 shows hyperpolarized $^{129}$Xe spectrum of 60 µM triacid-functionalized cryptophane in 1 mM pH 7.2 phosphate buffer.
Figure 18:
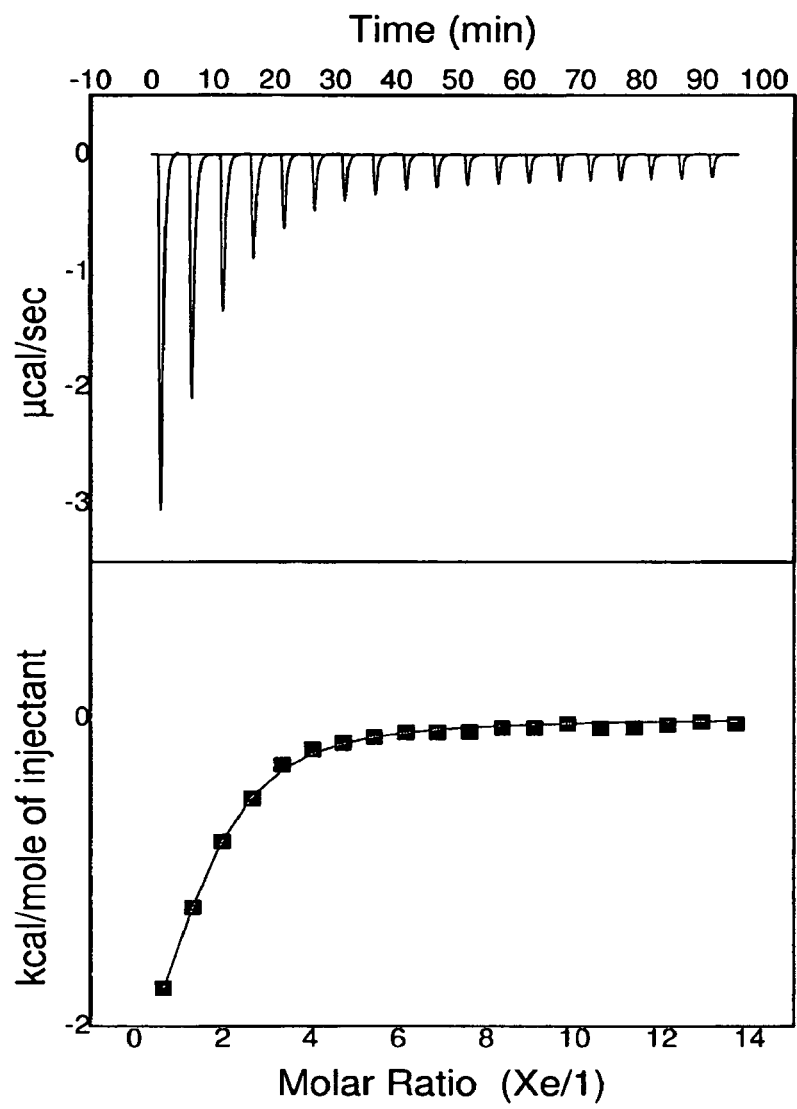
FIG. 18 shows enthalpograms of triacid-functionalized cryptophane (80 µM) in 20 mM, pH 7.5 phosphate buffer at 293 K titrated with saturated aqueous xenon (5.05 mM).
Figure 19:
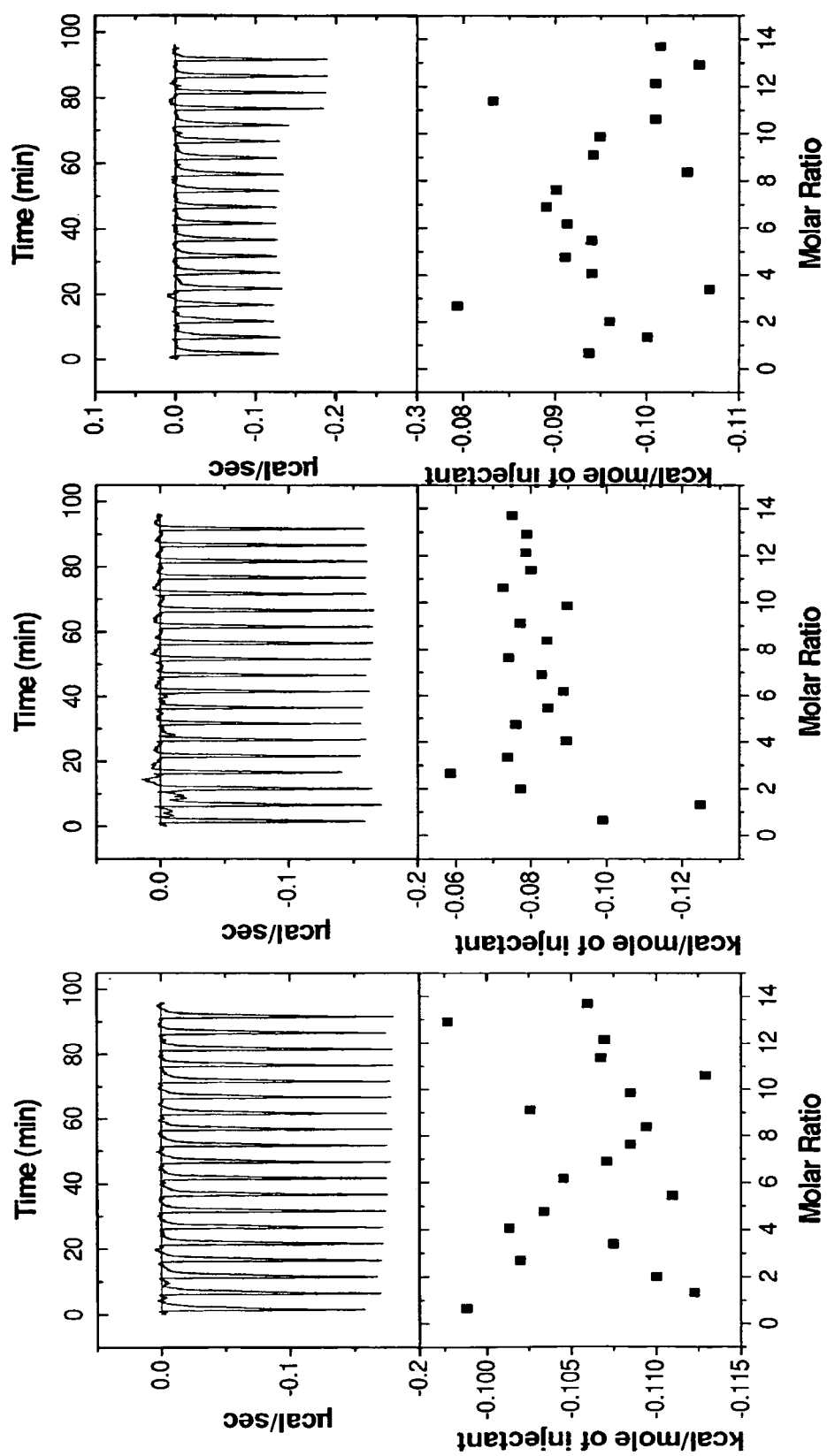
FIG. 19 shows buffer controls at 293 K: a) Water titrated into 20 mM phosphate buffer, pH 7.5 b) Water titrated into a solution of triacid-functionalized cryptophane in 20 mM phosphate buffer, [triacid-functionalized cryptophane]=80 µM c) Xenon-saturated water titrated into 20 mM phosphate buffer, [Xe]=5.05 mM.
Figure 20:
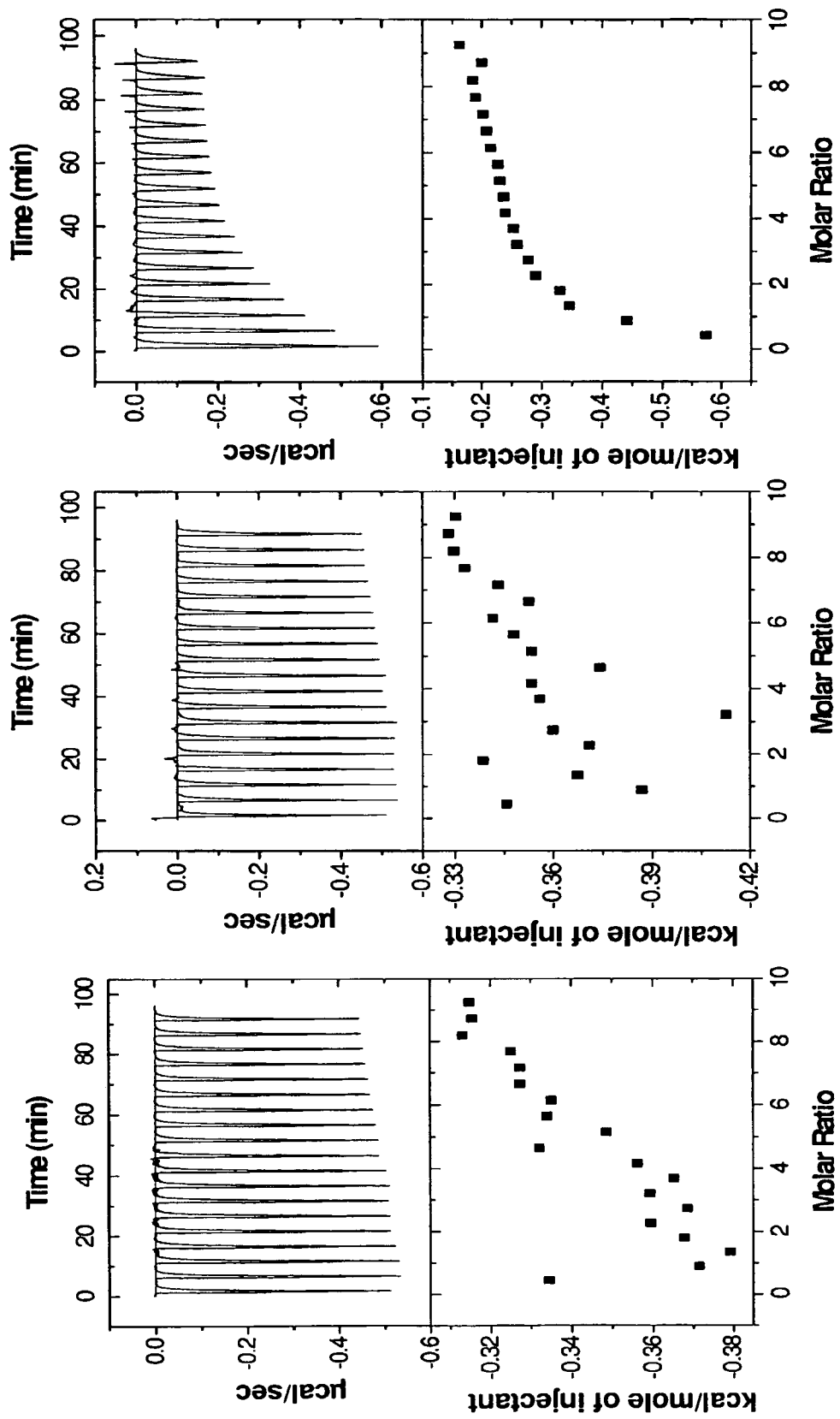
FIG. 20 shows buffer controls at 310 K: a) Water titrated into 20 mM phosphate buffer; pH 7.5 b) Water titrated into a solution of triacid-functionalized cryptophane in 20 mM phosphate buffer, [triacid-functionalized cryptophane]=88 µM; c) Xenon-saturated water titrated into 20 mM phosphate buffer, [Xe]=3.3 mM.
Figure 21:
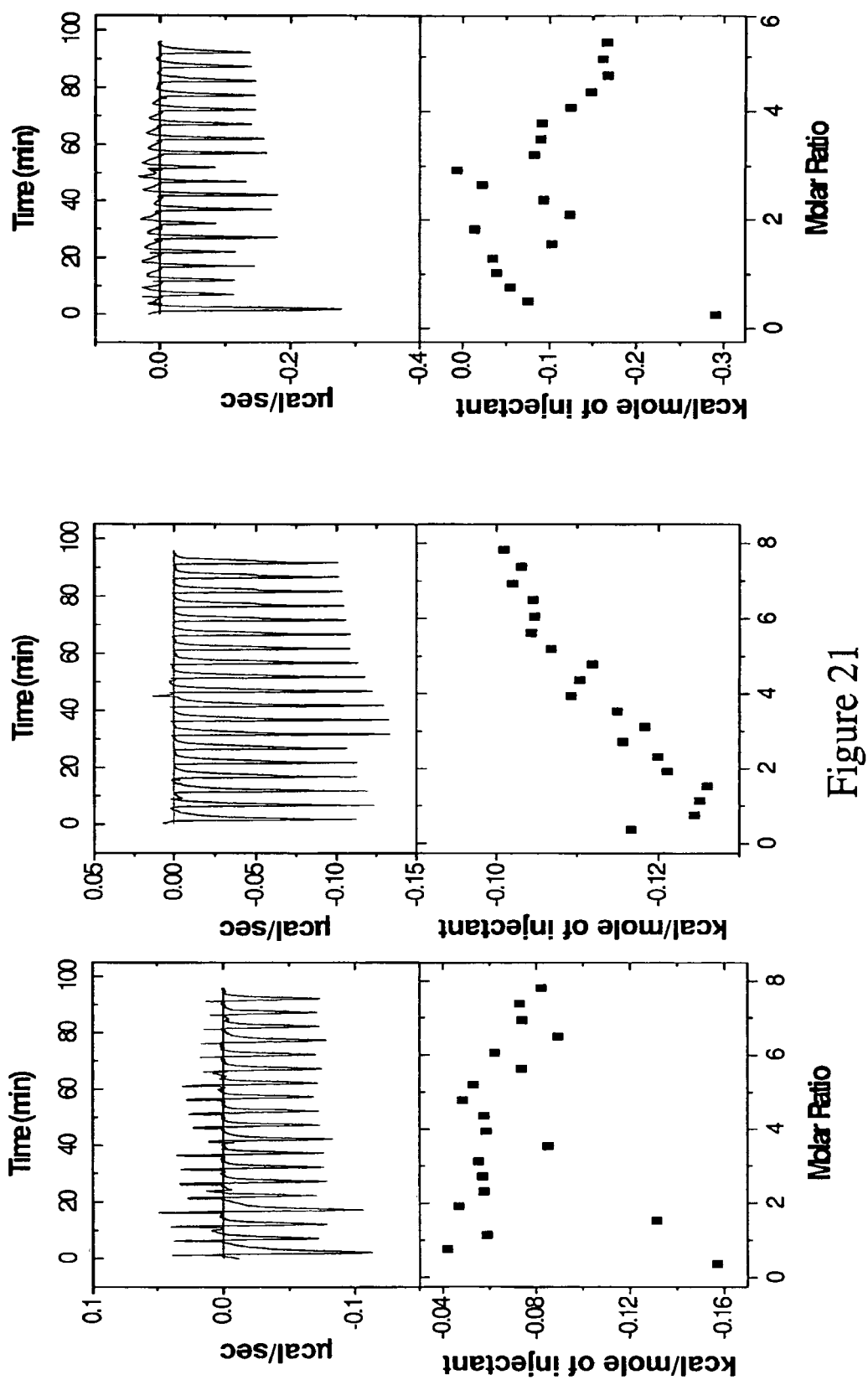
FIG. 21 shows plasma controls at 310 K: a) plasma titrated into plasma; b) triacid-functionalized cryptophane in plasma titrated into plasma, [triacid-functionalized cryptophane]= 112 µM; c) xenon-saturated plasma titrated into plasma, [Xe]=4 mM.
Figure 22:
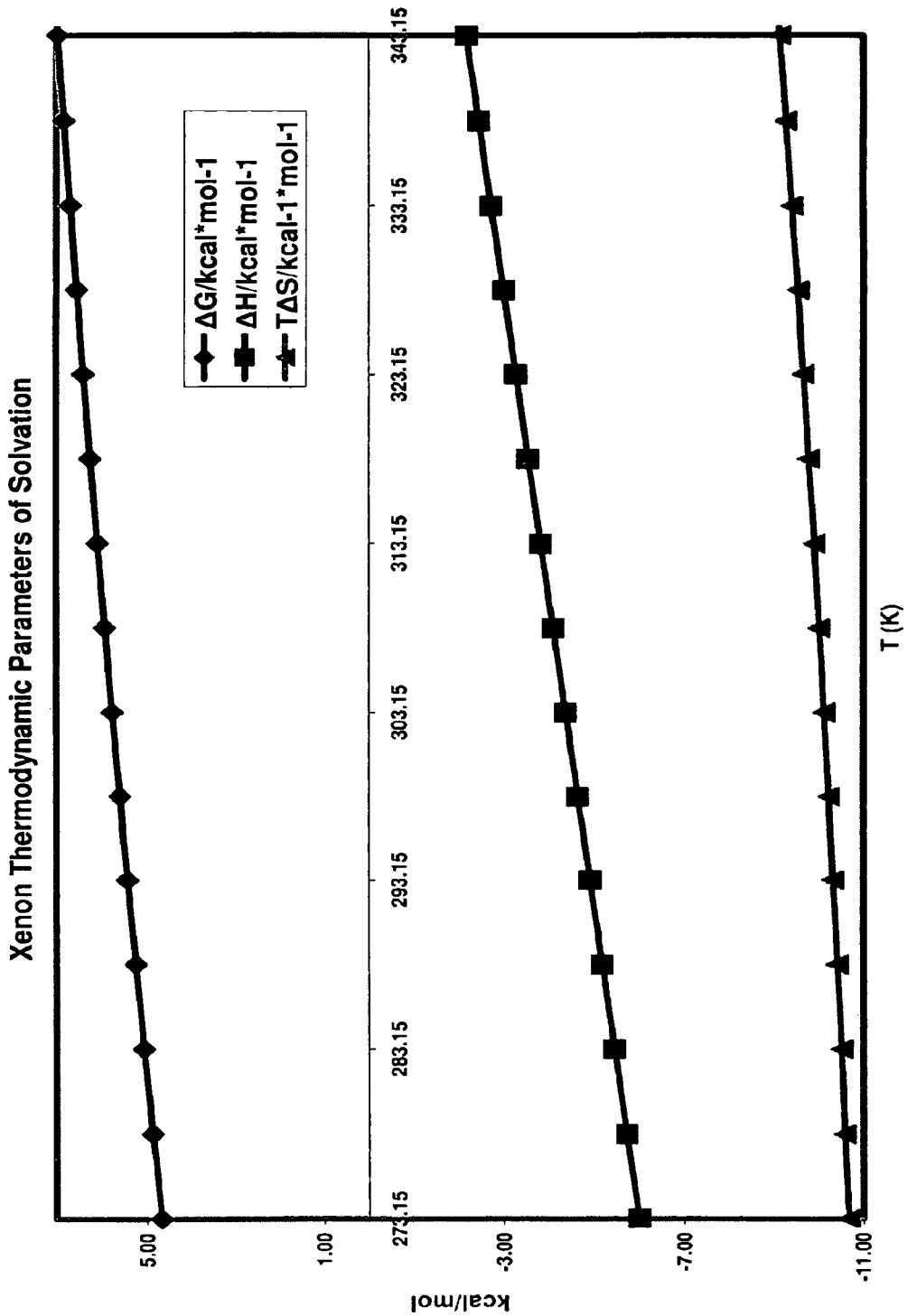
FIG. 22 shows plotted xenon thermodynamic parameters of solvation ($Xe_{(g)} \rightarrow Xe_{(aq)}$), illustrating trends in xenon solvation energy.

Xenon binding was also determined by isothermal titration calorimetry (ITC), which directly measured the heat released during Xe association. ITC measurements were undertaken in 20 mM, pH 7.5 phosphate buffer at 293 K and 310 K as well as in human plasma at 310 K (FIG. 16).

The association constants obtained from fits of ITC data at 293 K ($K_A$=1.73×10$^4$ M$^{-1}$, Table I) and fluorescence quenching were in excellent agreement. A higher binding affinity ($K_A$=3.01×10$^4$ M$^{-1}$) was observed in buffer at physiological temperature. It is apparent from the relative magnitudes of ΔH and −TΔS at 293 and 310 K in phosphate buffer that entropy was a major contributor to xenon binding. This was likely a consequence of the 20 water molecules that make up the first solvation sphere of the Xe atom in aqueous solution.

Xenon binding in plasma, while comparable to buffer at 310 K, showed significant differences in measured enthalpy and entropy. From Table I and the known thermodynamics of xenon partitioning into water, an upper limit of ΔH=−7.5 kcal/mol was calculated for the enthalpy of xenon binding to triacid-functionalized cryptophane. (See FIGS. 17-22 for details.) Thus, the measured ΔH of −6.04 kcal/mol, although larger than in buffer, appeared reasonable. Furthermore, the average literature value for xenon solubility in plasma at 310 K is 3.6 mM, which is ~10% higher than in buffer. These results suggest that xenon interacts with proteins and lipids in plasma, which reduces the contribution of entropy (TΔS=0.12, Table 1) relative to Xe binding triacid-functionalized cryptophane in buffer.

TABLE I

| | $K_A$ (M$^{-1}$ × 10$^4$) | ΔG (kcal mol$^{-1}$) | ΔH (kcal mol$^{-1}$) | TΔS (kcal mol$^{-1}$) |
|---|---|---|---|---|
| Buffer 293 K | 1.73 ± 0.17 | −5.69 | −3.14 ± 0.20 | 2.55 |
| Buffer 310 K | 3.01 ± 0.26 | −6.36 | −3.56 ± 0.13 | 2.80 |
| Plasma 310 K | 2.19 ± 0.22 | −6.16 | −6.04 ± 0.33 | 0.12 |

Example 3

Designing $^{129}$Xe NMR Biosensors for Targeting $\alpha_v\beta_3$ Integrins

Studies have been conducted in the lab to assess the cell deliverability, toxicity, and targetability of Xe biosensors.

Many cancer cells are known to present on their surfaces higher than normal levels of integrins. Cyclic RGD peptides, as well as RGD repeats (i.e., tetraRGD: RGDRGDRGDRGD) are known to bind some integrins with very high affinity, and get taken up into cells. Thus, the attachment of tetraRGD to a cryptophane was expected to produce preferential uptake by some cancer cells relative to healthy cells (i.e., red blood cells) that do not express integrins on their surface.

Figure 23:
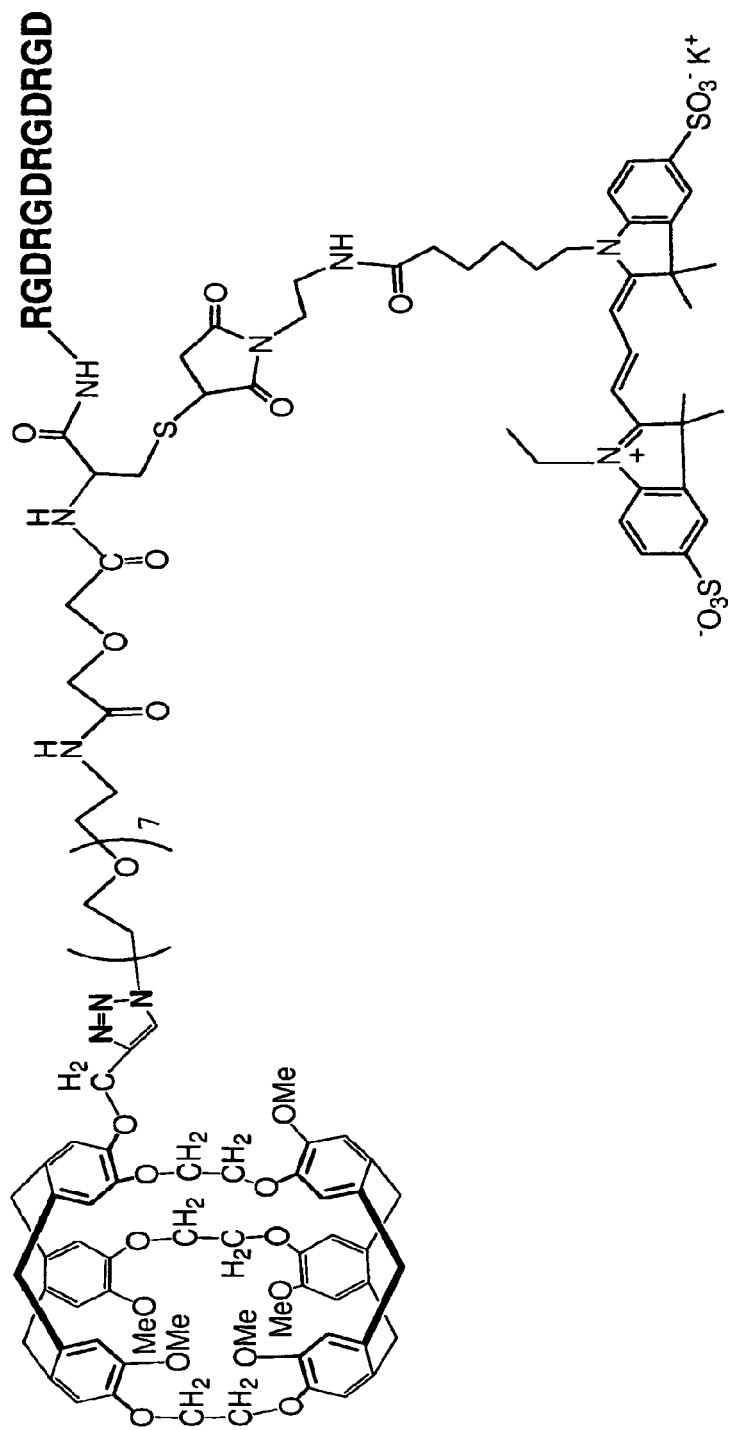
FIG. 23 shows $^{129}$Xe biosensor, which was synthesized for targeting αvβ3 integrin, which, like many integrins, is overexpressed on the surface of many cancer cells.

$^{129}$Xe biosensor was synthesized for targeting $\alpha_v\beta_3$ integrin, which is over-expressed on the surface of many pancreatic cancer cells and is shown in FIG. 23.

Figure 24:
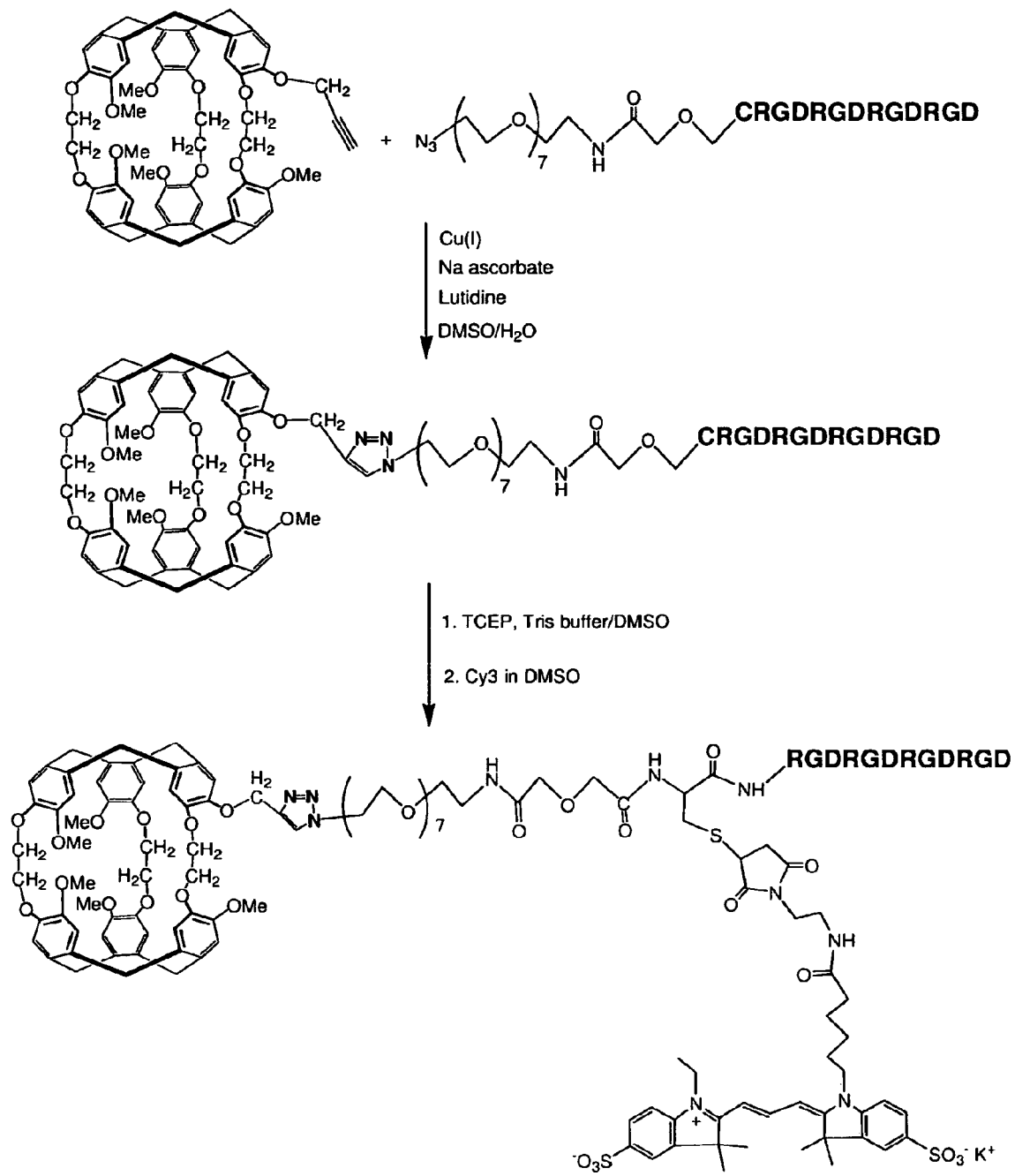
FIG. 24 shows synthesis of tetraRGD $^{129}$Xe biosensor, labeled with Cy3 dye.
Figure 25A:
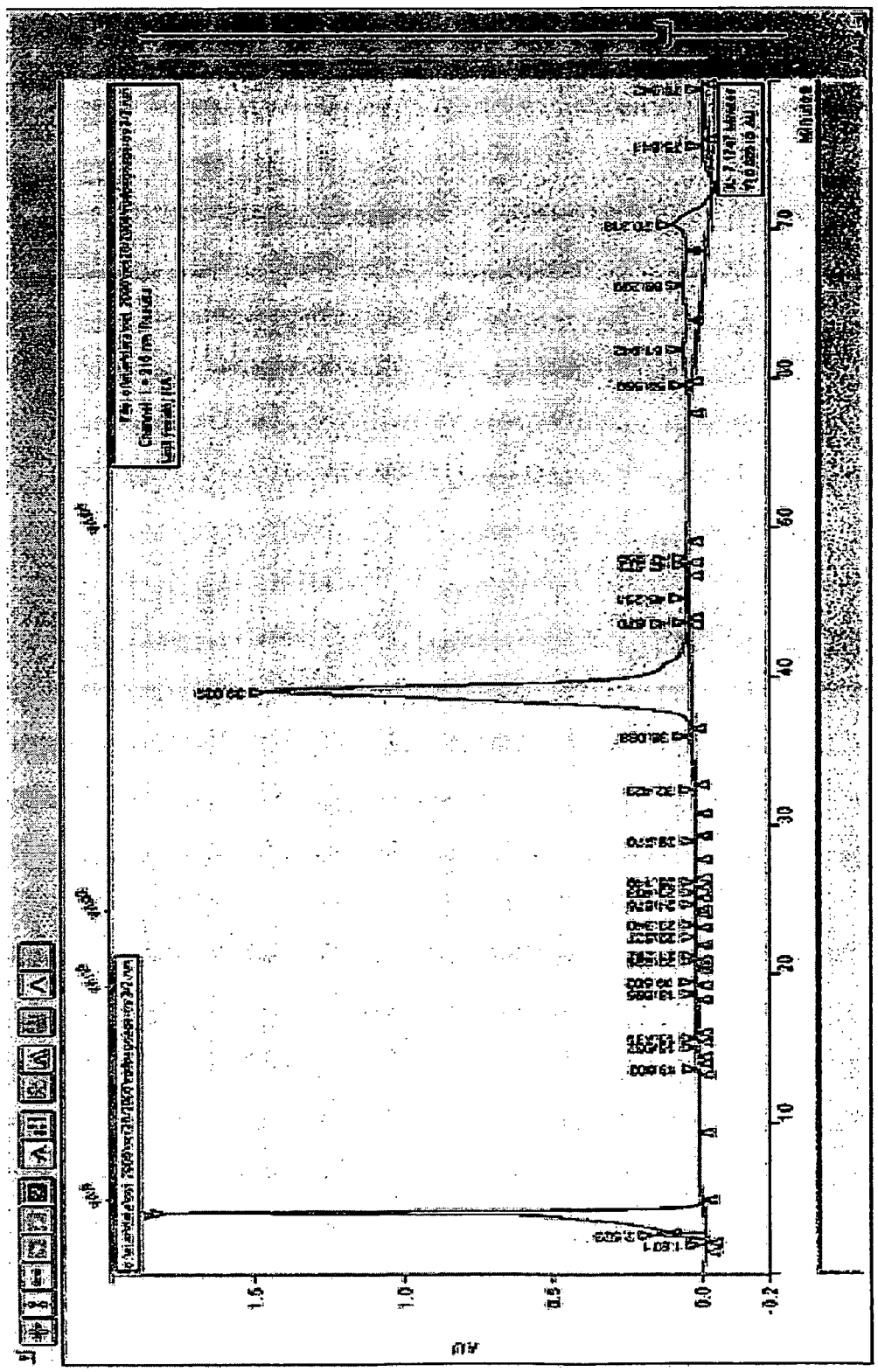
FIG. 25 shows the characterization of the Cy3-labeled biosensor containing the tetraRGD peptide.
Figure 25B:
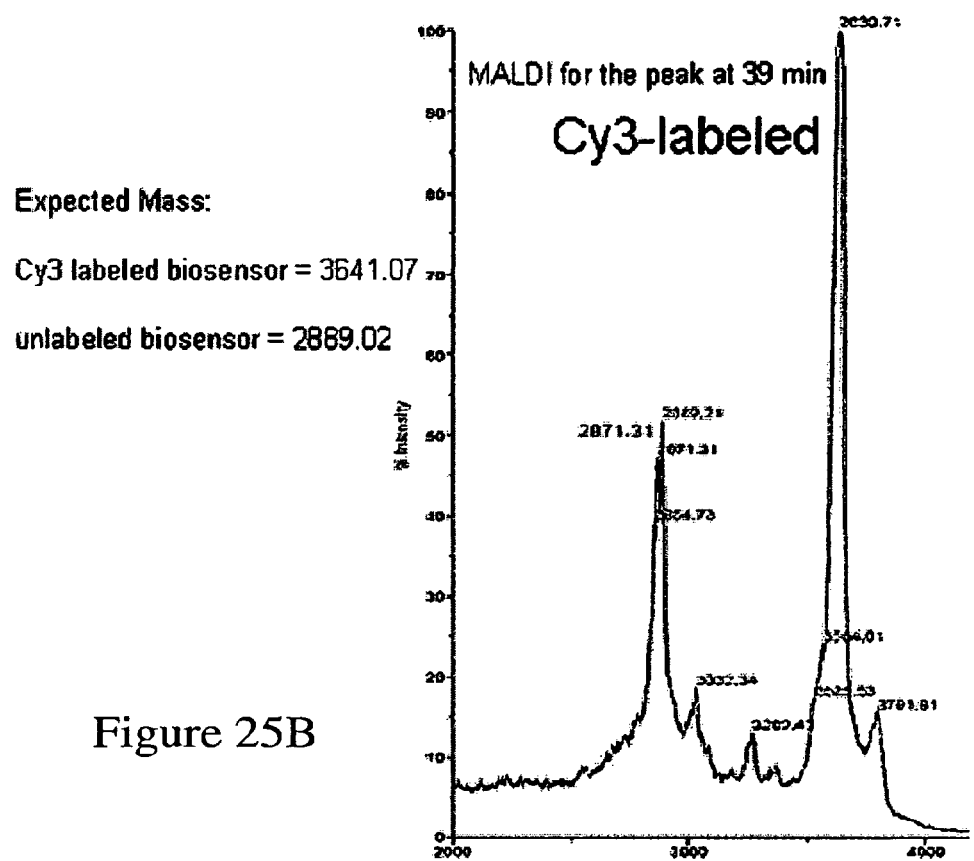
Figure 25C:
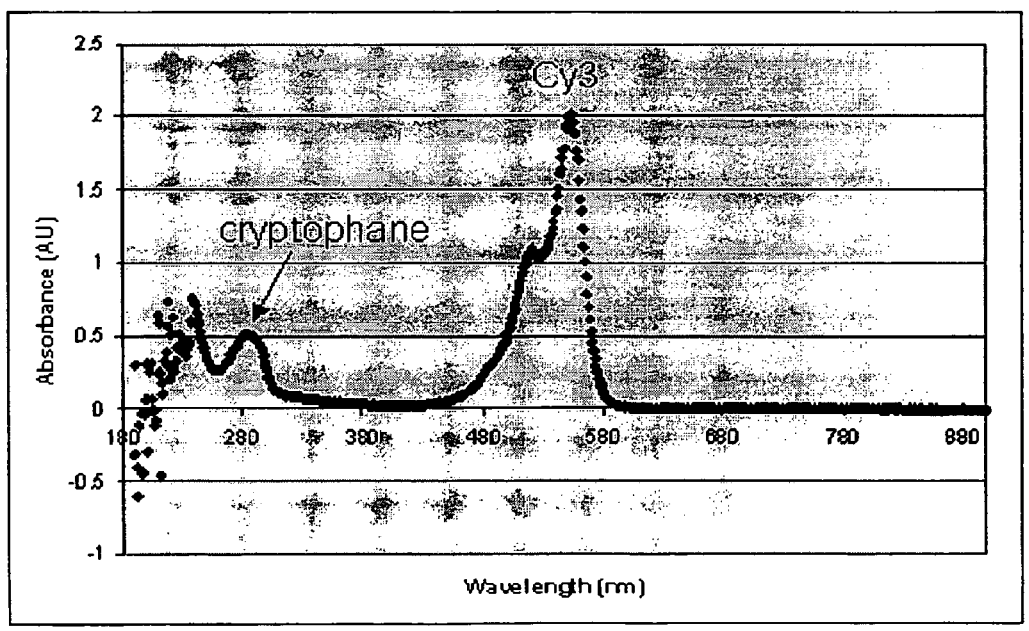

In addition, the biosensor was labeled with Cy3, an NIR dye. The scheme for labeling the cryptophane biosensor containing the tetra-RGD peptide (RGDRGDRGDRGD, SEQ ID. No. 30) is shown in FIG. 24. Labelling efficiency was characterized at 40%, using UV/Vis spectrophtometry, as shown in FIG. 25, as part of the characterization of the Cy3-labelled $^{129}$Xe biosensor.

Cellular uptake was confirmed via confocal microscopy. Cells were incubated with 2 μM tetraRGD-cryptophane for 15 minutes, washed, and imaged via confocal microscope. Cells expressing $\alpha_v\beta_3$ integrin exhibited fluorescence (A-F) while cells not expressing $\alpha_v\beta_3$ showed little fluorescence (G,H). A-B) CAPAN-2, C-D) HFL-1, E-F) NCI-H1975, G-H) human red blood cells.

Cytotoxicity was assessed using a standard MTT assay protocol. Data presented are the average of four trials assessing the viability of cells that soaked with the compound for 24 h, relative to healthy controls, indicating that the Cy3-labelled $^{129}$Xe biosensor is non-toxic at the range of concentrations (1-100 μM) that will be required for in vivo studies.

Figure 26:
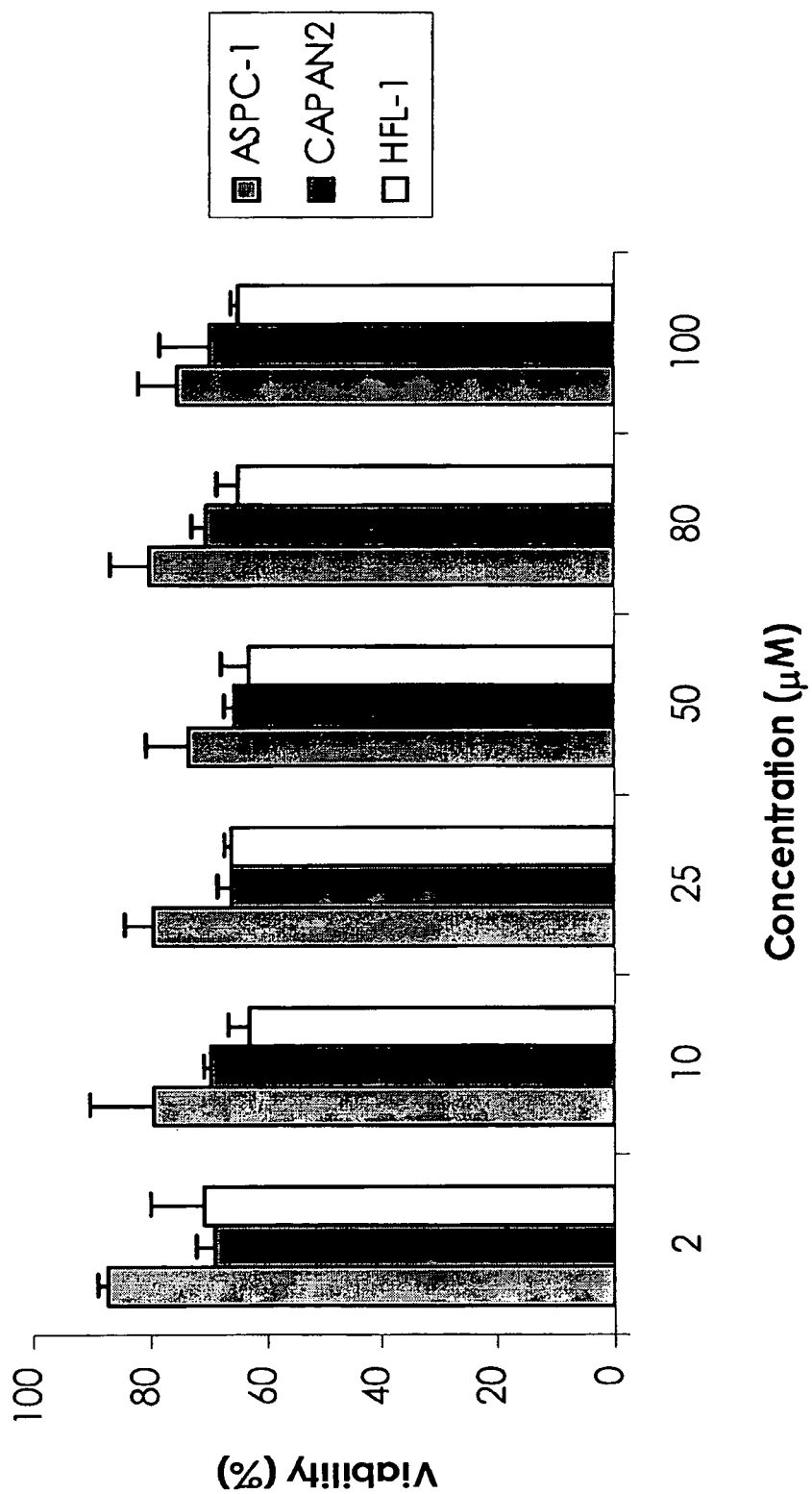
FIG. 26 shows that Cy3 dye-labeled $^{129}$Xe biosensor is not toxic between 1-100 μM.
Figure 27:
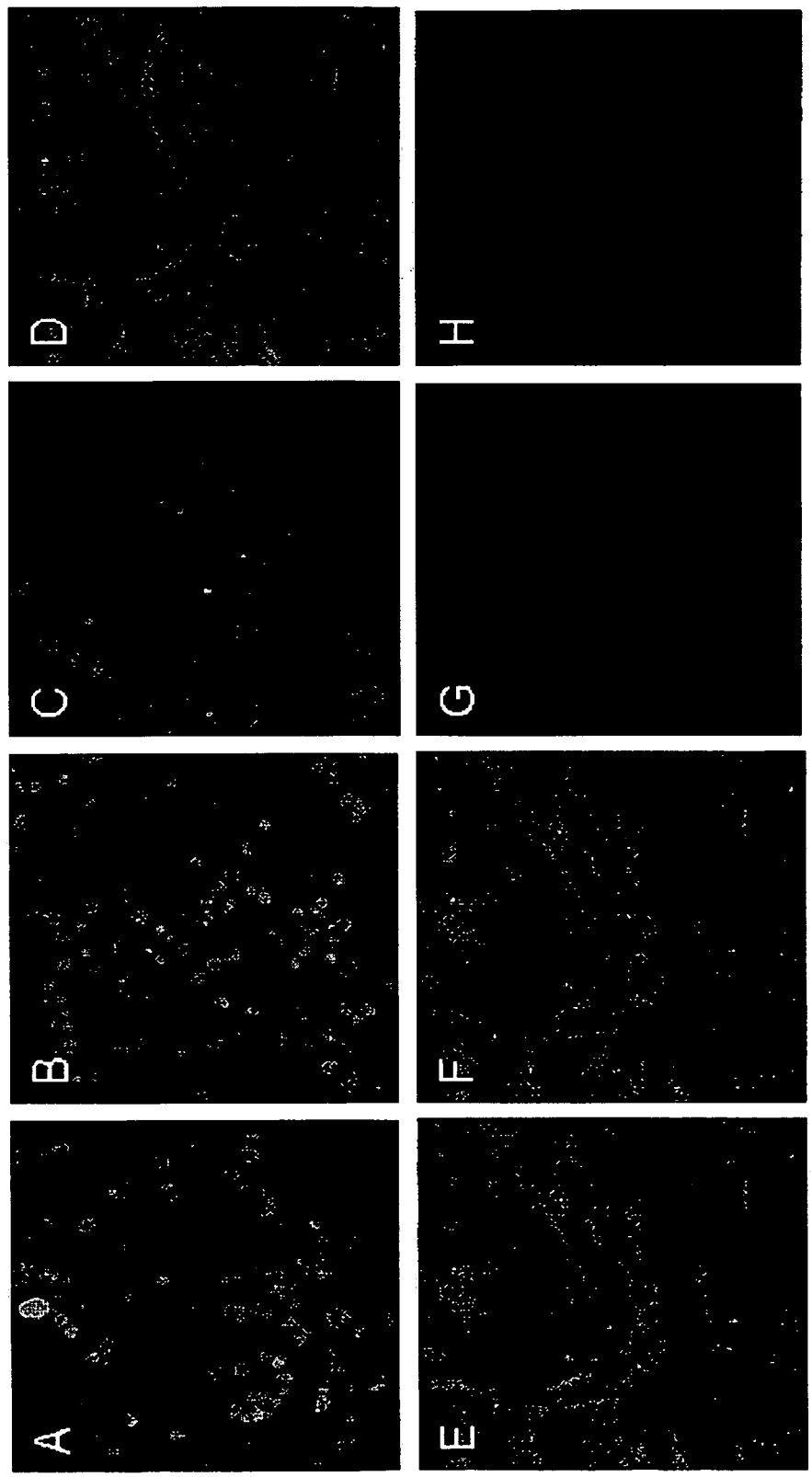
FIG. 27 shows cell uptake of the Cy3 dye-labeled $^{129}$Xe biosensor, confirmed via confocal microscopy. Cells were incubated with 2 mM tetraRGD-cryptophane for 15 minutes, washed, and imaged via confocal microscope. Cells expressing $α_vβ3$ integrin exhibited fluorescence (A-F) while cells not expressing showed little (G,H). A-B) CAPAN-2, C-D) HFL-1, E-F) NCI-H1975, G-H) human red blood cells.
Figure 28:
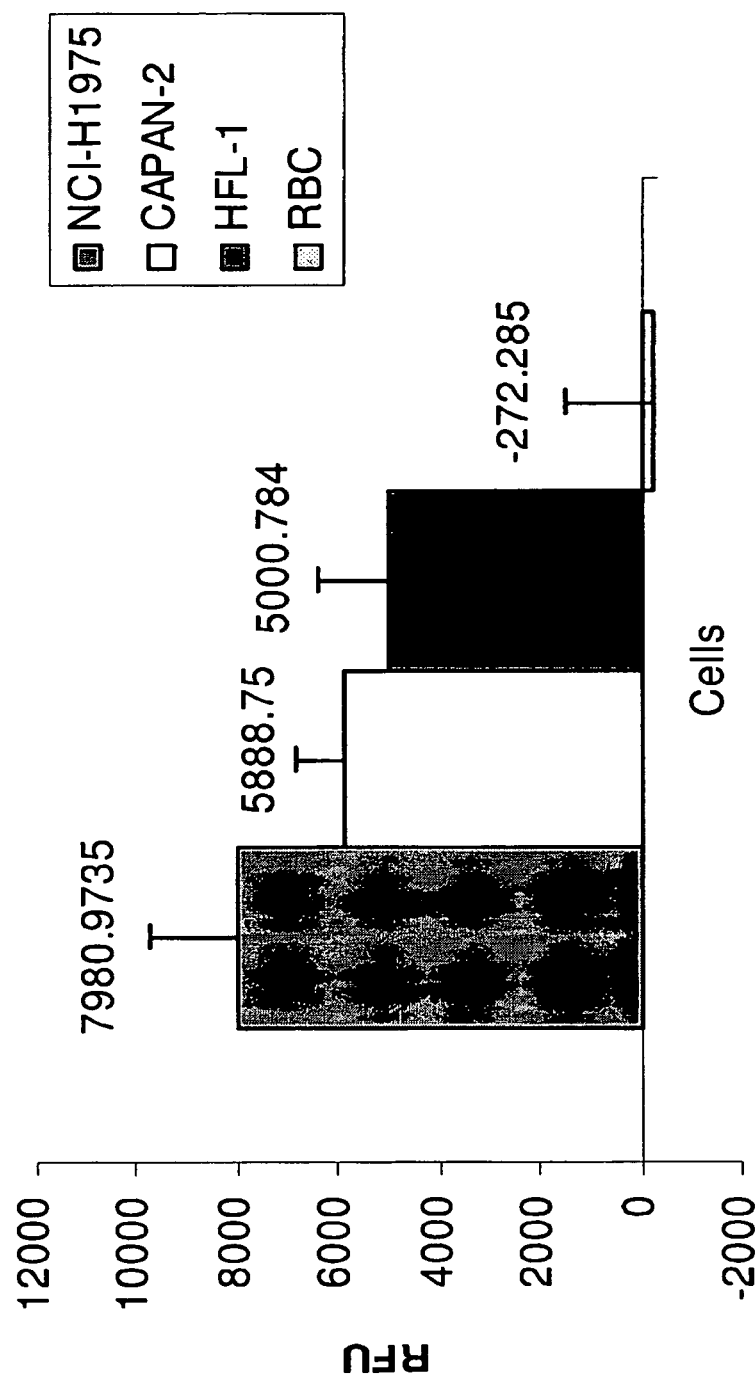
FIG. 28 shows fluorescence quantification of cellular uptake of dye-labeled $^{129}$Xe biosensor.

Very efficient uptake by Xe biosensors containing tetraRGD was found in lung and pancreatic cancer cell lines, and no uptake by red blood cells, as shown in FIGS. 26 and 27. Just as importantly, cell uptake of the tetra-RGD cryptophane was blocked by cyclic RGD peptide, which indicates that the uptake pathway for the Xe biosensor is mediated by integrins, and therefore can be designed to be cell specific.

Example 4

Uptake of Xe Biosensors by Human Cancer Cells

Figure 29:
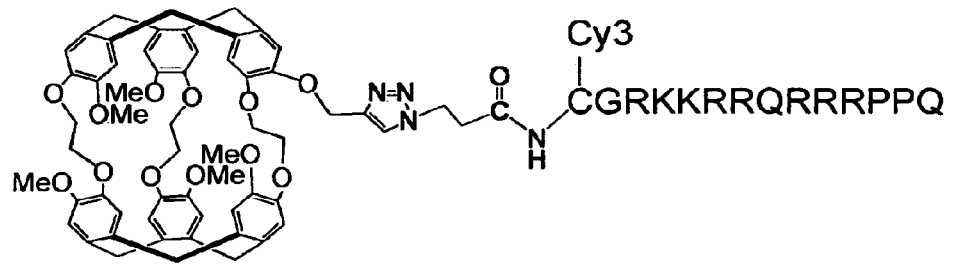
FIG. 29 shows Xe biosensors containing specific carbonic anhydrase inhibitor.
Figure 30:
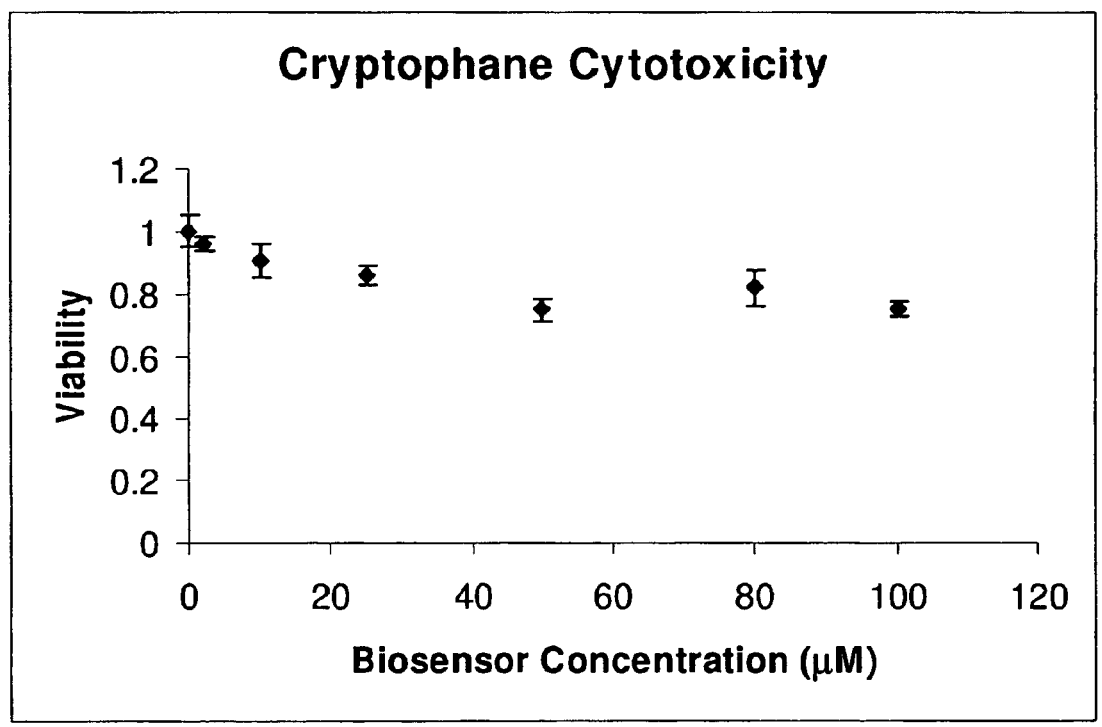
FIG. 30 shows that the Xe biosensor in CAPAN-2 pancreatic cancer cell lines (30-min soak with 5 mM Xe biosensor), has limited toxicity.
Figure 31:
FIG. 31 shows cellular uptake as evidenced by fluorescence (FIG. 31A) and differential interference contrast (DIC) microscopy (FIG. 31B).
Figure 31:
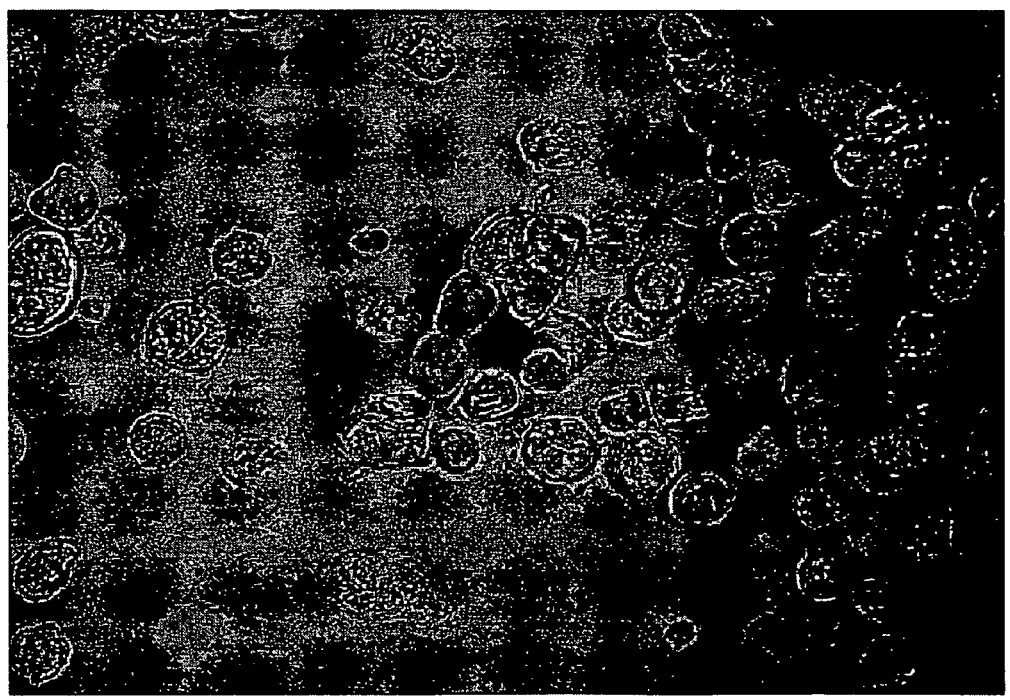

As shown in FIGS. 29-31, very efficient uptake of Xe biosensors by cancer cells was achieved (FIG. 29). This was found in CAPAN-2 pancreatic cancer cell lines (30-min soak with 5 mM Xe biosensor), with limited toxicity (FIG. 30); as evidenced by fluorescence (FIG. 31A) and differential interference contrast (DIC) microscopy (FIG. 31B).

Example 5

Binding of Xe Biosensors to Carbonic Anhydrase II

Figures 32, 33:
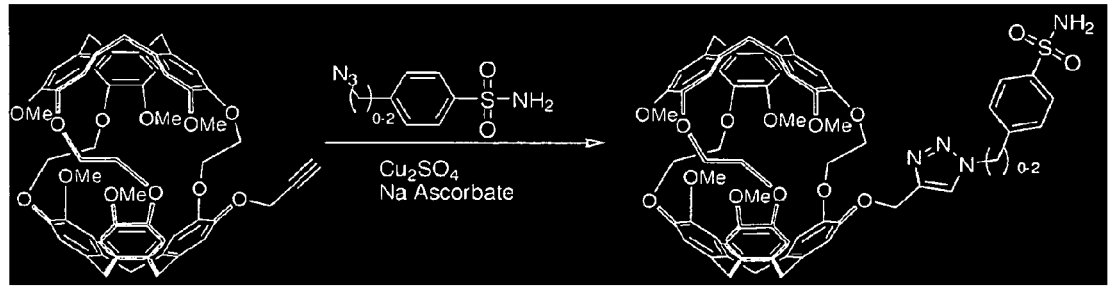
FIG. 32 shows the cryptophane probe that was synthesized, containing a variety of linkers (FIG. 33).
FIG. 33 shows various linkers used in Example 5.
Figure 34:
FIG. 34 shows one embodiment of a Xe biosensor that has been modeled computationally to bind to the active site of carbonic anhydrase II.
Figure 35:
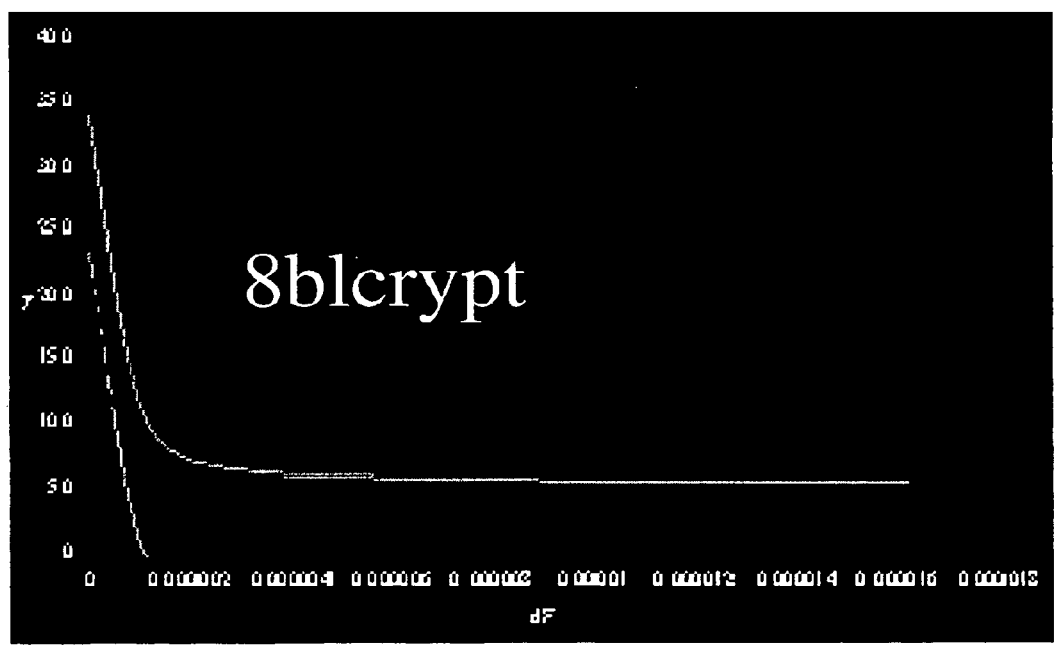
FIGS. 35 and 36 show the efficient binding, by fluorescent displacement assays, of Xe biosensors with an 8-bond linker (FIG. 33) with a dissociation constant of 0.25 μM and a 6-bond linker with a dissociation constant of 1.64 μM, respectively.
Figure 36:
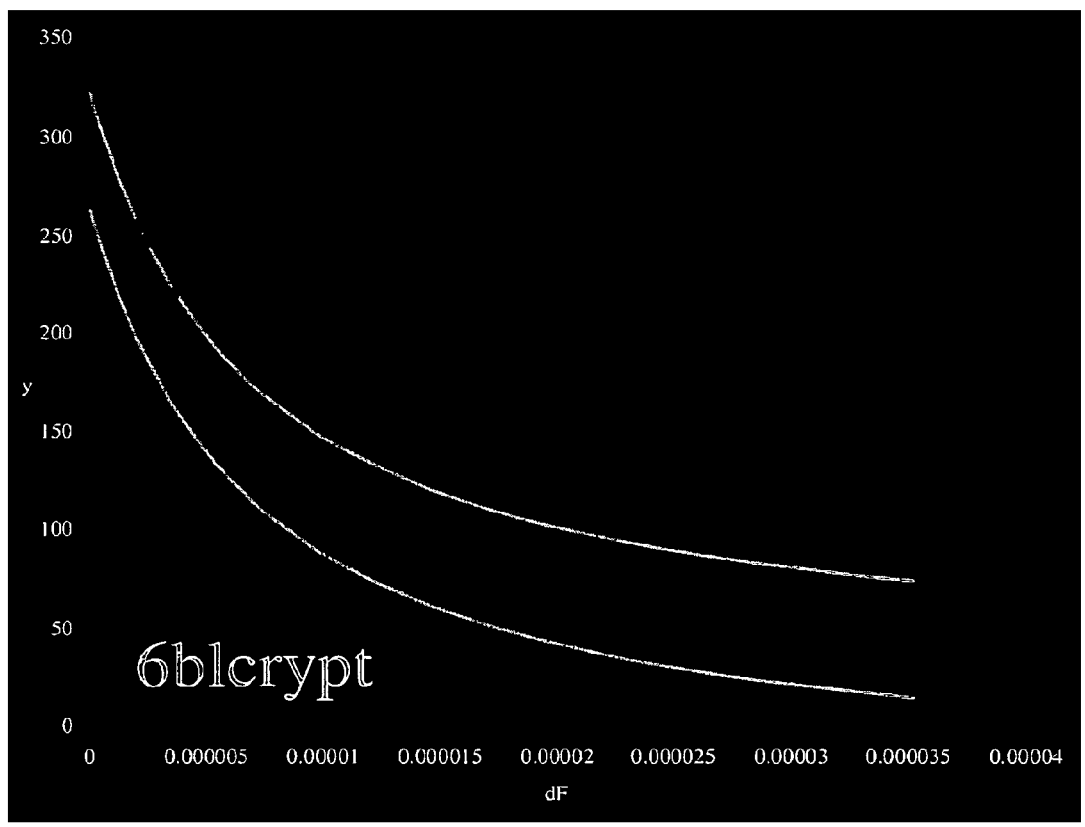

The cryptophane probe was synthesized (FIG. 32), containing a variety of linkers (FIG. 33), attached to a carbonic anhydrase II phenyl sulfonamide inhibitor. FIGS. 35 and 36 show the efficient uptake by the cells of Xe biosensors with an 8 bond linker (FIG. 33) at a concentration of 0.25 μM and a 6 bond linker at a concentration of 1.64 μM.

Having described preferred embodiments of the invention with reference to the accompanying drawings and examples, it is to be understood that the invention is not limited to the precise embodiments, and that various changes and modifications may be effected therein by those skilled in the art without departing from the scope or spirit of the invention as defined in the appended claims.

---

What is claimed is:

1. A chemical reaction-detection system comprising a biosensor, said biosensor comprises: a hyperpolarized noble element complexed with a monopropargyl-cryptophane-A coupled peptide, wherein the peptide is a reactant, specific to said detected chemical reaction and whereby modulation of the reactant induces change in the chemical environment of the noble element resulting in a chemical shift detectable by $^{29}$Xe NMR spectroscopy.

2. The biosensor of claim 1, wherein said hyperpolarized noble element is Xe.

3. The biosensor of claim 2, wherein the hyperpolarized noble element is $^{129}$Xe.

4. The biosensor of claim 1, wherein the reactant is an enzyme and wherein the detected enzyme and its specific substrates is any one of the enzymes and their substrates in Table III.

5. A method of detecting and/or analyzing the activity of a matrix metalloproteinase, a caspase, an enzyme, or an integrin in a biological sample of a subject, comprising the steps of: contacting the biological sample with a biosensor responsive to said matrix metalloproteinase, caspase, enzyme, or integrin, said biosensor comprising a hyperpolarized noble element complexed with a monopropargyl-cryptophane-A coupled peptide, wherein the peptide is a substrate; specific to said detected matrix metalloproteinase, caspase, enzyme, or capable of interacting with the integrin and whereby cleavage of the substrate by the enzyme or internalization of the biosensor coupled to the integrin induces change in the chemical environment of the noble element resulting in a chemical shift detectable by NMR; and analyzing the chemical shift in said element, whereby a chemical shift indicates activity of said metalloproteinase or caspase.

6. The method of claim 5, wherein said noble element is Xe.

7. The method of claim 6, wherein the hyperpolarized noble element is $^{129}$Xe.

8. The method of claim 5, wherein said biological sample is blood, sputum, sera, urine, mucosa, feces, epidermal sample, skin sample, cheek swab, sperm, semen, amniotic fluid, cultured cells, bone marrow sample, chorionic villi, primary tumor biopsies, metastases biopsies, diffuse tumor biopsies, or a combination thereof.

9. A device for screening for the activity of a matrix metalloproteinase, a caspase, an enzyme, or an integrin in a biological sample, comprising a biosensor responsive to said matrix metalloproteinase, caspase, enzyme, or integrin, said biosensor comprising a hyperpolarized noble element complexed with a monopropargyl-cryptophane-A coupled peptide, wherein the peptide is a substrate, specific to said detected matrix metalloproteinase, caspase, enzyme, or capable of interacting with the integrin and whereby cleavage of the substrate by the enzyme or internalization of the biosensor coupled to the integrin induces change in the chemical environment of the noble element resulting in a chemical shift detectable by NMR; and instructions for use.

10. The device of claim 9, wherein the matrix metalloproteinase (MMP) or enzyme is any MMP or enzyme described in Table III with its corresponding substrate as the peptide in said biosensor.

11. The device of claim 9, further comprising an additional MMP, enzyme or integrin-responsive biosensor.

12. The device of claim 11, wherein the additional matrix metalloproteinase (MMP) or enzyme is any MMP or enzyme described in Table III with its corresponding substrate as a peptide in said additional MMP-responsive biosensor.

13. The device of claim 9, wherein said instructions, further comprise a library of chemical shifts identifying each matrix metalloproteinase or enzyme described in Table III.

14. The device of claim 9, wherein said biological sample is blood, sputum, sera, urine, mucosa, feces, epidermal sample, skin sample, cheek swab, sperm, semen, amniotic fluid, cultured cells, bone marrow sample, chorionic villi, primary tumor biopsies, metastases biopsies, diffuse tumor biopsies, or a combination thereof.

15. A method of diagnosing a suspected cancer cell in vivo in a subject as malignant or benign, comprising the step of contacting a suspected cell with a composition comprising a fluorescently labeled biosensor wherein said biosensor comprises: a hyperpolarized noble element; complexed with a monopropargyl-cryptophane-A coupled peptide, wherein the peptide is capable of binding an integrin expressed on the surface of the suspected cancer cell and analyzing the change in fluorescent intensity of the cell before and after administration of the composition, whereby increase in fluorescent intensity, indicates the cell is malignant.

16. The method of claim 15, wherein the peptide is tetra-RGD (SEQ ID. No. 30).

17. The method of claim 15, wherein the detectable label is Cy3 near-infrared (NIRS) dye.

18. The method of claim 15, wherein the cancer cell is melanoma, glioma, ovarian, prostate, breast, pancreatic or lung cancer cell.

19. The method of claim 15, wherein the integrin is $\alpha_v\beta 33$.

* * * * *

SEQUENCE LISTING

```
<160> NUMBER OF SEQ ID NOS: 36

<210> SEQ ID NO 1
<211> LENGTH: 8
<212> TYPE: PRT
<213> ORGANISM: Homo sapiens

<400> SEQUENCE: 1

Pro Gln Gly Ile Ala Gly Gln Arg
1               5

<210> SEQ ID NO 2
<211> LENGTH: 7
<212> TYPE: PRT
<213> ORGANISM: Homo sapiens

<400> SEQUENCE: 2

Pro Leu Ala Leu Trp Ala Arg
1               5

<210> SEQ ID NO 3
<211> LENGTH: 7
<212> TYPE: PRT
<213> ORGANISM: Homo sapiens
```

```
<400> SEQUENCE: 3

Pro Leu Gly Leu Trp Ala Arg
1               5

<210> SEQ ID NO 4
<211> LENGTH: 7
<212> TYPE: PRT
<213> ORGANISM: Homo sapiens
<220> FEATURE:
<221> NAME/KEY: misc_feature
<222> LOCATION: (4)..(5)
<223> OTHER INFORMATION: Nva-Dpa

<400> SEQUENCE: 4

Pro Leu Ala Xaa Xaa Ala Arg
1               5

<210> SEQ ID NO 5
<211> LENGTH: 9
<212> TYPE: PRT
<213> ORGANISM: Homo sapiens

<400> SEQUENCE: 5

Arg Pro Lys Pro Val Glu Trp Arg Lys
1               5

<210> SEQ ID NO 6
<211> LENGTH: 7
<212> TYPE: PRT
<213> ORGANISM: Homo sapiens

<400> SEQUENCE: 6

Pro Tyr Ala Tyr Trp Met Arg
1               5

<210> SEQ ID NO 7
<211> LENGTH: 12
<212> TYPE: PRT
<213> ORGANISM: Homo sapiens

<400> SEQUENCE: 7

Arg Lys Arg Pro Leu Ala Leu Trp Arg Ser Arg Lys
1               5                   10

<210> SEQ ID NO 8
<211> LENGTH: 7
<212> TYPE: PRT
<213> ORGANISM: Homo sapiens

<400> SEQUENCE: 8

Pro Leu Ala Tyr Trp Ala Arg
1               5

<210> SEQ ID NO 9
<211> LENGTH: 7
<212> TYPE: PRT
<213> ORGANISM: Homo sapiens

<400> SEQUENCE: 9

Pro Leu Gly Leu Trp Ala Arg
1               5

<210> SEQ ID NO 10
<211> LENGTH: 7
<212> TYPE: PRT
<213> ORGANISM: Homo sapiens
```

<400> SEQUENCE: 10

Pro Leu Ala Leu Trp Ala Arg
1               5

<210> SEQ ID NO 11
<211> LENGTH: 6
<212> TYPE: PRT
<213> ORGANISM: Homo sapiens
<220> FEATURE:
<221> NAME/KEY: VARIANT
<222> LOCATION: (2)..(2)
<223> OTHER INFORMATION: G or A
<220> FEATURE:
<221> NAME/KEY: VARIANT
<222> LOCATION: (5)..(5)
<223> OTHER INFORMATION: F or A

<400> SEQUENCE: 11

Ala Xaa Ala Met Xaa Leu
1               5

<210> SEQ ID NO 12
<211> LENGTH: 5
<212> TYPE: PRT
<213> ORGANISM: Homo sapiens
<220> FEATURE:
<221> NAME/KEY: misc-feature
<222> LOCATION: (2)..(2)
<223> OTHER INFORMATION: Cha

<400> SEQUENCE: 12

Pro Xaa Gly His Ala
1               5

<210> SEQ ID NO 13
<211> LENGTH: 9
<212> TYPE: PRT
<213> ORGANISM: Homo sapiens
<220> FEATURE:
<221> NAME/KEY: misc-feature
<222> LOCATION: (5)..(5)
<223> OTHER INFORMATION: (p-OMeBz)
<220> FEATURE:
<221> NAME/KEY: misc-feature
<222> LOCATION: (9)..(9)
<223> OTHER INFORMATION: Dpa

<400> SEQUENCE: 13

Pro Leu Ala Cys Xaa Trp Ala Arg Xaa
1               5

<210> SEQ ID NO 14
<211> LENGTH: 12
<212> TYPE: PRT
<213> ORGANISM: Homo sapiens
<220> FEATURE:
<221> NAME/KEY: misc-feature
<222> LOCATION: (7)..(7)
<223> OTHER INFORMATION: Dpa

<400> SEQUENCE: 14

Pro Leu Ala Gln Ala Val Xaa Arg Ser Ser Ser Arg
1               5                   10

<210> SEQ ID NO 15
<211> LENGTH: 7
<212> TYPE: PRT
<213> ORGANISM: Homo sapiens
<220> FEATURE:

```
<221> NAME/KEY: misc-feature
<222> LOCATION: (4)..(5)
<223> OTHER INFORMATION: Nva-Dpa

<400> SEQUENCE: 15

Pro Leu Ala Xaa Xaa Ala Arg
1               5

<210> SEQ ID NO 16
<211> LENGTH: 17
<212> TYPE: PRT
<213> ORGANISM: Homo sapiens
<220> FEATURE:
<221> NAME/KEY: misc_feature
<222> LOCATION: (1)..(1)
<223> OTHER INFORMATION: (Gly-Pro-Hyp)5
<220> FEATURE:
<221> NAME/KEY: misc_feature
<222> LOCATION: (17)..(17)
<223> OTHER INFORMATION: (Gly-Pro-Hyp)5

<400> SEQUENCE: 16

Xaa Gly Pro Lys Gly Pro Pro Gly Val Val Gly Glu Lys Gly Glu Gln
1               5                   10                  15

Xaa

<210> SEQ ID NO 17
<211> LENGTH: 14
<212> TYPE: PRT
<213> ORGANISM: Homo sapiens

<400> SEQUENCE: 17

Asn Glu Ala Tyr Val His Asp Ala Pro Val Arg Ser Leu Asn
1               5                   10

<210> SEQ ID NO 18
<211> LENGTH: 7
<212> TYPE: PRT
<213> ORGANISM: Homo sapiens

<400> SEQUENCE: 18

Tyr Val Ala Asp Ala Pro Val
1               5

<210> SEQ ID NO 19
<211> LENGTH: 8
<212> TYPE: PRT
<213> ORGANISM: Homo sapiens

<400> SEQUENCE: 19

Val Asp Val Ala Asp Ala Phe Cys
1               5

<210> SEQ ID NO 20
<211> LENGTH: 8
<212> TYPE: PRT
<213> ORGANISM: Homo sapiens

<400> SEQUENCE: 20

Val Pro Val Ala Asp Gly Trp Lys
1               5

<210> SEQ ID NO 21
<211> LENGTH: 7
<212> TYPE: PRT
<213> ORGANISM: Homo sapiens
```

```
<400> SEQUENCE: 21

Asp Glu Val Asp Ala Met Cys
1               5

<210> SEQ ID NO 22
<211> LENGTH: 7
<212> TYPE: PRT
<213> ORGANISM: Homo sapiens

<400> SEQUENCE: 22

Asp Glu Val Asp Ala Pro Lys
1               5

<210> SEQ ID NO 23
<211> LENGTH: 7
<212> TYPE: PRT
<213> ORGANISM: Homo sapiens

<400> SEQUENCE: 23

Leu Glu Val Asp Gly Trp Lys
1               5

<210> SEQ ID NO 24
<211> LENGTH: 4
<212> TYPE: PRT
<213> ORGANISM: Homo sapiens

<400> SEQUENCE: 24

Leu Glu Val Asp
1

<210> SEQ ID NO 25
<211> LENGTH: 4
<212> TYPE: PRT
<213> ORGANISM: Homo sapiens

<400> SEQUENCE: 25

Trp His Glu Asp
1

<210> SEQ ID NO 26
<211> LENGTH: 4
<212> TYPE: PRT
<213> ORGANISM: Homo sapiens

<400> SEQUENCE: 26

Val Glu Ile Asp
1

<210> SEQ ID NO 27
<211> LENGTH: 8
<212> TYPE: PRT
<213> ORGANISM: Homo sapiens

<400> SEQUENCE: 27

Val Asp Gln Val Asp Gly Trp Lys
1               5

<210> SEQ ID NO 28
<211> LENGTH: 4
<212> TYPE: PRT
<213> ORGANISM: Homo sapiens

<400> SEQUENCE: 28

Ile Glu Thr Asp
1
```

```
<210> SEQ ID NO 29
<211> LENGTH: 4
<212> TYPE: PRT
<213> ORGANISM: Homo sapiens

<400> SEQUENCE: 29

Leu Glu His Asp
1

<210> SEQ ID NO 30
<211> LENGTH: 12
<212> TYPE: PRT
<213> ORGANISM: Homo sapiens

<400> SEQUENCE: 30

Arg Gly Asp Arg Gly Asp Arg Gly Asp Arg Gly Asp
1               5                   10

<210> SEQ ID NO 31
<211> LENGTH: 6
<212> TYPE: PRT
<213> ORGANISM: Homo sapiens

<400> SEQUENCE: 31

Arg Gly Asp Arg Gly Asp
1               5

<210> SEQ ID NO 32
<211> LENGTH: 9
<212> TYPE: PRT
<213> ORGANISM: Homo sapiens

<400> SEQUENCE: 32

Arg Gly Asp Arg Gly Asp Arg Gly Asp
1               5

<210> SEQ ID NO 33
<211> LENGTH: 12
<212> TYPE: PRT
<213> ORGANISM: Homo sapiens

<400> SEQUENCE: 33

Arg Lys Arg Pro Leu Ala Leu Trp Arg Ser Arg Lys
1               5                   10

<210> SEQ ID NO 34
<211> LENGTH: 6
<212> TYPE: PRT
<213> ORGANISM: Homo sapiens

<400> SEQUENCE: 34

Arg Lys Arg Pro Leu Ala
1               5

<210> SEQ ID NO 35
<211> LENGTH: 6
<212> TYPE: PRT
<213> ORGANISM: Homo sapiens

<400> SEQUENCE: 35

Leu Trp Arg Ser Arg Lys
1               5
```

```
<210> SEQ ID NO 36
<211> LENGTH: 8
<212> TYPE: PRT
<213> ORGANISM: Homo sapiens

<400> SEQUENCE: 36

Arg Pro Leu Ala Leu Trp Arg Ser
1               5
```